(12) United States Patent
Hoey et al.

(10) Patent No.: US 9,907,599 B2
(45) Date of Patent: *Mar. 6, 2018

(54) MEDICAL SYSTEM AND METHOD OF USE

(71) Applicant: Tsunami MedTech, LLC, Menlo Park, CA (US)

(72) Inventors: Michael Hoey, Shoreview, MN (US); John H. Shadduck, Menlo Park, CA (US)

(73) Assignee: Tsunami MedTech, LLC, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/946,885

(22) Filed: Jul. 19, 2013

(65) Prior Publication Data
US 2014/0025057 A1   Jan. 23, 2014

Related U.S. Application Data

(63) Continuation of application No. 12/167,155, filed on Jul. 2, 2008, now Pat. No. 8,579,892, and a
(Continued)

(51) Int. Cl.
*A61B 18/04* (2006.01)
*A61B 17/42* (2006.01)
(Continued)

(52) U.S. Cl.
CPC .............. *A61B 18/04* (2013.01); *A61B 17/42* (2013.01); *A61M 25/10* (2013.01);
(Continued)

(58) Field of Classification Search
CPC .......... A61B 18/04; A61B 2017/00026; A61B 2017/00084; A61B 2017/00504; A61B 2018/00619; A61B 2018/0063
See application file for complete search history.

(56) References Cited

U.S. PATENT DOCUMENTS

| 408,899 A | 8/1889 | Bioch et al. |
| 697,181 A | 4/1902 | Smith |

(Continued)

FOREIGN PATENT DOCUMENTS

| WO | WO 2000/011927 | 3/2000 |
| WO | WO 2000/029055 | 5/2000 |

(Continued)

OTHER PUBLICATIONS

Coda, et al., "Effects of pulmonary reventilation on gas exchange after cryotytic disobstruction of endobronchial tumors," *Minerva Medical*, vol. 72, pp. 1627-1631, Jun. 1981 (with English translation).

(Continued)

*Primary Examiner* — Daniel Fowler
(74) *Attorney, Agent, or Firm* — Levine Bagade Han LLP

(57) ABSTRACT

An instrument and method for applying thermal energy to targeted tissue. An instrument and method for tissue thermotherapy. In one embodiment, a method includes providing a vapor source comprising a pump configured for providing a flow of liquid media from a liquid media source into a vaporization chamber having a heating mechanism, actuating the pump to provide the liquid into the vaporization chamber, applying energy from the heating mechanism to convert a substantially water liquid media into a minimum water vapor level for causing an intended effect in tissue. For examples such levels can comprise at least 60% water vapor, at least 70% water vapor, at least 80% water vapor or at least 90% water vapor for causing an intended effect in tissue.

36 Claims, 38 Drawing Sheets

Related U.S. Application Data continuation-in-part of application No. 10/681,625, filed on Oct. 7, 2003, now Pat. No. 7,674,259, and a continuation-in-part of application No. 11/158,930, filed on Jun. 22, 2005, now Pat. No. 7,892,229, and a continuation-in-part of application No. 11/244,329, filed on Oct. 5, 2005, now Pat. No. 8,016,823, and a continuation-in-part of application No. 11/329,381, filed on Jan. 10, 2006, now Pat. No. 8,444,636.

(60) Provisional application No. 60/929,632, filed on Jul. 6, 2007.

(51) Int. Cl.
 *A61M 25/10* (2013.01)
 *A61B 17/00* (2006.01)
 *A61B 18/00* (2006.01)
 *A61B 90/00* (2016.01)

(52) U.S. Cl.
 CPC ........... *A61B 2017/00026* (2013.01); *A61B 2017/00084* (2013.01); *A61B 2017/00504* (2013.01); *A61B 2017/4216* (2013.01); *A61B 2018/0063* (2013.01); *A61B 2018/00619* (2013.01); *A61B 2018/048* (2013.01); *A61B 2090/064* (2016.02)

(56) References Cited

U.S. PATENT DOCUMENTS

| | | | |
|---|---|---|---|
| 1,719,750 | A | 9/1927 | Bridge et al. |
| 3,818,913 | A | 6/1974 | Wallach |
| 3,880,168 | A | 4/1975 | Berman |
| 3,930,505 | A | 1/1976 | Wallach |
| 4,024,866 | A | 5/1977 | Wallach |
| 4,083,077 | A | 4/1978 | Knight et al. |
| 4,447,227 | A | 5/1984 | Kotsanis |
| 4,672,962 | A | 6/1987 | Hershenson |
| 4,682,596 | A | 7/1987 | Bales et al. |
| 4,748,979 | A | 6/1988 | Hershenson |
| 4,773,410 | A | 9/1988 | Blackmer et al. |
| 4,793,352 | A | 12/1988 | Eichenlaub |
| 4,872,920 | A | 10/1989 | Flynn et al. |
| 4,898,574 | A | 2/1990 | Uchiyama et al. |
| 4,915,113 | A | 4/1990 | Holman |
| 4,941,475 | A * | 7/1990 | Williams et al. ............ 600/505 |
| 4,950,266 | A | 8/1990 | Sinofsky |
| 4,985,027 | A | 1/1991 | Dressel |
| 5,006,119 | A | 4/1991 | Acker et al. |
| 5,011,566 | A | 4/1991 | Hoffman |
| 5,078,736 | A * | 1/1992 | Behl ............ 623/1.15 |
| 5,084,043 | A | 1/1992 | Hertzmann et al. |
| 5,102,410 | A | 4/1992 | Dressel |
| 5,112,328 | A | 5/1992 | Taboada et al. |
| 5,122,138 | A | 6/1992 | Manwaring |
| 5,158,536 | A | 10/1992 | Sekins et al. |
| 5,162,374 | A | 11/1992 | Mulieri et al. |
| 5,190,539 | A | 3/1993 | Fletcher et al. |
| 5,217,459 | A | 6/1993 | Kamerling |
| 5,217,465 | A | 6/1993 | Steppe |
| 5,246,436 | A | 9/1993 | Rowe |
| 5,263,951 | A | 11/1993 | Spears et al. |
| 5,277,201 | A | 1/1994 | Stern |
| 5,277,696 | A | 1/1994 | Hagen |
| 5,298,298 | A | 3/1994 | Hoffman |
| 5,306,274 | A | 4/1994 | Long |
| 5,318,014 | A | 6/1994 | Carter |
| 5,331,947 | A | 7/1994 | Shturman |
| 5,334,190 | A | 8/1994 | Seiler |
| 5,344,397 | A | 9/1994 | Heaven et al. |
| 5,348,551 | A | 9/1994 | Spears et al. |
| 5,352,512 | A | 10/1994 | Hoffman |
| 5,417,686 | A | 5/1995 | Peterson et al. |
| 5,424,620 | A | 6/1995 | Cheon et al. |
| 5,433,708 | A | 7/1995 | Nichols et al. |
| 5,433,739 | A | 7/1995 | Sluijter |
| 5,462,521 | A | 10/1995 | Brucker et al. |
| 5,500,012 | A | 3/1996 | Brucker et al. |
| 5,503,638 | A | 4/1996 | Cooper et al. |
| 5,505,730 | A | 4/1996 | Edwards |
| 5,524,620 | A | 6/1996 | Rosenschein |
| 5,529,076 | A | 6/1996 | Schachar |
| 5,542,928 | A | 8/1996 | Evans et al. |
| 5,549,628 | A | 8/1996 | Cooper et al. |
| 5,554,172 | A | 9/1996 | Horner et al. |
| 5,562,608 | A | 10/1996 | Sekins et al. |
| 5,575,803 | A | 11/1996 | Cooper et al. |
| 5,584,872 | A | 12/1996 | LaFontaine et al. |
| 5,591,157 | A | 1/1997 | Hennings et al. |
| 5,591,162 | A | 1/1997 | Fletcher et al. |
| 5,616,120 | A | 4/1997 | Andrew et al. |
| 5,620,440 | A | 4/1997 | Heckele et al. |
| 5,647,871 | A | 7/1997 | Levine et al. |
| 5,653,692 | A | 8/1997 | Masterson et al. |
| 5,662,671 | A | 9/1997 | Barbut et al. |
| 5,669,907 | A | 9/1997 | Platt, Jr. et al. |
| 5,681,282 | A | 10/1997 | Eggers et al. |
| 5,683,366 | A | 11/1997 | Eggers et al. |
| 5,688,267 | A | 11/1997 | Panescu et al. |
| 5,695,507 | A | 12/1997 | Auth et al. |
| 5,697,281 | A | 12/1997 | Eggers et al. |
| 5,697,536 | A | 12/1997 | Eggers et al. |
| 5,697,882 | A | 12/1997 | Eggers et al. |
| 5,697,909 | A | 12/1997 | Eggers et al. |
| 5,700,262 | A | 12/1997 | Acosta et al. |
| 5,707,352 | A | 1/1998 | Sekins et al. |
| 5,735,811 | A | 4/1998 | Brisken |
| 5,741,247 | A | 4/1998 | Rizoiu et al. |
| 5,741,248 | A | 4/1998 | Stern et al. |
| 5,752,965 | A | 5/1998 | Francis et al. |
| 5,754,717 | A * | 5/1998 | Esch ............ G02B 6/241 385/139 |
| 5,755,753 | A | 5/1998 | Knowlton |
| 5,769,880 | A | 6/1998 | Truckai et al. |
| 5,782,914 | A | 7/1998 | Schankereli |
| 5,785,521 | A | 7/1998 | Rizoiu et al. |
| 5,800,482 | A | 9/1998 | Pomeranz et al. |
| 5,810,764 | A | 9/1998 | Eggers et al. |
| 5,824,703 | A | 10/1998 | Clark, Jr. |
| 5,827,268 | A | 10/1998 | Laufer |
| 5,836,896 | A | 11/1998 | Rosenschein |
| 5,843,019 | A | 12/1998 | Eggers et al. |
| 5,843,073 | A | 12/1998 | Sinofsky |
| 5,871,469 | A | 2/1999 | Eggers et al. |
| 5,879,329 | A | 3/1999 | Ginsburg |
| 5,885,243 | A | 3/1999 | Capetan et al. |
| 5,888,198 | A | 3/1999 | Eggers et al. |
| 5,891,095 | A | 4/1999 | Eggers et al. |
| 5,891,134 | A | 4/1999 | Goble et al. |
| 5,911,734 | A | 6/1999 | Tsugita et al. |
| 5,913,856 | A | 6/1999 | Chia et al. |
| 5,938,660 | A | 8/1999 | Swartz et al. |
| 5,944,686 | A | 8/1999 | Patterson et al. |
| 5,944,715 | A | 8/1999 | Goble et al. |
| 5,957,919 | A | 9/1999 | Laufer |
| 5,964,752 | A | 10/1999 | Stone |
| 5,968,037 | A | 10/1999 | Rizoiu |
| 5,980,504 | A | 11/1999 | Sharkey et al. |
| 5,986,662 | A | 11/1999 | Argiro et al. |
| 5,989,212 | A | 11/1999 | Sussman et al. |
| 5,989,238 | A | 11/1999 | Ginsburg |
| 5,989,249 | A | 11/1999 | Kirwin |
| 5,989,445 | A | 11/1999 | Wise et al. |
| 5,997,499 | A | 12/1999 | Sussman et al. |
| 6,024,095 | A | 2/2000 | Stanley, III |
| 6,024,733 | A | 2/2000 | Eggers et al. |
| 6,027,501 | A | 2/2000 | Goble et al. |
| 6,032,077 | A | 2/2000 | Pomeranz |
| 6,032,674 | A | 3/2000 | Eggers et al. |
| 6,047,700 | A | 4/2000 | Eggers et al. |
| 6,053,909 | A | 4/2000 | Shadduck |
| 6,056,746 | A | 5/2000 | Goble et al. |

(56) References Cited

U.S. PATENT DOCUMENTS

| | | | |
|---|---|---|---|
| 6,059,011 A | 5/2000 | Giolo | |
| 6,063,079 A | 5/2000 | Hovda et al. | |
| 6,063,081 A | 5/2000 | Mulier et al. | |
| 6,066,134 A | 5/2000 | Eggers et al. | |
| 6,066,139 A | 5/2000 | Ryan et al. | |
| 6,074,358 A | 6/2000 | Andrew et al. | |
| 6,080,128 A | 6/2000 | Sussman et al. | |
| 6,080,151 A | 6/2000 | Swartz et al. | |
| 6,083,255 A | 7/2000 | Laufer et al. | |
| 6,095,149 A | 8/2000 | Sharkey et al. | |
| 6,099,251 A | 8/2000 | LaFleur | |
| 6,102,046 A | 8/2000 | Weinstein et al. | |
| 6,102,885 A | 8/2000 | Bass | |
| 6,106,516 A | 8/2000 | Bmassengill | |
| 6,110,162 A | 8/2000 | Sussman et al. | |
| 6,113,722 A | 9/2000 | Hoffman et al. | |
| 6,126,682 A | 10/2000 | Sharkey et al. | |
| 6,130,671 A | 10/2000 | Argiro | |
| 6,139,571 A | 10/2000 | Fuller et al. | |
| 6,149,620 A | 11/2000 | Baker et al. | |
| 6,156,036 A | 12/2000 | Sussman et al. | |
| 6,159,194 A | 12/2000 | Eggers et al. | |
| 6,162,232 A | 12/2000 | Shadduck | |
| 6,168,594 B1 | 1/2001 | LaFontaine et al. | |
| 6,174,308 B1 | 1/2001 | Goble et al. | |
| 6,179,805 B1 | 1/2001 | Sussman et al. | |
| 6,190,381 B1 | 2/2001 | Olsen et al. | |
| 6,194,066 B1 | 2/2001 | Hoffman | |
| 6,196,989 B1 | 3/2001 | Padget et al. | |
| 6,200,333 B1 | 3/2001 | Laufer | |
| 6,206,848 B1 | 3/2001 | Sussman et al. | |
| 6,210,404 B1 | 4/2001 | Shadduck | |
| 6,210,405 B1 | 4/2001 | Goble et al. | |
| 6,219,059 B1 | 4/2001 | Argiro | |
| 6,224,592 B1 | 5/2001 | Eggers et al. | |
| 6,231,567 B1 | 5/2001 | Rizoiu et al. | |
| 6,235,020 B1 | 5/2001 | Cheng et al. | |
| 6,238,391 B1 | 5/2001 | Olsen et al. | |
| 6,254,597 B1 | 7/2001 | Rizoiu et al. | |
| 6,261,286 B1 | 7/2001 | Goble et al. | |
| 6,261,311 B1 | 7/2001 | Sharkey et al. | |
| 6,264,650 B1 | 7/2001 | Hovda et al. | |
| 6,264,651 B1 | 7/2001 | Underwood et al. | |
| 6,264,654 B1 | 7/2001 | Swartz et al. | |
| 6,277,112 B1 | 8/2001 | Underwood et al. | |
| 6,283,910 B1 | 9/2001 | Bradshaw et al. | |
| 6,283,961 B1 | 9/2001 | Underwood et al. | |
| 6,283,989 B1 | 9/2001 | Laufer et al. | |
| 6,287,274 B1 | 9/2001 | Sussman et al. | |
| 6,290,715 B1 | 9/2001 | Sharkey et al. | |
| 6,296,636 B1 | 10/2001 | Cheng et al. | |
| 6,296,638 B1 | 10/2001 | Davidson et al. | |
| 6,299,633 B1 | 10/2001 | Laufer | |
| 6,300,150 B1 | 10/2001 | Venkatasubramanian | |
| 6,312,408 B1 | 11/2001 | Eggers et al. | |
| 6,312,474 B1 | 11/2001 | Francis et al. | |
| 6,315,755 B1 | 11/2001 | Sussman | |
| 6,319,222 B1 | 11/2001 | Andrew et al. | |
| 6,327,505 B1 | 12/2001 | Medhkour et al. | |
| 6,331,171 B1 | 12/2001 | Cohen | |
| 6,355,032 B1 | 3/2002 | Hovda et al. | |
| 6,361,531 B1 * | 3/2002 | Hissong | A61N 7/02 600/437 |
| 6,375,635 B2 | 4/2002 | Moutafis et al. | |
| 6,379,350 B1 | 4/2002 | Sharkey et al. | |
| 6,391,025 B1 | 5/2002 | Weinstein et al. | |
| 6,394,949 B1 | 5/2002 | Crowley et al. | |
| 6,394,996 B1 | 5/2002 | Lawrence et al. | |
| 6,398,759 B1 | 6/2002 | Sussman et al. | |
| 6,398,775 B1 | 6/2002 | Perkins et al. | |
| 6,409,723 B1 | 6/2002 | Edwards | |
| 6,416,508 B1 | 7/2002 | Eggers et al. | |
| 6,458,231 B1 | 10/2002 | Wapner et al. | |
| 6,461,350 B1 | 10/2002 | Underwood et al. | |
| 6,464,694 B1 | 10/2002 | Massengil | |
| 6,464,695 B2 | 10/2002 | Hovda et al. | |
| 6,468,270 B1 | 10/2002 | Hovda et al. | |
| 6,468,274 B1 | 10/2002 | Alleyne et al. | |
| 6,468,313 B1 | 10/2002 | Claeson et al. | |
| 6,475,215 B1 | 11/2002 | Tanrisever | |
| 6,482,201 B1 | 11/2002 | Olsen et al. | |
| 6,482,202 B1 | 11/2002 | Goble et al. | |
| 6,488,673 B1 | 12/2002 | Laufer et al. | |
| 6,493,589 B1 | 12/2002 | Medhkour et al. | |
| 6,500,173 B2 | 12/2002 | Underwood et al. | |
| 6,508,816 B2 | 1/2003 | Shadduck | |
| 6,517,533 B1 | 2/2003 | Swaminathan | |
| 6,517,568 B1 | 2/2003 | Sharkey et al. | |
| 6,522,930 B1 | 2/2003 | Schaer et al. | |
| 6,527,761 B1 | 3/2003 | Soltesz et al. | |
| 6,527,766 B1 | 3/2003 | Bair | |
| 6,540,741 B1 | 4/2003 | Underwood et al. | |
| 6,544,211 B1 | 4/2003 | Andrew et al. | |
| 6,544,248 B1 | 4/2003 | Bass | |
| 6,547,810 B1 | 4/2003 | Sharkey et al. | |
| 6,558,379 B1 | 5/2003 | Batchelor et al. | |
| 6,569,146 B1 | 5/2003 | Werner et al. | |
| 6,575,929 B2 | 6/2003 | Sussman et al. | |
| 6,575,933 B1 | 6/2003 | Wittenberger et al. | |
| 6,575,968 B1 | 6/2003 | Eggers et al. | |
| 6,579,270 B2 | 6/2003 | Sussman et al. | |
| 6,582,423 B1 | 6/2003 | Thapliyal et al. | |
| 6,585,639 B1 | 7/2003 | Kotmel et al. | |
| 6,588,613 B1 | 7/2003 | Pechenik et al. | |
| 6,589,201 B1 | 7/2003 | Sussman et al. | |
| 6,589,204 B1 | 7/2003 | Sussman et al. | |
| 6,592,594 B2 | 7/2003 | Rimbaugh et al. | |
| 6,595,990 B1 | 7/2003 | Weinstein et al. | |
| 6,599,311 B1 | 7/2003 | Biggs et al. | |
| 6,602,248 B1 | 8/2003 | Sharps et al. | |
| 6,605,087 B2 | 8/2003 | Swartz et al. | |
| 6,610,043 B1 | 8/2003 | Ingenito | |
| 6,620,130 B1 | 9/2003 | Ginsburg | |
| 6,620,155 B2 | 9/2003 | Underwood et al. | |
| 6,623,444 B2 | 9/2003 | Babaev | |
| 6,632,193 B1 | 10/2003 | Davison et al. | |
| 6,632,220 B1 | 10/2003 | Eggers et al. | |
| 6,634,363 B1 | 10/2003 | Danek et al. | |
| 6,648,847 B2 | 11/2003 | Sussman et al. | |
| 6,652,594 B2 | 11/2003 | Francis et al. | |
| 6,653,525 B2 | 11/2003 | Ingenito et al. | |
| 6,659,106 B1 | 12/2003 | Hovda et al. | |
| 6,669,685 B1 | 12/2003 | Rizoiu et al. | |
| 6,669,694 B2 | 12/2003 | Shadduck | |
| 6,676,628 B2 | 1/2004 | Sussman et al. | |
| 6,676,629 B2 | 1/2004 | Andrew et al. | |
| 6,679,264 B1 | 1/2004 | Deem et al. | |
| 6,679,879 B2 | 1/2004 | Shadduck | |
| 6,682,520 B2 | 1/2004 | Ingenito | |
| 6,682,543 B2 | 1/2004 | Barbut et al. | |
| 6,692,494 B1 | 2/2004 | Cooper et al. | |
| 6,695,839 B2 | 2/2004 | Sharkey et al. | |
| 6,699,212 B1 | 3/2004 | Kadziauskas et al. | |
| 6,699,244 B2 | 3/2004 | Carranza et al. | |
| 6,712,811 B2 | 3/2004 | Underwood et al. | |
| 6,712,812 B2 | 3/2004 | Roschak et al. | |
| 6,719,738 B2 | 4/2004 | Mehier | |
| 6,719,754 B2 | 4/2004 | Underwood et al. | |
| 6,723,064 B2 | 4/2004 | Babaev | |
| 6,726,684 B1 | 4/2004 | Woloszko et al. | |
| 6,726,708 B2 | 4/2004 | Lasheras | |
| 6,746,447 B2 | 6/2004 | Davison et al. | |
| 6,755,794 B2 | 6/2004 | Soukup | |
| 6,758,846 B2 | 7/2004 | Goble et al. | |
| 6,763,836 B2 | 7/2004 | Tasto et al. | |
| 6,764,487 B2 | 7/2004 | Mulier et al. | |
| 6,766,202 B2 | 7/2004 | Underwood et al. | |
| 6,770,070 B1 | 8/2004 | Balbierz | |
| 6,770,071 B2 | 8/2004 | Woloszko et al. | |
| 6,772,012 B2 | 8/2004 | Ricart et al. | |
| 6,776,765 B2 | 8/2004 | Soukup et al. | |
| 6,780,180 B1 | 8/2004 | Goble et al. | |
| 6,805,130 B2 | 10/2004 | Tasto et al. | |
| 6,813,520 B2 | 11/2004 | Truckai et al. | |

(56) References Cited

U.S. PATENT DOCUMENTS

| | | |
|---|---|---|
| 6,832,996 B2 | 12/2004 | Woloszko et al. |
| 6,837,884 B2 | 1/2005 | Woloszko |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,860,868 B1 | 3/2005 | Sussman et al. |
| 6,875,194 B2 | 4/2005 | MacKool |
| 6,896,674 B1 | 5/2005 | Wolosko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,918,903 B2 | 7/2005 | Bass |
| 6,921,385 B2 | 7/2005 | Clements et al. |
| 6,929,640 B1 | 8/2005 | Underwood et al. |
| 6,949,096 B2 | 9/2005 | Davison et al. |
| 6,955,675 B2 | 10/2005 | Jain |
| 6,960,182 B2 | 11/2005 | Moutafis et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Wolosko et al. |
| 7,022,088 B2 | 4/2006 | Keast et al. |
| 7,031,504 B1 | 4/2006 | Argiro et al. |
| 7,070,596 B1 * | 7/2006 | Woloszko .......... A61B 18/1482 606/41 |
| 7,083,612 B2 | 8/2006 | Littrup et al. |
| 7,094,249 B1 | 8/2006 | Broome et al. |
| 7,128,748 B2 | 10/2006 | Mooradian et al. |
| 7,136,064 B2 | 11/2006 | Zuiderveld |
| 7,144,402 B2 | 12/2006 | Kuester, III |
| 7,144,588 B2 | 12/2006 | Oray et al. |
| 7,162,303 B2 | 1/2007 | Levin et al. |
| 7,192,400 B2 | 3/2007 | Campbell et al. |
| 7,233,820 B2 | 6/2007 | Gilboa |
| 7,235,070 B2 | 6/2007 | Vanney |
| 7,311,708 B2 | 12/2007 | McClurken |
| 7,335,195 B2 | 2/2008 | Mehier |
| 7,347,859 B2 | 3/2008 | Garabedian et al. |
| 7,524,315 B2 | 4/2009 | Blott et al. |
| 7,549,987 B2 | 6/2009 | Shadduck |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,674,259 B2 | 3/2010 | Shadduck |
| 7,717,948 B2 | 5/2010 | Demarais et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,853,333 B2 | 12/2010 | Demarais |
| 7,873,417 B2 | 1/2011 | Demarais et al. |
| 7,892,229 B2 | 2/2011 | Shadduck et al. |
| 7,937,143 B2 | 5/2011 | Demarais et al. |
| 7,993,323 B2 | 8/2011 | Barry et al. |
| 8,016,823 B2 | 9/2011 | Shadduck |
| 8,131,371 B2 | 3/2012 | Demarais et al. |
| 8,131,372 B2 | 3/2012 | Levin et al. |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,269 B2 | 5/2012 | Shadduck et al. |
| 8,192,424 B2 | 6/2012 | Woloszko |
| 8,313,485 B2 | 11/2012 | Shadduck |
| 8,444,636 B2 | 5/2013 | Shadduck et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,579,893 B2 | 11/2013 | Hoey |
| 8,900,223 B2 | 12/2014 | Shadduck |
| 9,113,944 B2 | 8/2015 | Shadduck |
| 2001/0020167 A1 | 9/2001 | Woloszko et al. |
| 2001/0029370 A1 | 10/2001 | Hodva et al. |
| 2001/0037106 A1 | 11/2001 | Shadduck |
| 2002/0007180 A1 | 1/2002 | Wittenberger et al. |
| 2002/0049438 A1 | 4/2002 | Sharkey et al. |
| 2002/0077516 A1 | 6/2002 | Flanigan |
| 2002/0078956 A1 | 6/2002 | Sharpe et al. |
| 2002/0082667 A1 | 6/2002 | Shadduck |
| 2002/0095152 A1 | 7/2002 | Ciarrocca et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1 | 11/2002 | Mulier et al. |
| 2002/0193789 A1 | 12/2002 | Underwood et al. |
| 2003/0028189 A1 | 2/2003 | Woloszko et al. |
| 2003/0040742 A1 | 2/2003 | Underwood et al. |
| 2003/0097126 A1 | 5/2003 | Woloszko et al. |
| 2003/0097129 A1 | 5/2003 | Davison et al. |
| 2003/0099279 A1 | 5/2003 | Venkatasubramanian et al. |
| 2003/0109869 A1 | 6/2003 | Shadduck |
| 2003/0130655 A1 | 7/2003 | Woloszko et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0212395 A1 | 11/2003 | Woloszko et al. |
| 2003/0225364 A1 | 12/2003 | Kraft et al. |
| 2004/0024398 A1 | 2/2004 | Hovda et al. |
| 2004/0024399 A1 | 2/2004 | Sharps et al. |
| 2004/0031494 A1 | 2/2004 | Danek et al. |
| 2004/0038868 A1 | 2/2004 | Ingenito |
| 2004/0047855 A1 | 3/2004 | Ingenito |
| 2004/0049180 A1 | 3/2004 | Sharps et al. |
| 2004/0054366 A1 | 3/2004 | Davison et al. |
| 2004/0055606 A1 | 3/2004 | Hendricksen et al. |
| 2004/0068256 A1 | 4/2004 | Rizoiu et al. |
| 2004/0068308 A1 | 4/2004 | Shadduck |
| 2004/0087937 A1 | 5/2004 | Eggers et al. |
| 2004/0116922 A1 | 6/2004 | Hovda et al. |
| 2004/0193150 A1 | 9/2004 | Sharkey et al. |
| 2004/0199226 A1 | 10/2004 | Shadduck |
| 2004/0230190 A1 | 11/2004 | Dahla et al. |
| 2004/0254532 A1 | 12/2004 | Mehier |
| 2005/0004634 A1 | 1/2005 | Ricart et al. |
| 2005/0010205 A1 | 1/2005 | Hovda et al. |
| 2005/0070894 A1 | 3/2005 | McClurken |
| 2005/0119650 A1 | 6/2005 | Sanders et al. |
| 2005/0166925 A1 | 8/2005 | Wilson et al. |
| 2005/0171582 A1 | 8/2005 | Matlock |
| 2005/0187543 A1 | 8/2005 | Underwood et al. |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0267467 A1 | 12/2005 | Paul et al. |
| 2005/0267468 A1 | 12/2005 | Truckai et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0224154 A1 | 10/2006 | Shadduck et al. |
| 2006/0271111 A1 | 11/2006 | Demarais et al. |

(56) References Cited

U.S. PATENT DOCUMENTS

| | | |
|---|---|---|
| 2007/0032785 A1 | 2/2007 | Diederich et al. |
| 2007/0036417 A1 | 2/2007 | Argiro et al. |
| 2007/0091087 A1 | 4/2007 | Zuiderveld |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0265687 A1 | 11/2007 | Deem et al. |
| 2008/0033493 A1 | 2/2008 | Deckman et al. |
| 2008/0077201 A1* | 3/2008 | Levinson ............... A61B 5/411 607/96 |
| 2008/0097429 A1 | 4/2008 | McClurken |
| 2008/0103566 A1 | 5/2008 | Mehier |
| 2008/0110457 A1 | 5/2008 | Barry et al. |
| 2008/0114297 A1 | 5/2008 | Barry et al. |
| 2008/0125747 A1 | 5/2008 | Prokop |
| 2008/0132826 A1 | 6/2008 | Shadduck et al. |
| 2008/0161788 A1* | 7/2008 | Dando ............... A61B 18/1492 606/34 |
| 2008/0213331 A1 | 9/2008 | Gelfand et al. |
| 2008/0255642 A1 | 10/2008 | Zarins et al. |
| 2009/0030412 A1 | 1/2009 | Willis et al. |
| 2009/0036948 A1 | 2/2009 | Levin et al. |
| 2009/0054871 A1 | 2/2009 | Sharkey et al. |
| 2009/0062873 A1 | 3/2009 | Wu et al. |
| 2009/0076409 A1 | 3/2009 | Wu et al. |
| 2009/0105702 A1 | 4/2009 | Shadduck |
| 2009/0105703 A1 | 4/2009 | Shadduck |
| 2009/0125009 A1 | 5/2009 | Zikorus et al. |
| 2009/0149846 A1 | 6/2009 | Hoey et al. |
| 2009/0216220 A1 | 8/2009 | Hoey et al. |
| 2009/0306640 A1 | 12/2009 | Glaze et al. |
| 2009/0312753 A1 | 12/2009 | Shadduck |
| 2010/0076416 A1 | 3/2010 | Hoey et al. |
| 2010/0094270 A1 | 4/2010 | Sharma |
| 2010/0114083 A1 | 5/2010 | Sharma |
| 2010/0137860 A1 | 6/2010 | Demarais et al. |
| 2010/0137952 A1 | 6/2010 | Demarais et al. |
| 2010/0160905 A1 | 6/2010 | Shadduck |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0185189 A1 | 7/2010 | Hoey |
| 2010/0191112 A1 | 7/2010 | Demarais et al. |
| 2010/0204688 A1 | 8/2010 | Hoey et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0262133 A1 | 10/2010 | Hoey et al. |
| 2010/0268307 A1 | 10/2010 | Demarais et al. |
| 2011/0060324 A1 | 3/2011 | Wu et al. |
| 2011/0077628 A1 | 3/2011 | Hoey et al. |
| 2011/0112400 A1 | 5/2011 | Emery et al. |
| 2011/0118717 A1 | 5/2011 | Shadduck |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0208096 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143181 A1 | 6/2012 | Demarais et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0197198 A1 | 8/2012 | Demarais et al. |
| 2012/0197252 A1 | 8/2012 | Deem et al. |
| 2012/0259271 A1 | 10/2012 | Shadduck et al. |
| 2013/0079772 A1 | 3/2013 | Shadduck |
| 2013/0116683 A1 | 5/2013 | Shadduck et al. |
| 2013/0237978 A1 | 9/2013 | Shadduck et al. |
| 2014/0018890 A1 | 1/2014 | Hoey et al. |
| 2014/0031805 A1 | 1/2014 | Shadduck |

FOREIGN PATENT DOCUMENTS

| | | |
|---|---|---|
| WO | WO 2002/069821 | 9/2002 |
| WO | WO 2003/070302 | 8/2003 |
| WO | WO 2003/086498 | 10/2003 |
| WO | WO 2005/025635 | 3/2005 |
| WO | WO 2005/102175 | 11/2005 |
| WO | WO 2006/003665 | 1/2006 |
| WO | WO 2006/055695 | 5/2006 |
| WO | WO 2009/009398 | 1/2009 |

OTHER PUBLICATIONS

Fishman et al., "A randomized trial comparing lung-volume-reduction surgery with medical therapy for severe emphysema," N Engl J Med, vol. 348, No. 21, pp. 2059-2073, May 22, 2003.

Homasson, et al., "Bronchoscopic cryotherapy for airway strictures caused by tumors," Chest, vol. 90, No. 2, pp. 159-164, Aug. 1986.

Li, K., "Efficient optimal net surface detection for image segmentation—from theory to practice," M.Sc. Thesis, The University of Iowa, 2003.

Marasso, et al., "Cryosurgery in bronchosoopic treatment of tracheobronchial stenosis," Chest, vol. 103, No. 2, pp. 472-474, Feb. 1993.

Marasso, et al., "Radiofrequency resection of bronchial tumours in combination with cryotherapy: evaluation of a new technique," Thorax, vol. 53, pp. 106-109, 1998.

Mathur et al., "Fiberoptic bronchoscopic cryotherapy in the management of tracheobronchial obstruction," Chest, vol. 110, No. 3, pp. 718-723, Sep. 1996.

Morice et al. "Endobnnchial argon plasma coagulation for treatment of hemotysis and neoplastic airway obstruction," Chest, vol. 119, No. 3, pp. 781-787, Mar. 2001.

Moulding et al., "Preliminary studies for achieving transcervical oviduct occlusion by hot water or low-pressure steam," Advancesin Planned Parenthood, vol. 12, No. 2; pp. 79-85, 1977.

Quin, J., "Use of neodymium yttrium aluminum garnet laser in long-term palliation of airway obstruction," Connecticut Medicine, vol. 59, No. 7, pp. 407-412, Jul. 1995.

Sutedja, et al., "Bronchoscopic treatment of lung tumors," Elsevier Lung Cancer, 11, pp. 1-17, 1994.

Tschirren et al.; "Intrathoracic airway trees: segmentation and airway morphology analysis from low-dose CT scans;" IEEE Trans. Med. Imaging, vol. 24, No. 12; pp. 1529-1539, Dec. 2005.

Tschirren, J., "Segmentation, anatomical labeling, branchpoint matching, and quantitative analysis of human airway trees in volumetric CT images," Ph.D. Thesis, The University of Iowa, 231 pages, Aug. 2003.

Tschirren, J., "Segmentation, anatomical labeling, branchpoint matching, and quantitative analysis of human airway trees in volumetric CT images," Slides from Ph.D. defense, University of Iowa, 130 pages, Aug. 2003.

Unger, M. et al. "Monolithic Microfabricated Valves and Pumps by Multilayer Soft Lithography," Science, vol. 288, pp. 113-116, Apr. 7, 2000, accessed at http://web.mit.edu/thorsen/www/113.pdf.

(56) References Cited

OTHER PUBLICATIONS

Xia, Y. et al. "Soft Lithography," *Annu. Rev. Mater. Sci.*, vol. 28, pp. 153-184, 1998, accessed at http://www.bwfoundry.com/xia.pdf.

* cited by examiner

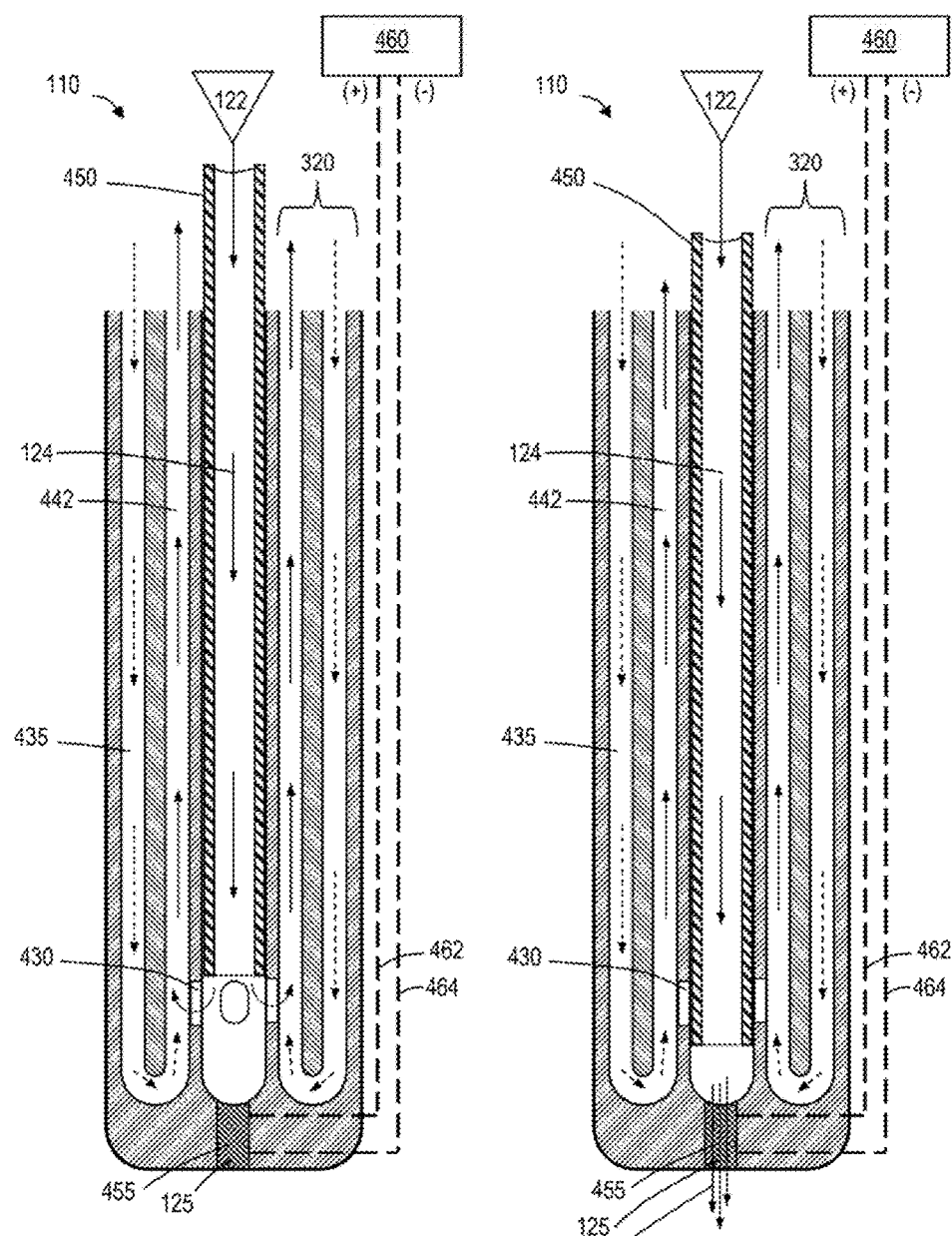

MEDICAL SYSTEM AND METHOD OF USE

CROSS-REFERENCE TO RELATED APPLICATIONS

This application is a continuation of U.S. patent application Ser. No. 12/167,155, filed Jul. 2, 2008, which is a non-provisional of U.S. Provisional Application Ser. No. 60/929,632 filed Jul. 6, 2007; U.S. application Ser. No. 12/167,155 is also a continuation-in-part of U.S. patent application Ser. No. 10/681,625 filed Oct. 7, 2003, now U.S. Pat. No. 7,674,259, titled "Medical Instruments and Techniques for Thermally-Mediated Therapies"; Ser. No. 11/158,930 filed Jun. 22, 2005, now U.S. Pat. No. 7,892,229, titled "Medical Instruments and Techniques for Treating Pulmonary Disorders"; Ser. No. 11/244,329 filed Oct. 5, 2005, now U.S. Pat. No. 8,016,823, titled "Medical Instruments and Methods of Use" and Ser. No. 11/329,381 filed Jan. 10, 2006, now U.S. Pat. No. 8,444,636, titled "Medical Instrument and Method of Use". All of the above applications are incorporated herein by this reference and made a part of this specification, together with the specifications of all other commonly-invented applications cited in the above applications.

FIELD OF THE INVENTION

This invention relates to medical instruments and systems for applying energy to tissue, and more particularly relates to a system for ablating, sealing, welding, coagulating, shrinking or creating lesions in tissue by means of contacting a targeted site in a patient with a vapor phase media wherein a subsequent vapor-to-liquid phase change of the media applies thermal energy to the tissue to cause an intended therapeutic effect. Variations of the invention include devices and methods for monitoring the vapor flow for various parameters with one or more sensors. In yet additional variations, the invention includes devices and methods for modulating parameters of the system in response to the observed parameters.

BACKGROUND OF THE INVENTION

Various types of medical instruments utilizing radiofrequency (Rf) energy, laser energy, microwave energy and the like have been developed for delivering thermal energy to tissue, for example to ablate tissue. While such prior art forms of energy delivery work well for some applications, Rf, laser and microwave energy typically cannot cause highly "controlled" and "localized" thermal effects that are desirable in controlled ablation soft tissue for ablative a controlled depth or for the creation of precise lesions in such tissue. In general, the non-linear or non-uniform characteristics of tissue affect electromagnetic energy distributions in tissue.

There remains a need for systems and methods that controllably apply thermal energy in a controlled and localized manner without the lack of control often associated when Rf, laser and microwave energy are applied directly to tissue.

SUMMARY OF THE INVENTION

The present invention is adapted to provide improved methods of controlled thermal energy delivery to localized tissue volumes, for example for ablating, sealing, coagulating or otherwise damaging targeted tissue, for example to ablate a lesion interstitially or to ablate the lining of a body cavity. Of particular interest, the method causes thermal effects in targeted tissue without the use of Rf current flow through the patient's body and without the potential of carbonizing tissue.

In general, the thermally-mediated treatment method comprises causing, a vapor-to-liquid phase state change in a selected media at a targeted tissue site thereby applying thermal energy substantially equal to the heat of vaporization of the selected media to the tissue site. The thermally-mediated therapy can be delivered to tissue by such vapor-to-liquid phase transitions, or "internal energy" releases, about the working surfaces of several types of instruments for ablative treatments of soft tissue. FIGS. 1A and 1B illustrate the phenomena of phase transitional releases of internal energies. Such internal energy involves energy on the molecular and atomic scale—and in polyatomic gases is directly related to intermolecular attractive forces, as well as rotational and vibrational kinetic energy. In other words, the method of the invention exploits the phenomenon of internal energy transitions between gaseous and liquid phases that involve very large amounts of energy compared to specific heat.

It has been found that the controlled application of such energy in a controlled media-tissue interaction solves many of the vexing problems associated with energy-tissue interactions in Rf, laser and ultrasound modalities. The apparatus of the invention provides a vaporization chamber in the interior of an instrument, in a source remote from the instrument and/or in an instrument working end. A source provides liquid media to the interior vaporization chamber wherein energy is applied to create a selected volume of vapor media. In the process of the liquid-to-vapor phase transition of a liquid media, for example water, large amounts of energy are added to overcome the cohesive forces between molecules in the liquid, and an additional amount of energy is required to expand the liquid 1000+ percent (P$\Delta$D) into a resulting vapor phase (see FIG. 1A). Conversely, in the vapor-to-liquid transition, such energy will be released at the phase transition at the interface with the targeted tissue site. That is, the heat of vaporization is released at the interface when the media transitions from gaseous phase to liquid phase wherein the random, disordered motion of molecules in the vapor regain cohesion to convert to a liquid media. This release of energy (defined as the capacity for doing work) relating to intermolecular attractive forces is transformed into therapeutic heat for a thermotherapy at the interface with the targeted body structure. Heat flow and work are both ways of transferring energy.

In FIG. 1A, the simplified visualization of internal energy is useful for understanding phase transition phenomena that involve internal energy transitions between liquid and vapor phases. If heat were added at a constant rate in FIG. 1A (graphically represented as 5 calories/gm blocks) to elevate the temperature of water through its phase change to a vapor phase, the additional energy required to achieve the phase change (latent heat of vaporization) is represented by the large number of 110+ blocks of energy at 100° C. In FIG. 1A. Still referring to FIG. 1A, it can be easily understood that all other prior art ablation modalities—Rf, laser, microwave and ultrasound—create energy densities by simply ramping up calories/gm as indicated by the temperature range from 37° C. through 100° C. as in FIG. 1A. The prior art modalities make no use of the phenomenon of phase transition energies as depicted in FIG. 1A.

FIG. 1B graphically represents a block diagram relating to energy delivery aspects of the present invention. The system provides for insulative containment of an initial primary energy-media interaction within an interior vaporization chamber of medical thermotherapy system. The initial, ascendant energy-media interaction delivers energy sufficient to achieve the heat of vaporization of a selected liquid media, such as water or saline solution, within an interior of the system. This aspect of the technology requires a highly controlled energy source wherein a computer controller may need to modulated energy application between very large energy densities to initially surpass the latent heat of vaporization with some energy sources (e.g. a resistive heat source, an Rf energy source, a light energy source, a microwave energy source, an ultrasound source and/or an inductive heat source) and potential subsequent lesser energy densities for maintaining a high vapor quality. Additionally, controller must control the pressure of liquid flows for replenishing the selected liquid media at the required rate and optionally for controlling propagation velocity of the vapor phase media from the working end surface of the instrument. In use, the method of the invention comprises the controlled application of energy to achieve the heat of vaporization as in FIG. 1A and the controlled vapor-to-liquid phase transition and vapor exit pressure to thereby control the interaction of a selected volume of vapor at the interface with tissue. The vapor-to-liquid phase transition can deposit 400, 500, 600 or more cal/gram within the targeted tissue site to perform the thermal ablation with the vapor in typical pressures and temperatures.

In one variation, the present disclosure includes medical systems for applying thermal energy to tissue, where the system comprises an elongated probe with an axis having an interior flow channel extending to at least one outlet in a probe working end; a source of vapor media configured to provide a vapor flow through at least a portion of the interior flow channel, wherein the vapor has a minimum temperature of; and at least one sensor in the flow channel for providing a signal of at least one flow parameter selected from the group one of (i) existence of a flow of the vapor media, (ii) quantification of a flow rate of the vapor media, and (iii) quality of the flow of the vapor media. The medical system can include variations where the minimum temperature varies from at least 80° C. 100° C. 120° C. 140° C. and 160° C. However, other temperature ranges can be included depending upon the desired application Sensors included in the above system include temperature sensor, an impedance sensor, a pressure sensor as well as an optical sensor.

In many variations, the devices and method described herein will include a visualization element placed within or adjacent to the treatment area. In many cases, the visualization element shall be coupled to a treatment device (either by being placed within the device or otherwise attached to the device. Any number of visualization elements can be incorporated with the methods and devices described herein. For example, a visualization element can include an optic fiber advanced within or adjacent to the device, a CCD camera affixed to the device or other visualization means as commonly used in remote visualization applications. The visualization element can provide imaging before, during, and/or after the controlled flow egresses from the device. In addition, the visualization element can include thermal imaging capabilities to monitor the vapor flow from the device or the treatment effect in tissue.

The source of vapor media can include a pressurized source of a liquid media and an energy source for phase conversion of the liquid media to a vapor media. In addition, the medical system can further include a controller capable of modulating a vapor parameter in response to a signal of a flow parameter; the vapor parameter selected from the group of (i) flow rate of pressurized source of liquid media, (ii) inflow pressure of the pressurized source of liquid media, (iii) temperature of the liquid media, (iv) energy applied from the energy source to the liquid media, (v) flow rate of vapor media in the flow channel, (vi) pressure of the vapor media in the flow channel, (vi) temperature of the vapor media, and (vii) quality of vapor media.

In another variation, a novel medical system for applying thermal energy to tissue comprises an elongated probe with an axis having an interior flow channel extending to at least one outlet in a probe working end, wherein a wall of the flow channel includes an insulative portion having a thermal conductivity of less than a maximum thermal conductivity; and a source of vapor media configured to provide a vapor flow through at least a portion of the interior flow channel, wherein the vapor has a minimum temperature Variations of such systems include systems where the maximum thermal conductivity ranges from 0.05 W/mK, 0.01 W/mK and 0.005 W/mK.

Another variation of a novel medical system for delivering energy to tissue comprises an elongated probe with a flow channel extending from a proximal portion of the probe to at least one flow outlet in an expandable working end; a source of a vapor flow in communication with the flow channel; and a recirculation channel having a distal end communicating with the working end.

The present disclosure also includes methods for applying energy to mammalian body structure, comprising providing an elongated probe with a distal working end and providing a pressure sensing mechanism for measuring pressure within at least one of the probe and the body structure; providing a flow of a non-ionized flow media from at least one port in the working end thereby applying energy to the body structure; and adjusting the pressure of the flow of the non-ionized flow media from the at least one port in response to a measured change in pressure by the pressure sensing mechanism.

In an additional variation, the inventive methods include a method of providing a therapeutic effect in a mammalian subject comprising providing a vapor source comprising a pressure source configured for providing a flow of liquid media from a liquid media source into a vaporization chamber having a heating mechanism; actuating the pump to provide the liquid into the vaporization chamber; applying energy from the heating mechanism to convert a substantially water media into a minimum water vapor; and introducing said vapor into an interface with tissue to cause the intended effect. While any range of water vapor can be included within the scope of this invention, variations include a minimum water vapor can range from 60% water vapor, 70% water vapor, 80% water vapor and 90% water vapor.

One embodiment of the invention comprises a system and method for delivering ablative energy to a body lumen or cavity, for example in an endometrial ablation procedure. One embodiment comprises an elongated probe with an insulated rigid or flexible shaft with a distal working end and a source of a vapor media that can be ejected from at least one outlet in the working end. The introduction and condensation of the vapor media is utilized to apply a selected level of thermal energy to ablate a surface portion of the body cavity. The method includes providing a vapor media capable of releasing the heat of vaporization, in one example, for global endometrial ablation. The method includes introducing the vapor media at a flow rate of ranging from 0.001 to 20 ml/min, 0.010 to 10 ml/min, 0.050 to 5 ml/min., at an inflow pressure ranging from 0.5 to 1000 psi, 5 to 500 psi, and 25 to 200 psi. The method includes applying the selected level of thermal energy over an interval ranging from 0.1 to 600 seconds; 0.5 to 300 seconds, and 1 to 180 seconds. Further, the application of energy may be pulsed as a suitable pulse rate. The system and method further include providing a controller for controlling the pressure in a body cavity, such as a uterine cavity.

The systems and probes of the invention are configured for controlled application of the heat of vaporization of a vapor-to liquid phase transition in an interface with tissue for tissue ablation, tissue sealing, tissue welding, and causing an immune response. In general, the instrument and method of the invention cause thermal ablations rapidly, efficiently and uniformly over a tissue interface.

The instrument and method of the invention generate vapor phase media that is controllable as to volume and ejection pressure to provide a not-to-exceed temperature level that prevents desiccation, eschar, smoke and tissue sticking.

The instrument and method of the invention cause an energy-tissue interaction that is imageable with intra-operative ultrasound or MRI.

The instrument and method of the invention cause thermal effects in tissue that do not rely applying an electrical field across the tissue to be treated.

Additional advantages of the invention will be apparent from the following description, the accompanying drawings and the appended claims.

All patents, patent applications and publications mentioned in this specification are herein incorporated by reference to the same extent as if each individual publication or patent application was specifically and individually indicated to be incorporated by reference.

In addition, it is intended that combinations of aspects of the systems and methods described herein as well as the various embodiments themselves, where possible, are within the scope of this disclosure.

BRIEF DESCRIPTION OF THE DRAWINGS

FIG. 15E is a view of another vapor delivery probe similar to FIG. 15D with a mechanical valve system in a first position.

FIG. 15F is a view of the probe of FIG. 15E with the mechanical valve system in a second position.

DETAILED DESCRIPTION OF THE INVENTION

As used in the specification, "a" or "an" means one or more. As used in the claim(s), when used in conjunction with the word "comprising", the words "a" or "an" mean one or more. As used herein, "another" means as least a second or more. "Substantially" or "substantial" mean largely but not entirely. For example, substantially may mean about 10% to about 99.999, about 25% to about 99.999% or about 50% to about 99.999%.

Treatment Media Source, Energy Source, Controller

Figure 2:
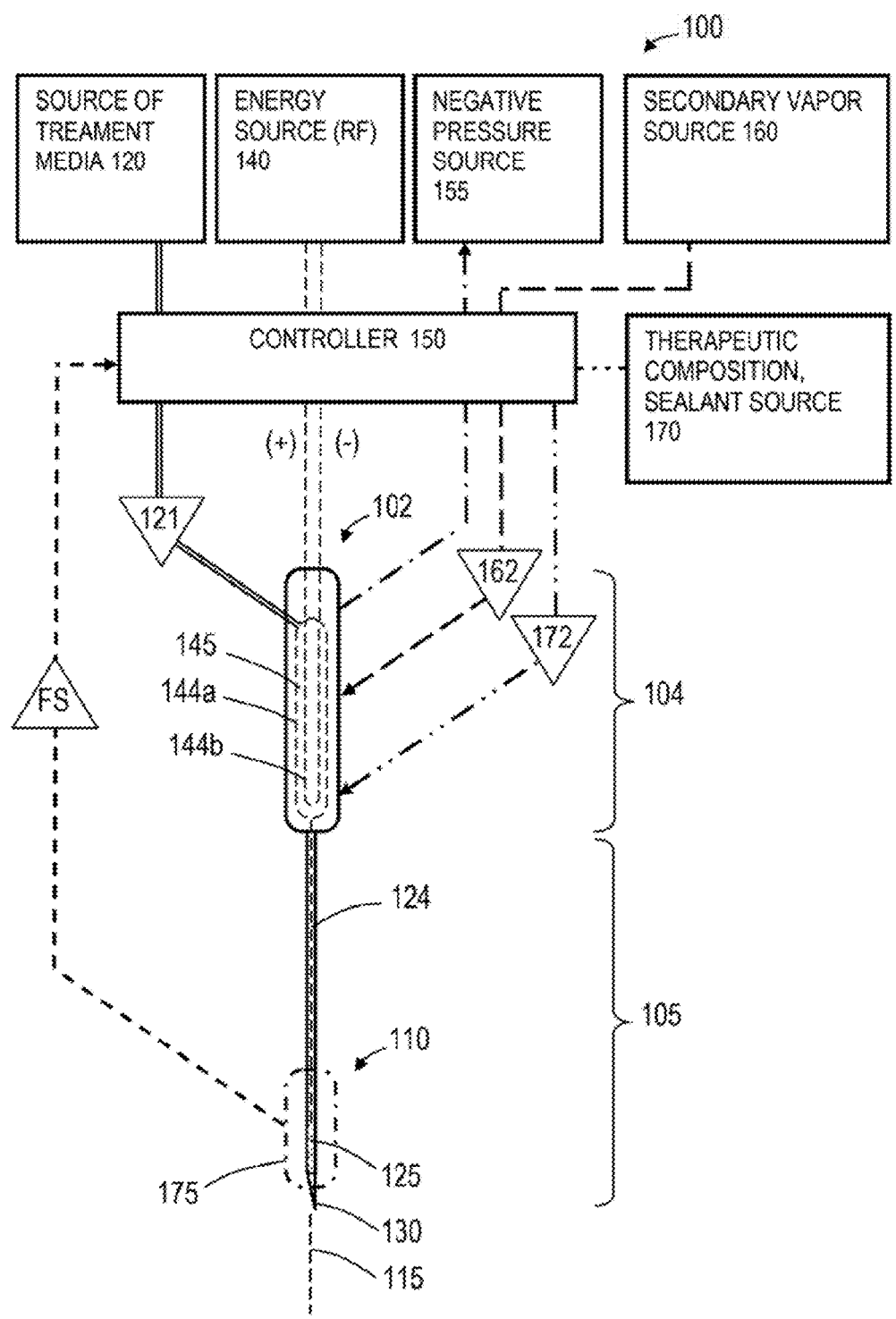
FIG. 2 is a schematic view of an exemplary medical system.

Referring to FIG. 2, a schematic view of medical system 100 of the present invention is shown that is adapted for treating a tissue target, wherein the treatment comprises an ablation or thermotherapy and the tissue target can comprise any mammalian soft tissue to be ablated, sealed, contracted, coagulated, damaged or treated to elicit an immune response. The system 100 include an instrument or probe body 102 with a proximal handle end 104 and an extension portion 105 having a distal or working end indicated at 110. In one embodiment depicted in FIG. 2, the handle end 104 and extension portion 105 generally extend about longitudinal axis 115. In the embodiment of FIG. 2, the extension portion 105 is a substantially rigid tubular member with at least one flow channel therein, but the scope of the invention encompasses extension portions 105 of any mean diameter and any axial length, rigid or flexible, suited for treating a particular tissue target. In one embodiment, a rigid extension portion 105 can comprise a 20 Ga. to 40 Ga. needle with a short length for thermal treatment of a patient's cornea or a somewhat longer length for treating a patient's retina. In another embodiment, an elongate extension portion 105 can comprise a single needle or a plurality of needles having suitable lengths for tumor or lesion ablation in a liver, breast, gall bladder, bone and the like. In another embodiment, an elongate extension portion 105 can comprise a flexible catheter for introduction through a body lumen to access at tissue target, with a diameter ranging from about 1 to 10 mm. In another embodiment, the extension portion 105 or working end 110 can be articulatable, deflectable or deformable. The probe handle end 104 can be configured as a hand-held member, or can be configured for coupling to a robotic surgical system. In another embodiment, the working end 110 carries an openable and closeable structure for capturing tissue between first and second tissue-engaging surfaces (not shown), which can comprise actuatable components such as one or more clamps, jaws, loops, snares and the like. The proximal handle end 104 of the probe can carry various actuator mechanisms known in the art for actuating components of the system 100, and/or one or more foot-switches can be used for actuating components of the system.

As can be seen in FIG. 2, the system 100 further includes a source 120 of a flowable liquid treatment media 121 that communicates with a flow channel 124 extending through the probe body 102 to at least one outlet 125 in the working end 110. The outlet 125 can be singular or multiple and have any suitable dimension and orientation as will be described further below. The distal tip 130 of the probe can be sharp for penetrating tissue, or can be blunt-tipped or open-ended with outlet 125.

In one embodiment shown in FIG. 2, an RF energy source 140 is operatively connected to a thermal energy source or emitter (e.g., opposing polarity electrodes 144a, 144b) in interior chamber 145 in the proximal handle end 104 of the probe for converting the liquid treatment media 121 from a liquid phase media to a non-liquid vapor phase media 122 with a heat of vaporization in the range of 60° C. to 200° C., or 80° C. to 120° C. A vaporization system using Rf energy and opposing polarity electrodes is disclosed in co-pending U.S. patent application Ser. No. 11/329,381 which is incorporated herein by reference. Another embodiment of vapor generation system is described in detail below in the Section titled "REMOTE VAPOR GENERATION UNIT AND CONTROL SYSTEMS". In any system embodiment, for example in the system of FIG. 2, a controller 150 is provided that comprises a computer control system configured for controlling the operating parameters of inflows of liquid treatment media source 120 and energy applied to the liquid media by an energy source to cause the liquid-to-vapor conversion. The vapor generation systems described herein can consistently produce a high quality vapor having a temperature of at least 80° C., 100° C. 120° C., 140° C. and 160° C.

As can be seen in FIG. 2, the medical system 100 can further include a negative pressure or aspiration source indicated at 155 that is in fluid communication with a flow channel in probe 102 and working end 110 for aspirating treatment vapor media 122, body fluids, ablation by-products, tissue debris and the like from a targeted treatment site, as will be further described below. In FIG. 2, the controller 150 also is capable of modulating the operating parameters of the negative pressure source 155 to extract vapor media 122 from the treatment site or from the interior of the working end 110 by means of a recirculation channel to control flows of vapor media 122 as will be described further below.

In another embodiment, still referring, to FIG. 2, medical system 100 further includes secondary media source 160 for providing, an inflow of a second media, for example a biocompatible gas such as $CO_2$. In one method, a second media that includes at least one of depressurized $CO_2$, $N_2$, $O_2$ or $H_2O$ can be introduced and combined with the vapor media 122. This second media 162 is introduced into the flow of non-ionized vapor media for lowering the mass average temperature of the combined flow for treating tissue. In another embodiment, the medical system 100 includes a source 170 of a therapeutic or pharmacological agent or a sealant composition indicated at 172 for providing an additional treatment effect in the target tissue. In FIG. 2, the controller indicated at 150 also is configured to modulate the operating parameters of source 160 and 170 to control inflows of a secondary vapor 162 and therapeutic agents, sealants or other compositions indicated at 172.

In FIG. 2, it is further illustrated that a sensor system 175 is carried within the probe 102 for monitoring a parameter of the vapor media 122 to thereby provide a feedback signal FS to the controller 150 by means of feedback circuitry to thereby allow the controller to modulate the output or operating parameters of treatment media source 120, energy source 140, negative pressure source 155, secondary media source 160 and therapeutic agent source 170. The sensor system 175 is further described below, and in one embodiment comprises a flow sensor to determine flows or the lack of a vapor flow. In another embodiment, the sensor system 175 includes a temperature sensor. In another embodiment, sensor system 175 includes a pressure sensor. In another embodiment, the sensor system 175 includes a sensor arrangement for determining the quality of the vapor media, e.g., in terms or vapor saturation or the like. The sensor systems will be described in more detail below.

Figure 3:
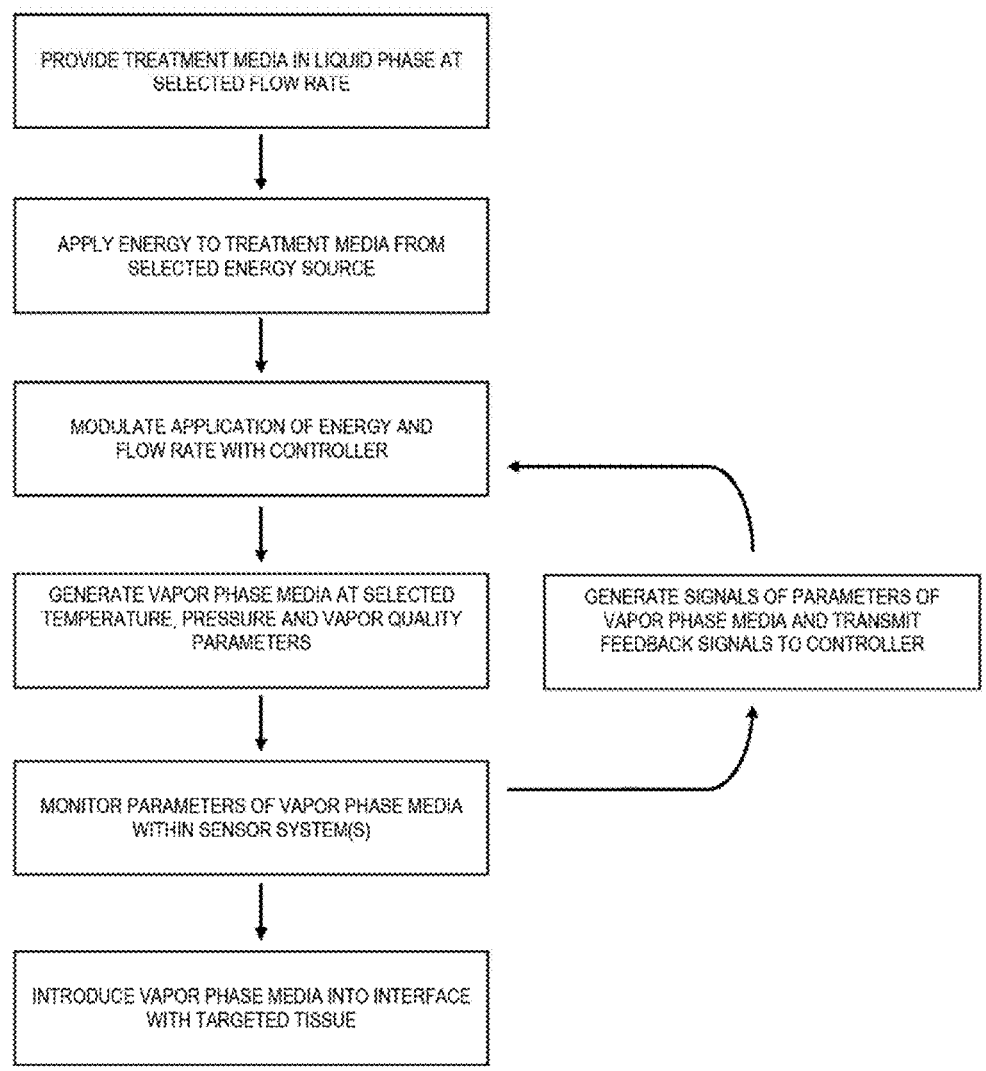
FIG. 3 is a block diagram of a control method of the invention.

Now turning to FIGS. 2 and 3, the controller 150 is capable of all operational parameters of system 100, including modulating the operational parameters in response to preset values or in response to feedback signals FS from sensor system(s) 175 within the system 100 and probe working end 110. In one embodiment, as depicted in the block diagram of FIG. 3, the system 100 and controller 150 are capable of providing or modulating an operational parameter comprising a flow rate of liquid phase treatment media 122 from pressurized source 120, wherein the flow rate is within a range from about 0.001 to 20 ml/min, 0.010 to 10 ml/min or 0.050 to 5 ml/min. The system 100 and controller 150 are further capable of providing or modulating another operational parameter comprising the inflow pressure of liquid phase treatment media 121 in a range from 0.5 to 1000 psi, 5 to 500 psi, or 2.5 to 200 psi. The system 100 and controller 150 are further capable of providing or modulating another operational parameter comprising a selected level of energy capable of converting the liquid phase media into a non-liquid, non-ionized gas phase media, wherein the energy level is within a range of about 5 to 2,500 watts; 10 to 1,000 watts or 25 to 500 watts. The system 100 and controller 150 are capable of applying the selected level of energy to provide the phase conversion in the treatment media over an interval ranging from 0.1 second to 10 minutes; 0.5 seconds to 5 minutes, and 1 second to 60 seconds. The system 100 and controller 150 are further capable of controlling parameters of the vapor phase media including the flow rate of non-ionized vapor media proximate an outlet 125, the pressure of non-ionized vapor media at the outlet, the temperature or mass average temperature of the vapor media, and the quality of non-ionized vapor media as will be described further below.

Figure 4A:
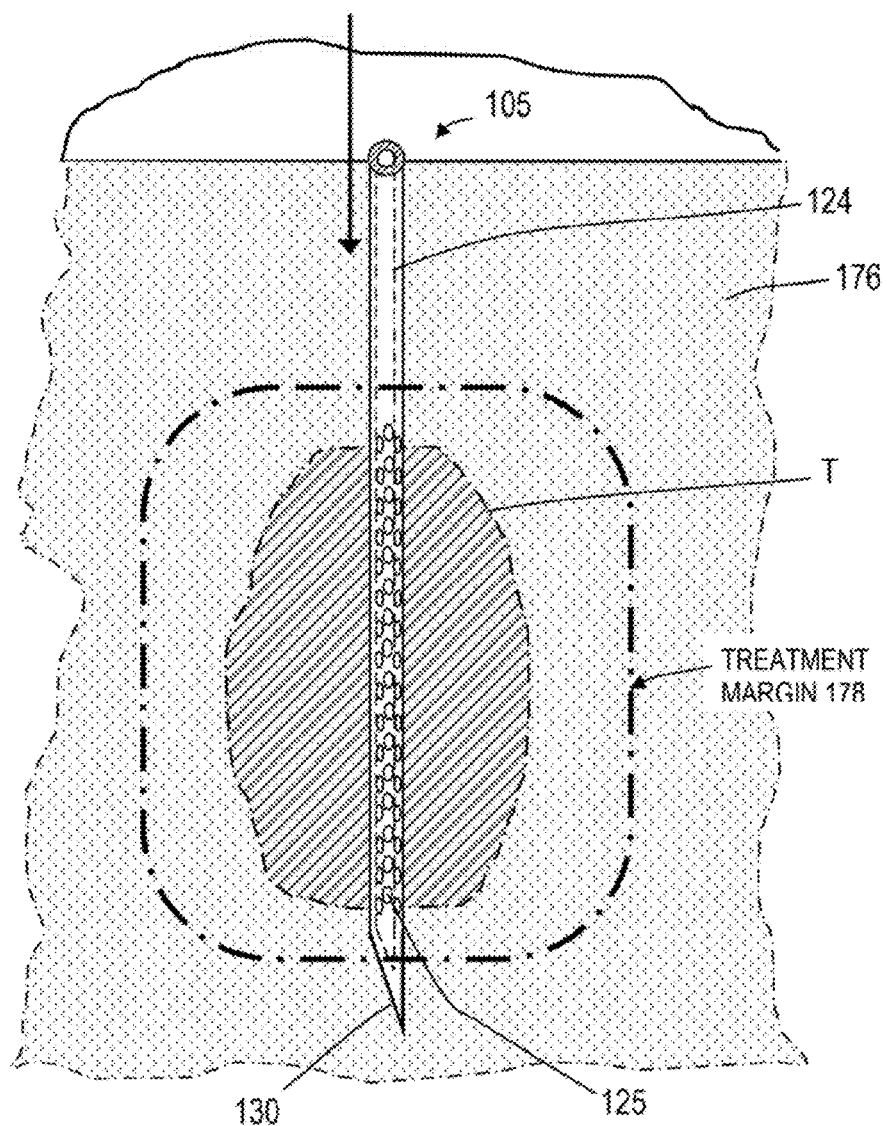
FIG. 4A is an illustration of the working end of FIG. 2 being introduced into soft tissue to treat a targeted tissue volume.
Figure 4B:
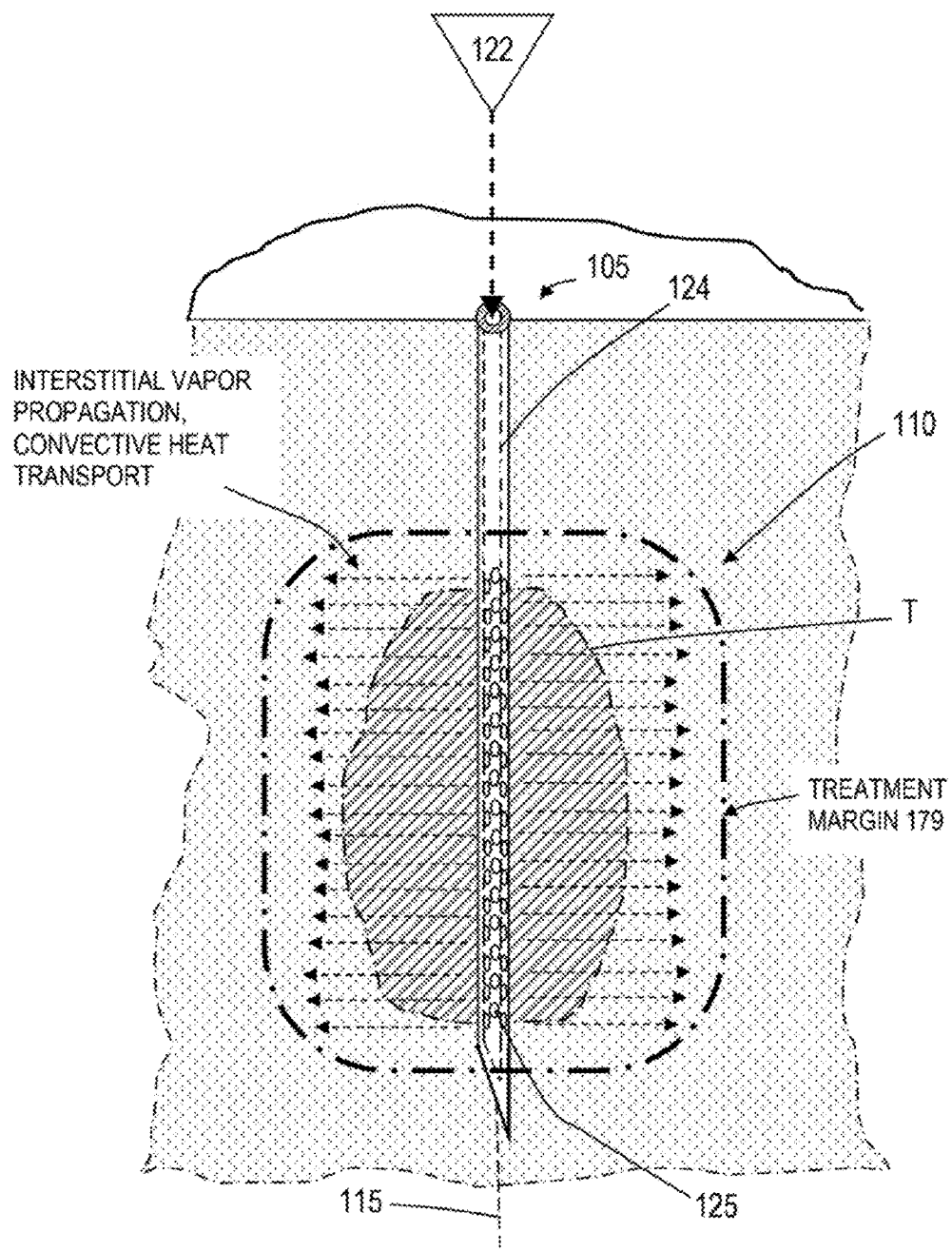
FIG. 4B is an illustration of the working end of FIG. 4A showing the propagation of vapor media in tissue in a method of use in ablating a tumor.

FIGS. 4A and 4B illustrate a working end 110 of the system 100 of FIG. 2 and a method of use. As can be seen in FIG. 4A, a working end 110 is singular and configured as a needle-like device for penetrating into and/or through a targeted tissue T such as a tumor in a tissue volume 176. The tumor can be benign or malignant tissue, for example, in a patient's breast, uterus, lung, liver, kidney, gall bladder, stomach, pancreas, colon, GI tract, bladder, prostate, bone, vertebra, eye, brain or other tissue. In one embodiment of the invention, the extension portion 104 is made of a metal, for example, stainless steel. Alternatively or additionally, at least some portions of the extension portion can be fabricated of a polymer material such as PEEK, PTFE, Nylon or polypropylene. Also optionally, one or more components of the extension portion are formed of coated metal, for example, a coating with Teflon® to reduce friction upon insertion and to prevent tissue sticking following use. In one embodiment at in FIG. 4A, the working end 110 includes a plurality of outlets 125 that allow vapor media to be elected in all radial directions over a selected treatment length of the working end.

Figure 5:
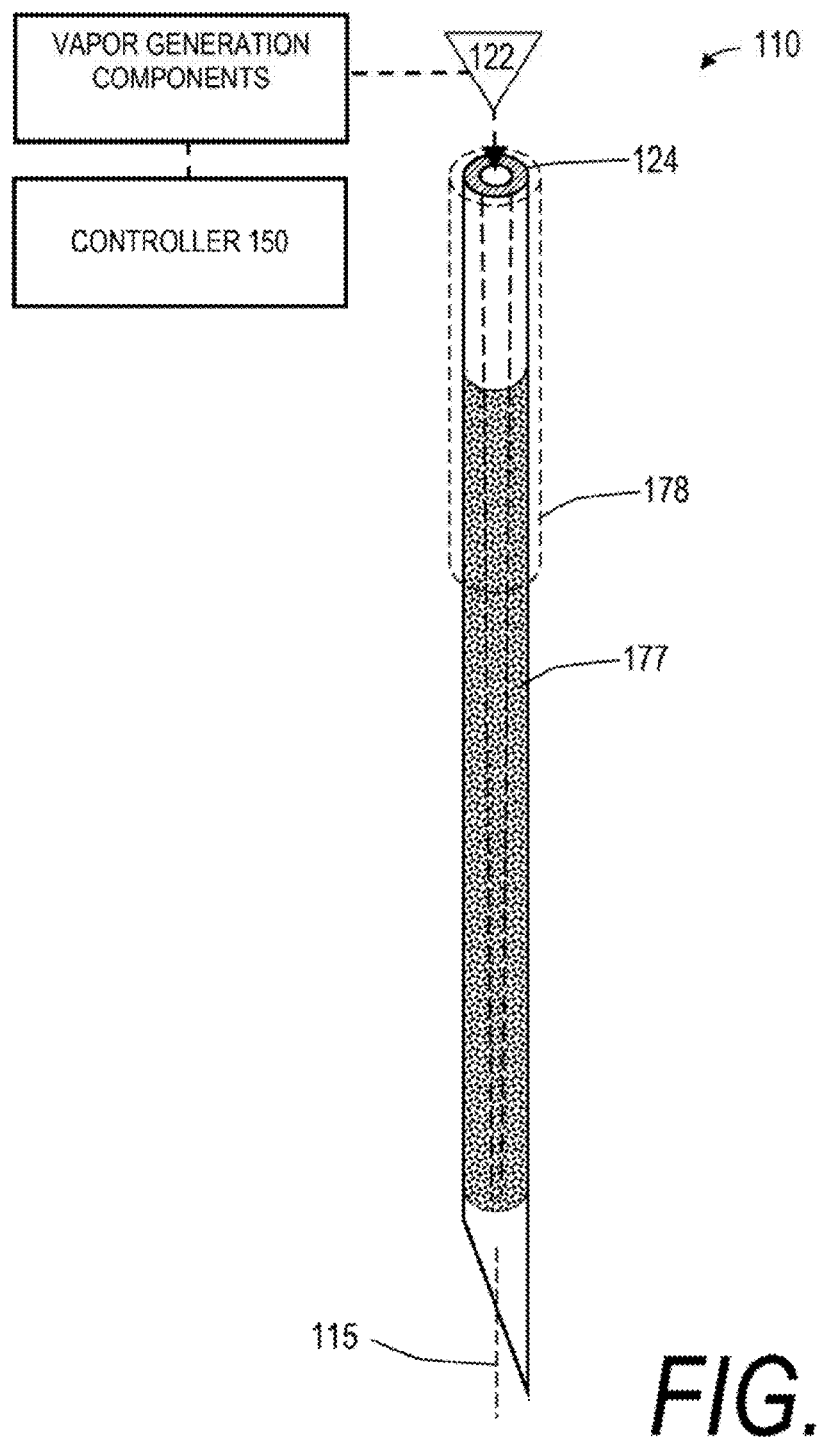
FIG. 5 is an illustration of a working end similar to FIGS. 4A-4B with vapor outlets comprising microporosities in a porous wall.

In one embodiment, the outer diameter of extension portion 105 or working end 110 is, for example, 0.2 mm, 0.5 mm, 1 mm, 2 mm, 5 mm or an intermediate, smaller or larger diameter. Optionally, the outlets can comprise microporosities 177 in a porous material as illustrated in FIG. 5 for diffusion and distribution of vapor media flows about the surface of the working end. In one such embodiment, such porosities provide a greater restriction to vapor media outflows than adjacent targeted tissue which can vary greatly in vapor permeability. In this case, such microporosities insure that vapor media outflows will occur substantially uniformly over the surface of the working end. Optionally, the wall thickness of the working end 110 is from 0.05 to 0.5 mm. Optionally, the wall thickness decreases or increases towards the distal sharp tip 130 (FIG. 5). In one embodiment, the dimensions and orientations of outlets 125 are selected to diffuse and/or direct vapor media propagation into targeted tissue T and more particularly to direct vapor media into all targeted tissue to cause extracellular vapor propagation and thus convective heating of the target tissue as indicated in FIG. 4B. As shown in FIGS. 4A-4B, the shape of the outlets 125 can vary, for example, round, ellipsoid, rectangular, radially and/or axially symmetric or asymmetric. As shown in FIG. 5, a sleeve 178 can be advanced or retracted relative to the outlets 125 to provide a selected exposure of such outlets to provide vapor injection over a selected length of the working end 110. Optionally, the outlets can be oriented in various ways, for example so that vapor media 122 is ejected perpendicular to a surface of working end 110, or ejected is at an angle relative to the axis 115 or angled relative to a plane perpendicular to the axis. Optionally, the outlets can be disposed on a selected side or within a selected axial portion of working end, wherein rotation or axial movement of the working end will direct vapor propagation and energy delivery in a selected direction. In another embodiment, the working end 110 can be disposed in a secondary outer sleeve that has apertures in a particular side thereof for angular/axial movement in targeted tissue for directing vapor flows into the tissue.

FIG. 4B illustrates the working end 110 of system 100 ejecting vapor media from the working end under selected operating parameters, for example a selected pressure, vapor temperature, vapor quantity, vapor quality and duration of flow. The duration of flow can be a selected pre-set or the hyperechoic aspect of the vapor flow can be imaged by means of ultrasound to allow the termination of vapor flows by observation of the vapor plume relative to targeted tissue T. As depicted schematically in FIG. 4B, the vapor can propagate extracellularly in soft tissue to provide intense convective heating as the vapor collapses into water droplets which results in effective tissue ablation and cell death. As further depicted in FIG. 4B, the tissue is treated to provide an effective treatment margin 179 around a targeted tumorous volume. The vapor delivery step is continuous or can be repeated at a high repetition rate to cause a pulsed form of convective heating and thermal energy delivery to the targeted tissue. The repetition rate vapor flows can vary, for example with flow durations intervals from 0.01 to 20 seconds and intermediate off intervals from 0.01 to 5 seconds or intermediate, larger or smaller intervals.

In an exemplary embodiment as shown in FIGS. 4A-4B, the extension portion 105 can be a unitary member such as a needle. In another embodiment, the extension portion 105 or working end 110 can be a detachable flexible body or rigid body, for example of any type selected by a user with outlet sizes and orientations for a particular procedure with the working end attached by threads or Luer fitting to a more proximal portion of probe 102.

Figure 6A:
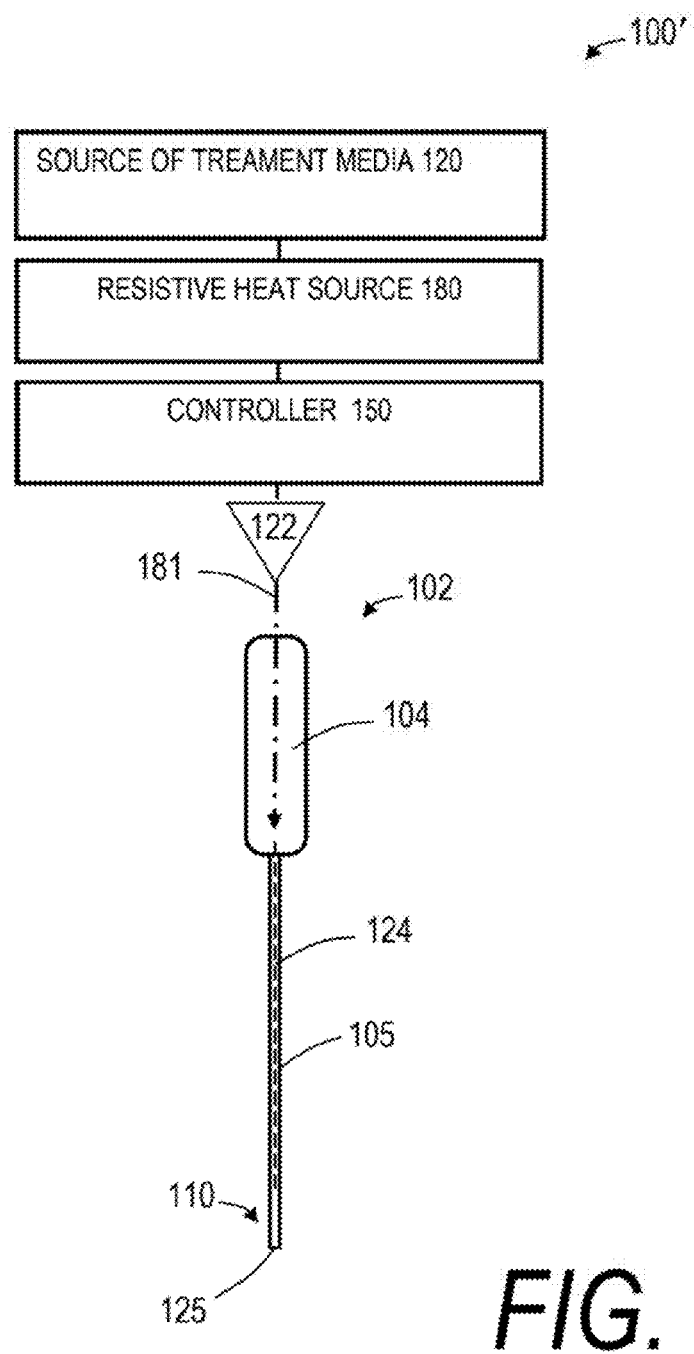
FIG. 6A is another system embodiment with a vapor generator comprising a resistive heating mechanism remote from the probe handle and the needle-like working end.
Figure 6B:
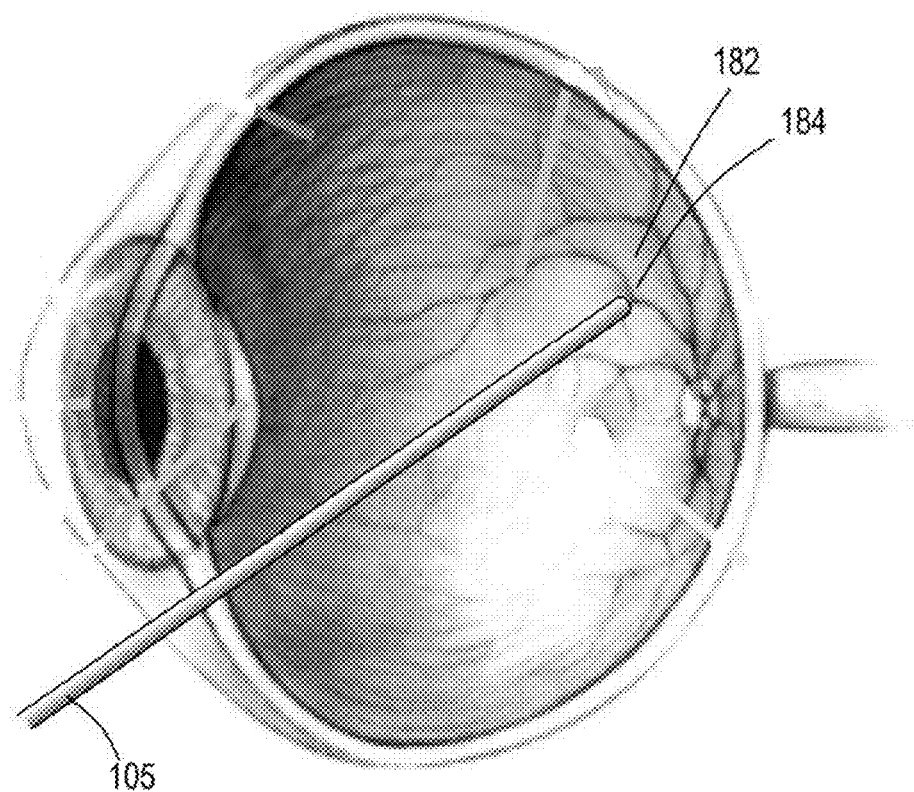
FIG. 6B is an illustration of the working end of FIG. 6A treating retinal tissue.

FIG. 6A illustrates another similar medical system 100' wherein the source 120 of a flowable liquid treatment media communicates with an energy source 180 comprising a resistive heating system that can be a modular unit and can be remote from the proximal handle end 104 of probe body 102, or the resistive can be within the handle portion or within the extension member 105, or a combination of locations. Thus in one embodiment, the conversion of a liquid media 121 to a vapor media 122 can be accomplished by a resistive heating system and the vapor media can flow through an insulated conduit 181 to communicate with flow channel 124 and then exit the probe 102 at an outlet 125 in the working end 110. The controller 150 again is operatively coupled to all the system sources, sensors and component to control all operational parameters for treating a tissue target. As depicted in FIG. 6B, one embodiment comprised a probe with extension member 105 that comprises a needle member with a blunt or sharp tip for penetration through the sclera or cornea to treat retinal tissue 182, for example to ablate and coagulate blood vessels 184 in a treatment of certain types of macular degeneration. The method can be accompanied by a penetrating endoscope or a slit lamp can be used to localize the treatment.

Sensor Systems for Flows, Temperature, Pressure, Quality

Figure 7:
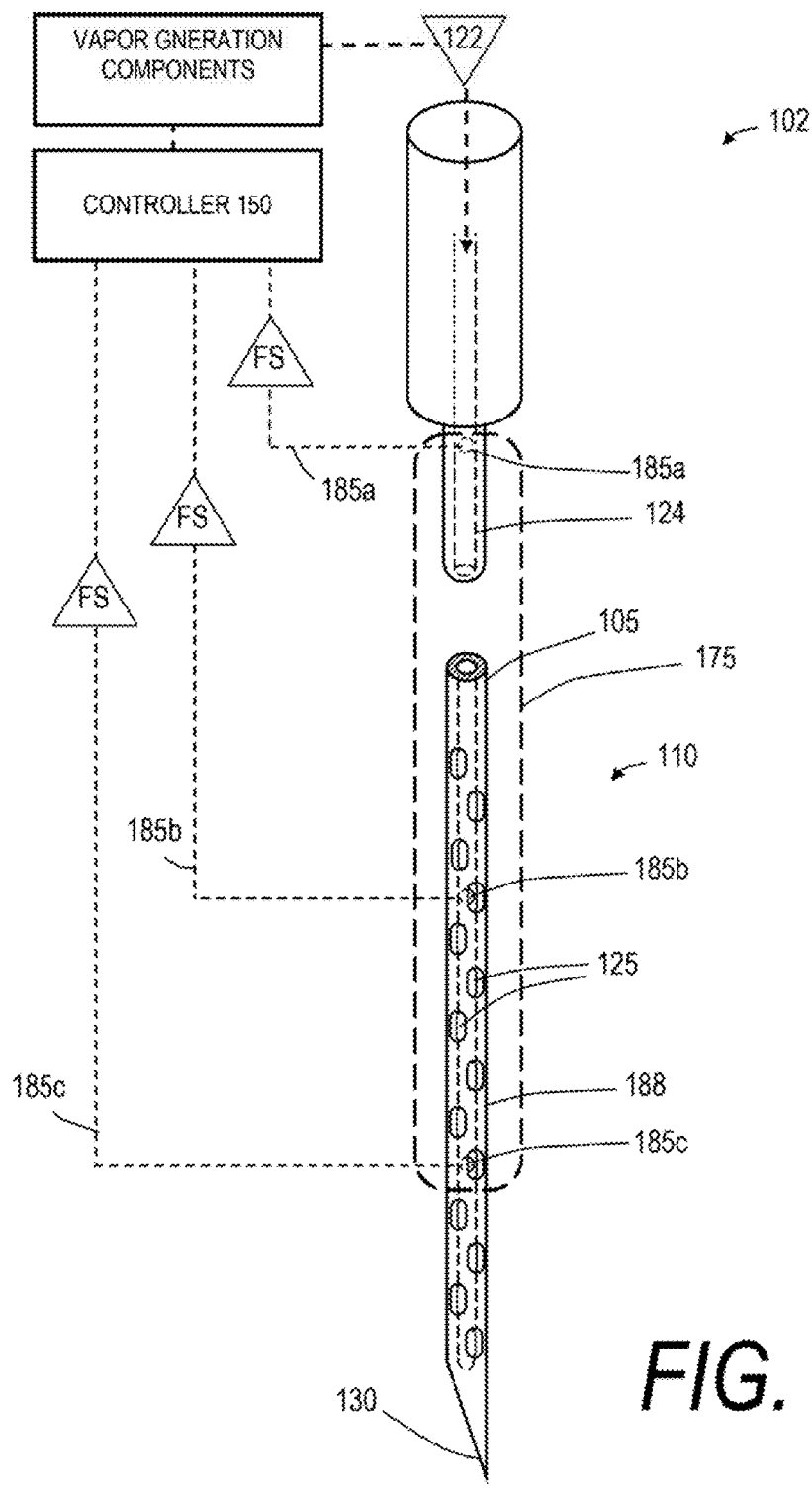
FIG. 7 is an illustration of the needle-like working end as in FIGS. 2 and 4A with a sensor system.

Referring to FIG. 7, one embodiment of sensor system 175 is shown that is carried by working end 110 of the probe 102 depicted in FIG. 2 for determining a first vapor media flow parameter, which can consist of determining whether the vapor flow is in an "on" or "off" operating mode. The working end 110 of FIG. 7 comprises a sharp-tipped needle suited for needle ablation of any neoplasia or tumor tissue, such as a benign or malignant tumor as described previously, but can also be any other form of vapor delivery tool. The needle can be any suitable gauge and in one embodiment has a plurality of vapor outlets 125. In a typical treatment of targeted tissue, it is important to provide a sensor and feedback signal indicating whether there is a flow, or leakage, of vapor media 122 following treatment or in advance of treatment when the system is in "off" mode. Similarly, it is important to provide a feedback signal indicating a flow of vapor media 122 when the system is in "on" mode. In the embodiment of FIG. 7, the sensor comprises at least one thermocouple or other temperature sensor indicated at 185a, 185b and 185c that are coupled to leads (indicated schematically at 186a, 186b and 186c) for sending feedback signals to controller 150. The temperature sensor can be a singular component or can be plurality of components spaced apart over any selected portion of the probe and working end. In one embodiment, a feedback signal of any selected temperature from any thermocouple in the range of the heat of vaporization of treatment media 122 would indicate that flow of vapor media, or the lack of such a signal would indicate the lack of a flow of vapor media. The sensors can be spaced apart by at least 0.1 mm, 0.5 mm, 1 mm, 5 mm, 10 mm and 50 mm. In other embodiments, multiple temperature sensing event can be averaged over time, averaged between spaced apart sensors, the rate of change of temperatures can be measured and the like. In one embodiment, the leads 186a, 186b and 186c are carried in an insulative layer of wall 188 of the extension member 105. The insulative layer of wall 188 can include any suitable polymer or ceramic for providing thermal insulation. In one embodiment, the exterior of the working end also is also provided with a lubricious material such as Teflon® which further insures against any tissue sticking to the working end 110.

Still referring to FIG. 7, a sensor system 175 can provide a different type of feedback signal FS to indicate a flow rate or vapor media based on a plurality of temperature sensors spaced apart within flow channel 124. In one embodiment, the controller 150 includes algorithms capable of receiving feedback signals FS from at least first and second thermocouples (e.g., 185a and 185c) at very high data acquisition speeds and compare the difference in temperatures at the spaced apart locations. The measured temperature difference, when further combined with the time interval following the initiation of vapor media flows, can be compared against a library to thereby indicate the flow rate.

Figure 8:
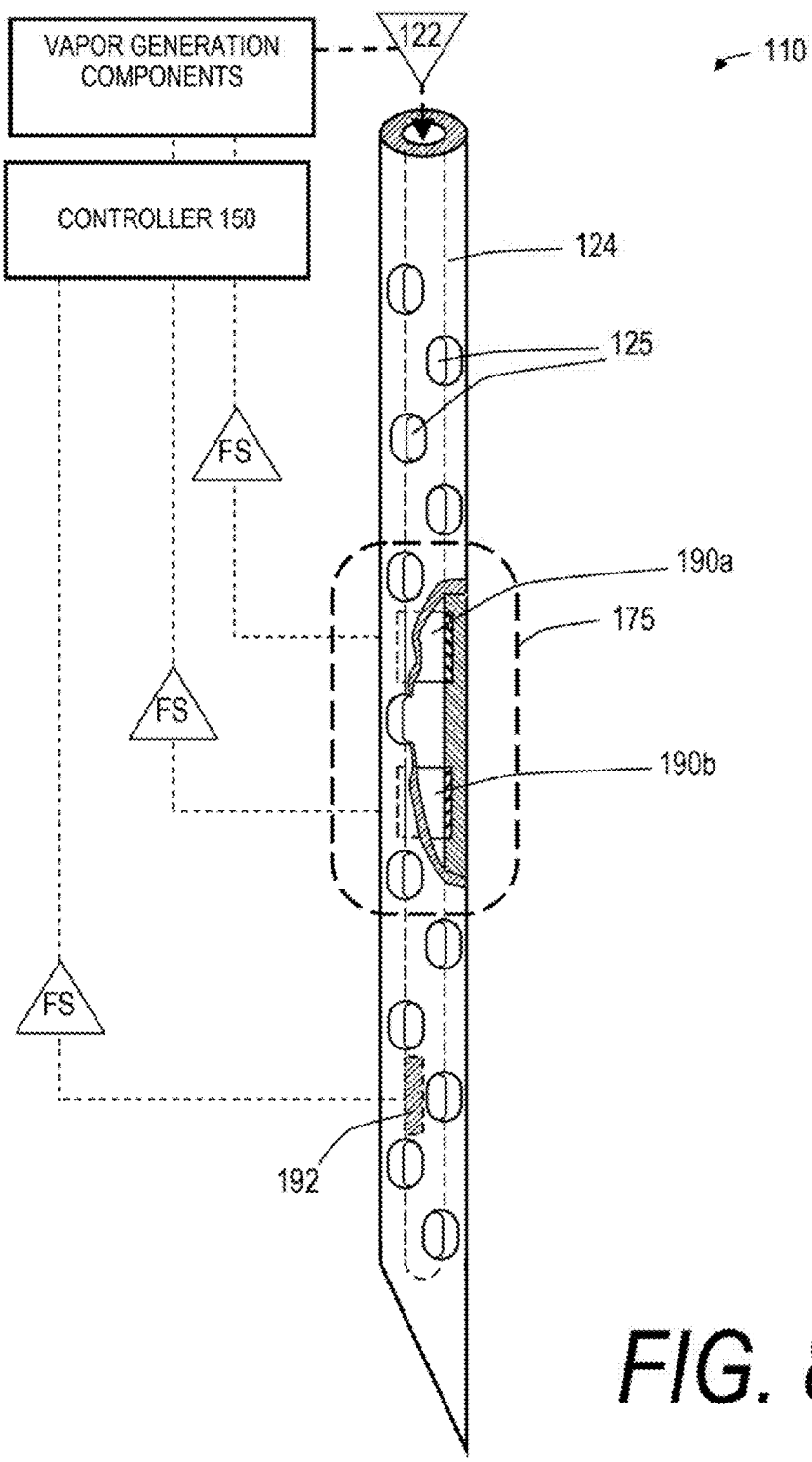
FIG. 8 is an illustration of a working end including an expandable member.

Another embodiment of sensor system 175 in a similar working end 110 is depicted in FIG. 8, wherein the sensor is configured for indicating vapor quality—in this case based on a plurality of spaced apart electrodes 190a and 190b coupled to controller 150 and an electrical source (not shown). In this embodiment, a current flow is provided within a circuit to the spaced apart electrodes 190a and 190b and during vapor flows within channel 124 the impedance will vary depending on the vapor quality or saturation, which can be processed by algorithms in controller 150 and can be compared to a library of impedance levels, flow rates and the like to thereby determine vapor quality. It is important to have a sensor to provide feedback of vapor quality which determines how much energy is being carried by a vapor flow. The term "vapor quality" is herein used to describe the percentage of the flow that is actually water vapor as opposed to water droplets that is not phase-changed. In another embodiment (not shown) an optical sensor can be used to determine vapor quality wherein a light emitter and receiver can determine vapor quality based on transmissibility or reflectance of a vapor flow.

Figure 1A:
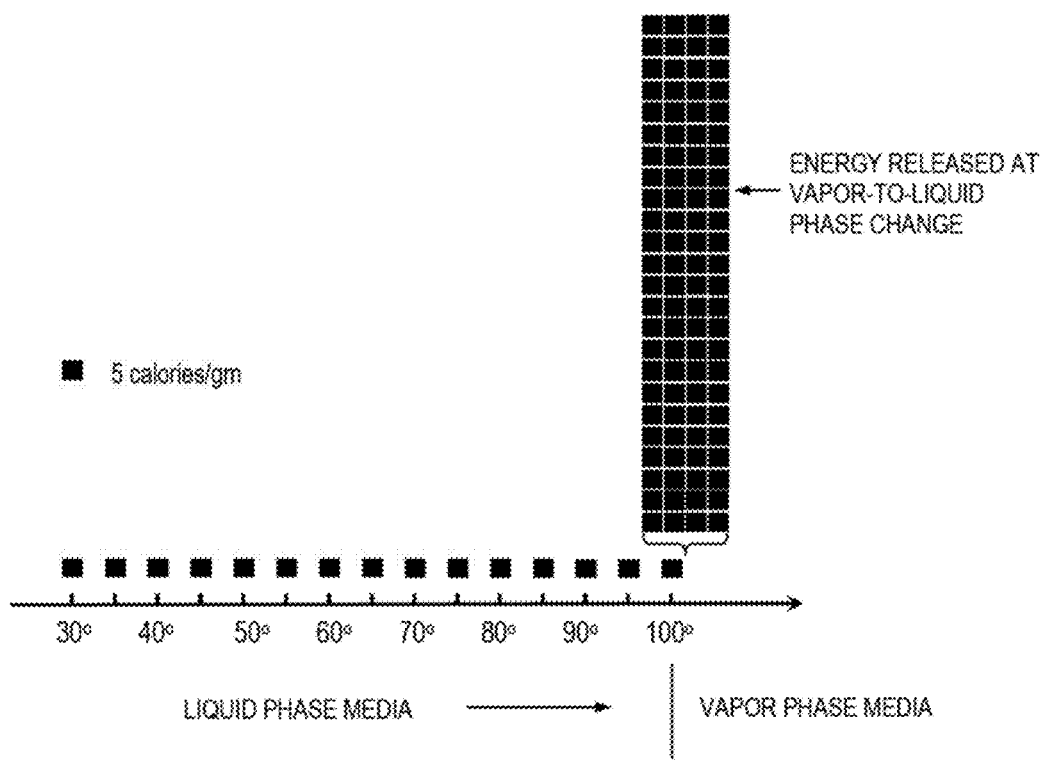
FIG. 1A is a graphical depiction of the quantity of energy needed to achieve the heat of vaporization of water.
Figure 1B:
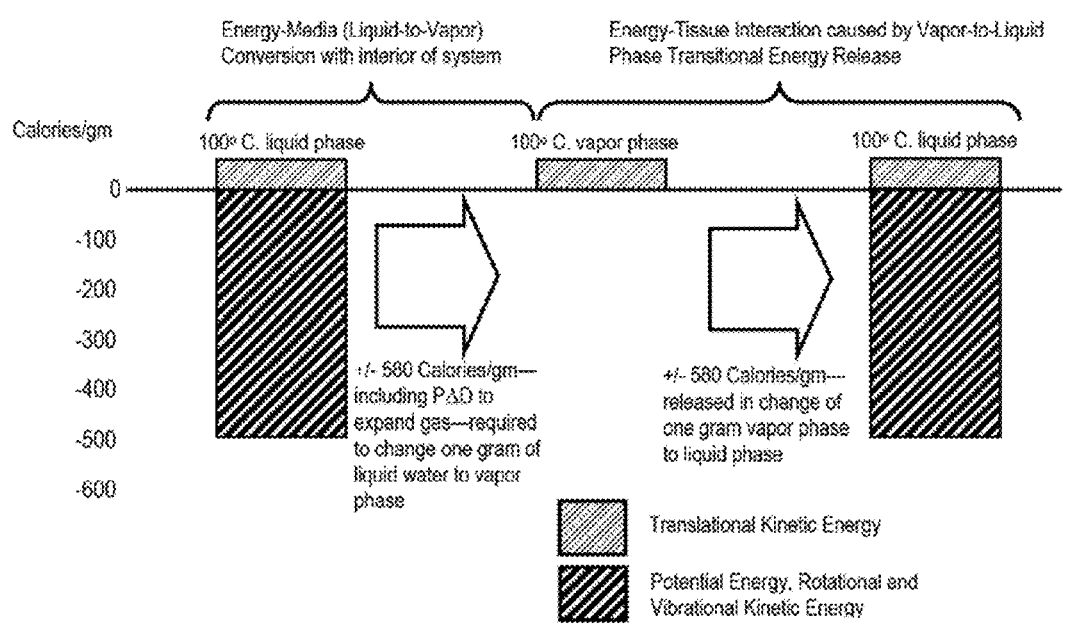
FIG. 1B is a diagram of phase change energy release that underlies a system and method of the invention.

FIG. 8 further depicts a pressure sensor 192 in the working end 110 for providing a signal as to vapor pressure. In operation, the controller can receive the feedback signals FS relating to temperature, pressure and vapor quality to thereby modulate all other operating parameters described above to optimize flow parameters for a particular treatment of a target tissue, as depicted in FIG. 1. In one embodiment, a MEMS pressure transducer is used, which are known in the art. In another embodiment, a MEMS accelerometer coupled to a slightly translatable coating can be utilized to generate a signal of changes in flow rate, or a MEMS microphone can be used to compare against a library of acoustic vibrations to generate a signal of flow rates.

Figure 9A:
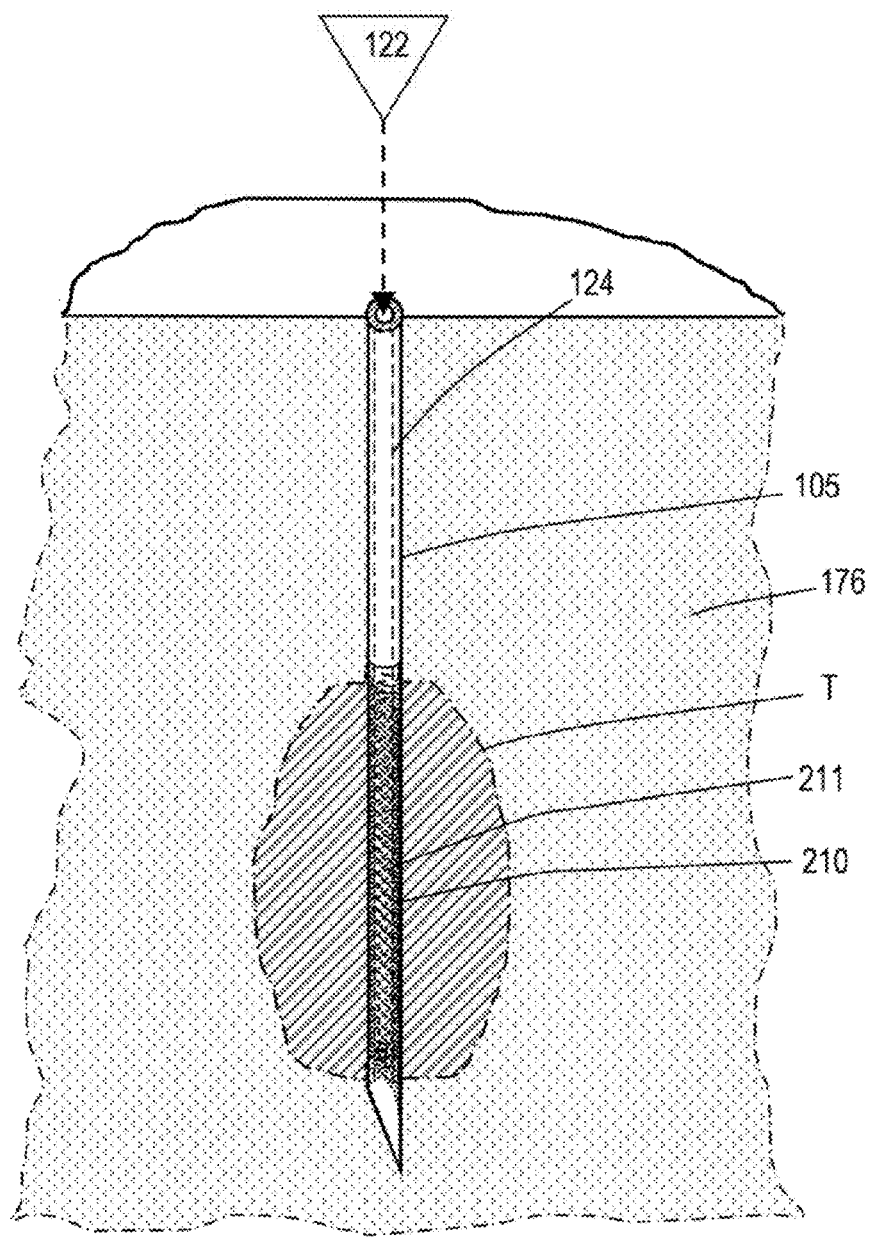
FIG. 9A is an illustration of an expandable working end being introduced into soft tissue.
Figure 9B:
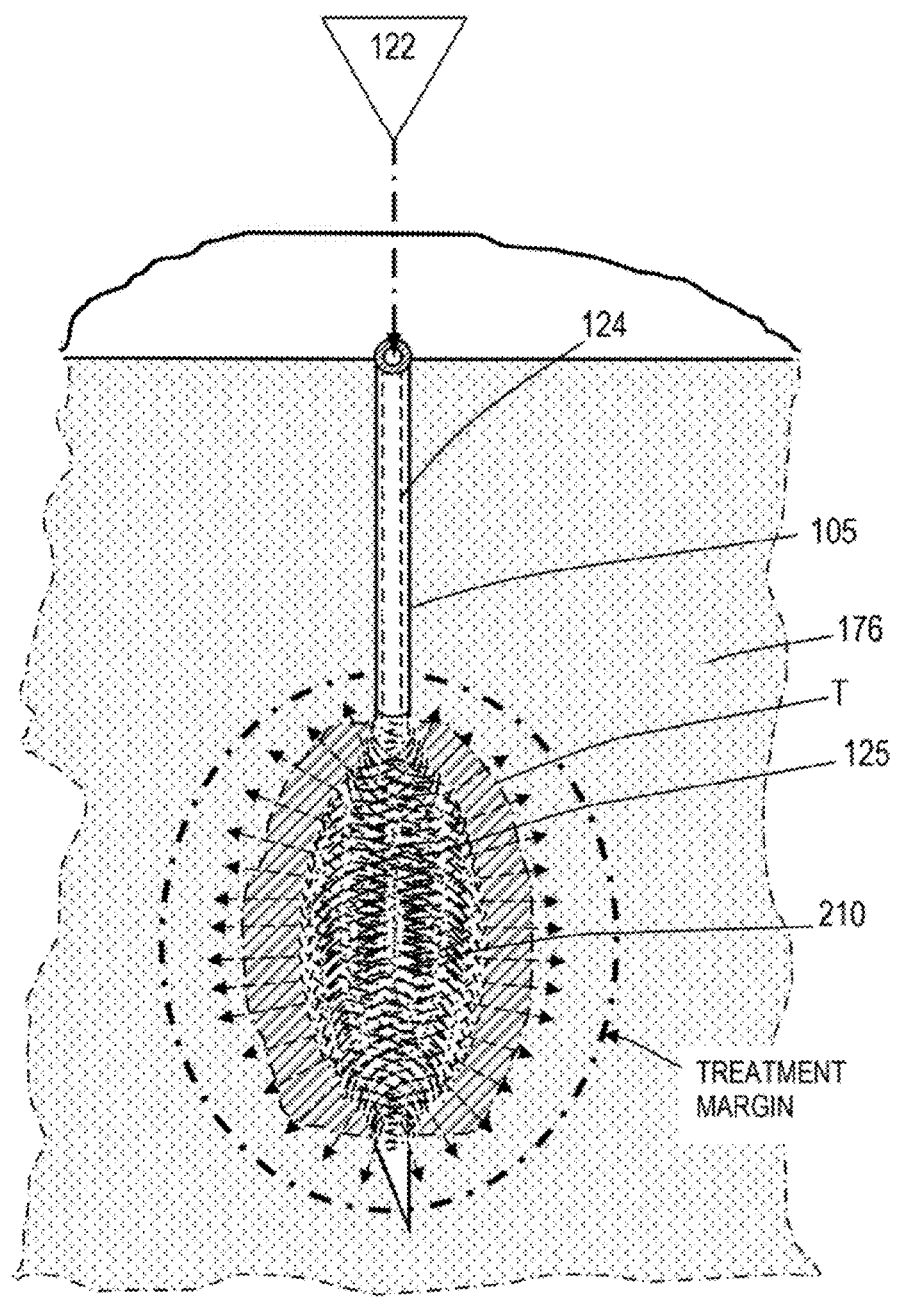
FIG. 9B is an illustration of the working end of FIG. 9A showing the propagation of vapor media in tissue to ablate tumorous tissue.

FIGS. 9A and 9B illustrate another embodiment of vapor delivery tool and working end 110 that is coupled to a vapor source and controller 150 as described above (see FIG. 2). In this embodiment, the extension member 105 is similar to that of FIGS. 4A and 4B but includes an expandable working end indicated at 210. As can be seen in FIGS. 9A-9B, the working end includes a region that is woven, knit or braided from wire-like metal or polymer filaments 211 around a flow channel 124 that extends through extension member 105 and wherein the inflow pressure of the vapor 122 is controlled to cause expansion of the woven filament working end at the same time as diffusing the vapor flow from the plurality of outlets 125 can between the filaments 211 (FIG. 9B). The expansion of the working end is adapted to apply compression against the soft tissue and tumor T to thereby alter convective heating effects in such tissue. Such compression increases local tissue density and can make tissue density more uniform, for example, by collapsing vessel and lumens in the targeted tissue which may otherwise cause a pathway for convective heat transfer to migrate non-uniformly.

Figure 10A:
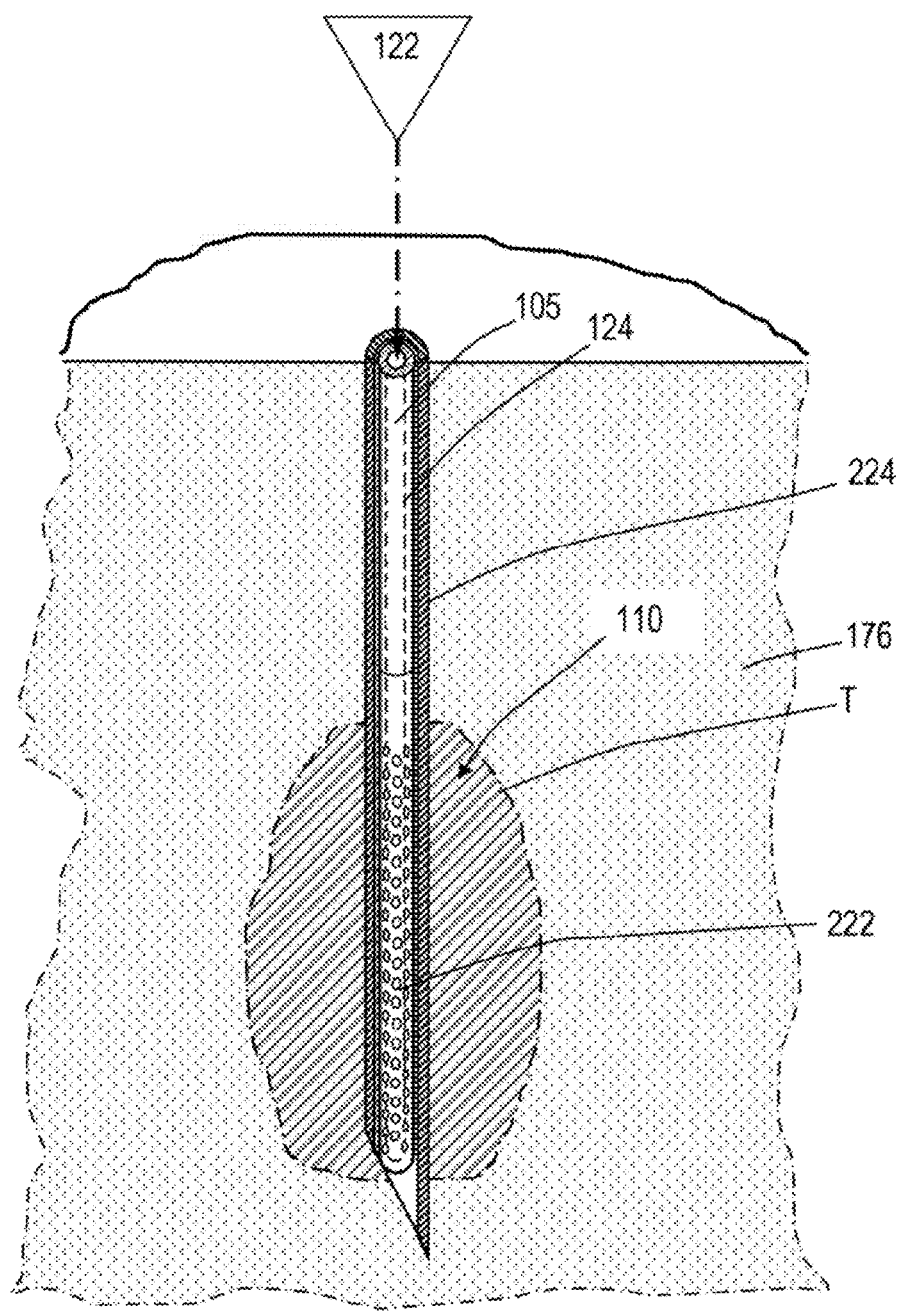
FIG. 10A is an illustration of an expandable working end and sleeve being introduced into soft tissue.
Figure 10B:
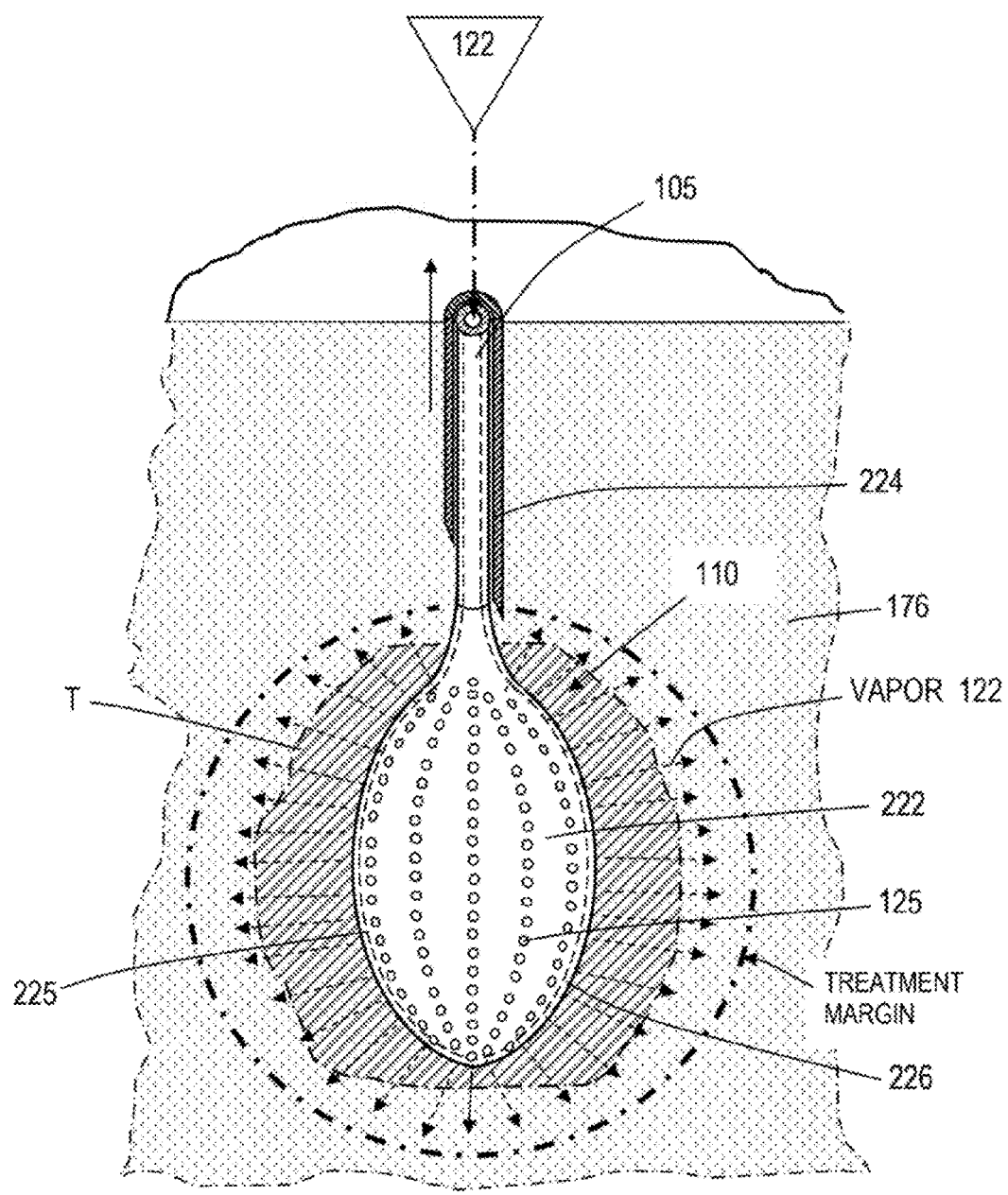
FIG. 10B is an illustration of the working end of FIG. 10A showing the propagation of vapor media in tissue.

FIGS. 10A and 10B illustrate another vapor delivery tool with an extension member 105 having a working end 110 that carries a non-complaint or compliant expandable structure 222 such as a balloon made of any suitable temperature resistant polymer known in the art. The balloon 222 can be sealed and coupled to the extension member 105 by adhesives or collars. In a method of use as shown in FIGS.

10A-10B, the expandable working end 220 can be carried is a retractable sheath 224 that is inserted into tissue (FIG. 10A) and then withdrawn to dispose the working end 110 in the targeted tissue. The balloon 222 has an interior chamber 225 with a wall 226 that is microporous or has plurality of outlets 125 therein as depicted in FIG. 10B. As can be seen in FIG. 10B, the inflow of vapor 122 from source 120 is modulated by a controller 150 to expand the balloon 222. Thereafter, the vapor propagates from the outlets 125 in the balloon wall to apply energy to the tissue interfacing with the balloon wall.

Figure 11:
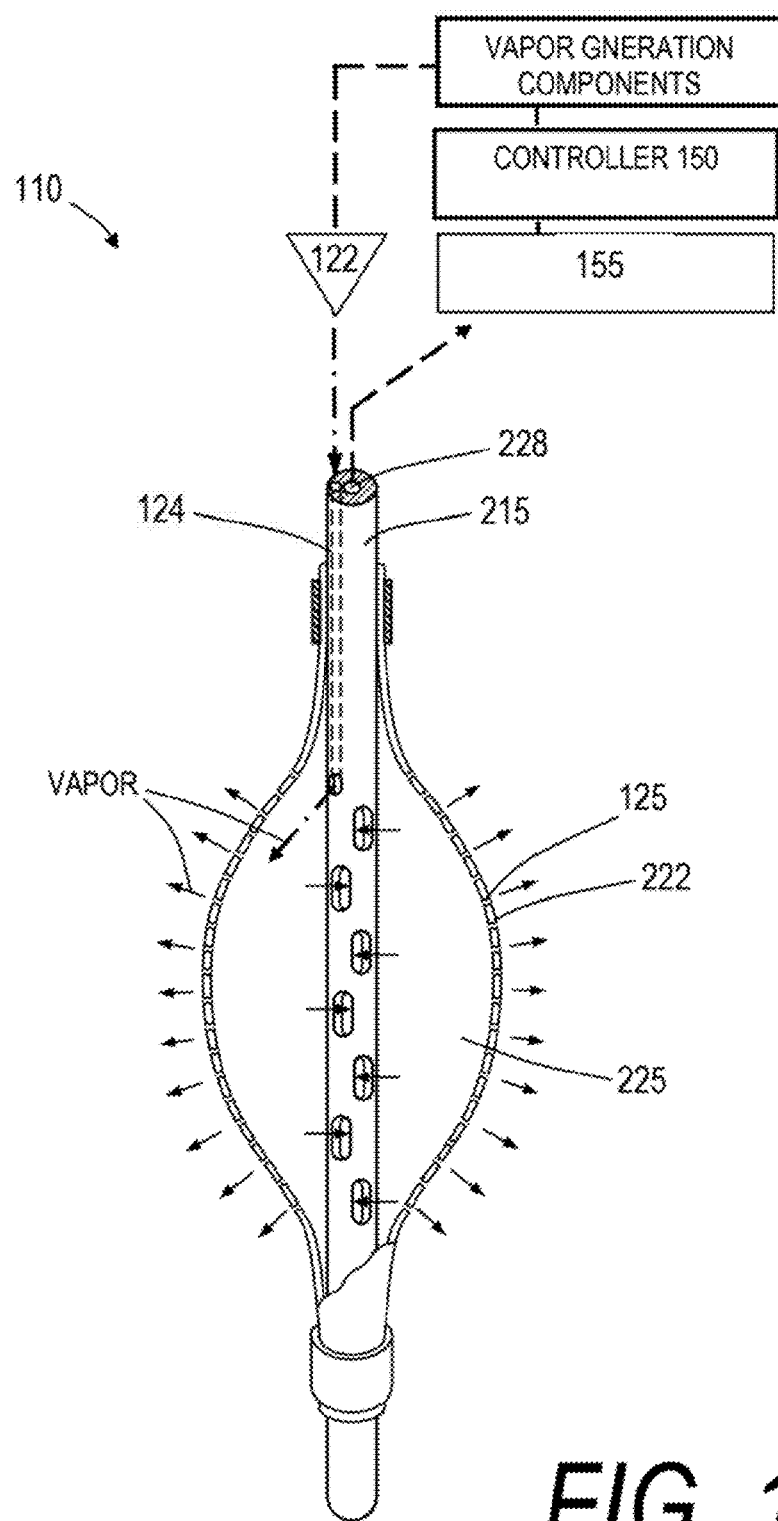
FIG. 11 is a cut-away view of an expandable working end with a recirculation flow channel.

FIG. 11 is a cutaway view of another vapor delivery tool or probe with extension member 105 and working end 110 that includes an expandable structure 222 similar to that of FIGS. 10A-10B. The embodiment of FIG. 11 includes a first flow channel 124 for carrying the vapor into the interior chamber 225 of the expandable structure 222 and a second recirculating flow channel 228 in communication with negative pressure source 155 for aspiration or extraction of a flow of media from the interior chamber 225. This embodiment thus uses both a pressurized inflow source 120 and the recirculation channel 228 coupled to negative pressure source 155 to allow the controller to precisely modulate flow from outlets 125 in the expandable structure 222. The embodiment of FIG. 11 is shown for convenience with a substantially symmetrical balloon, but it should be appreciated that the balloon can be any symmetric, elongated, complex or asymmetric shape and can be configured for deployment and expansion in soft tissue or can be configured for deployment in a body cavity or lumen, such as a blood vessel, AVM, a patient's uterus, a nasal passageway or sinus, a gall bladder or other hollow organ, the gastrointestinal tract or the respiratory tract. The expandable structure 222 or balloon can have multiple chambers with internal constraining elements to allow the balloon to deployably expand to an asymmetric shape.

Figure 12A:
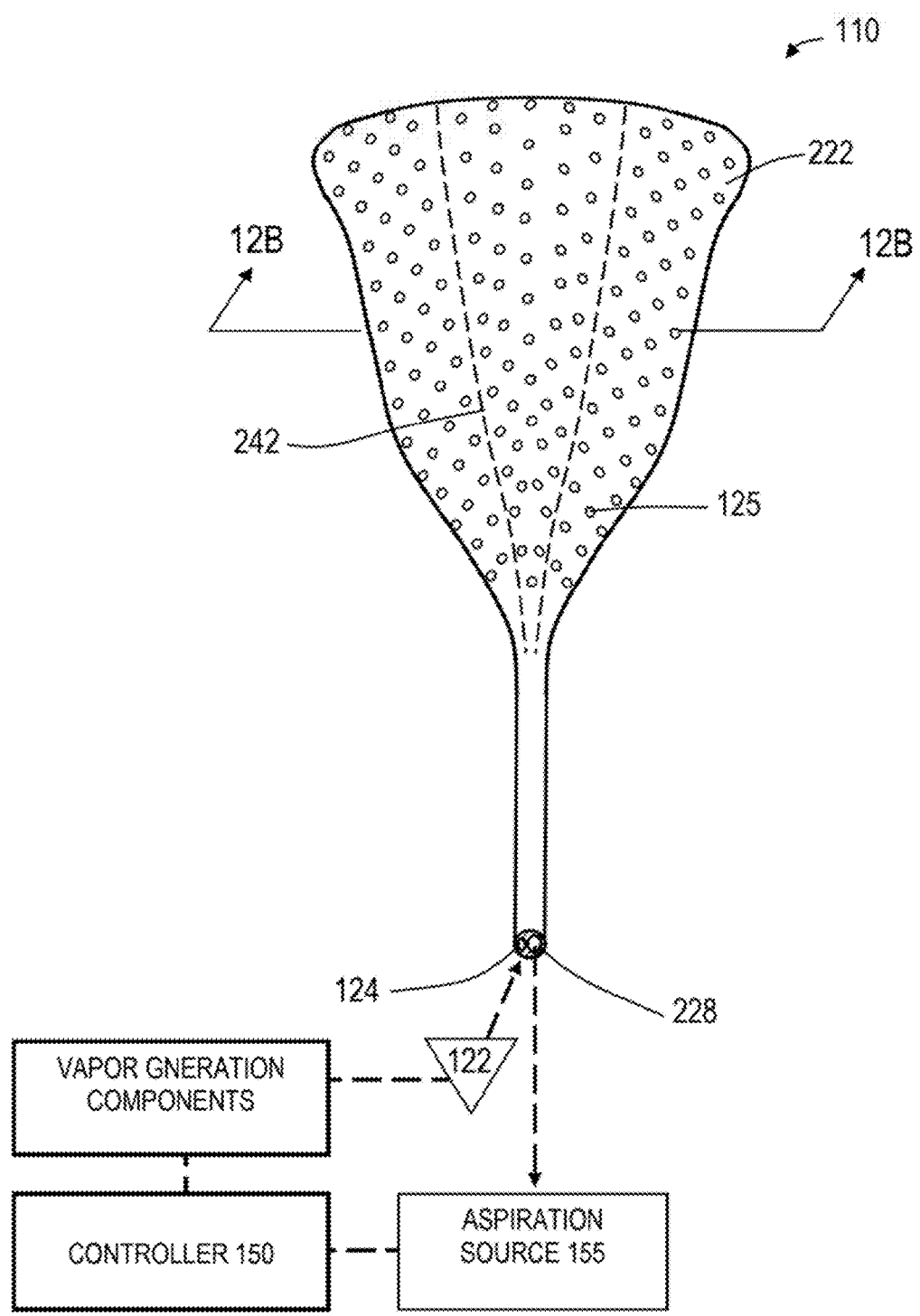
FIG. 12A is an illustration of an expandable working end configured for positioning in a uterine cavity for an endometrial ablation treatment.
Figure 12B:
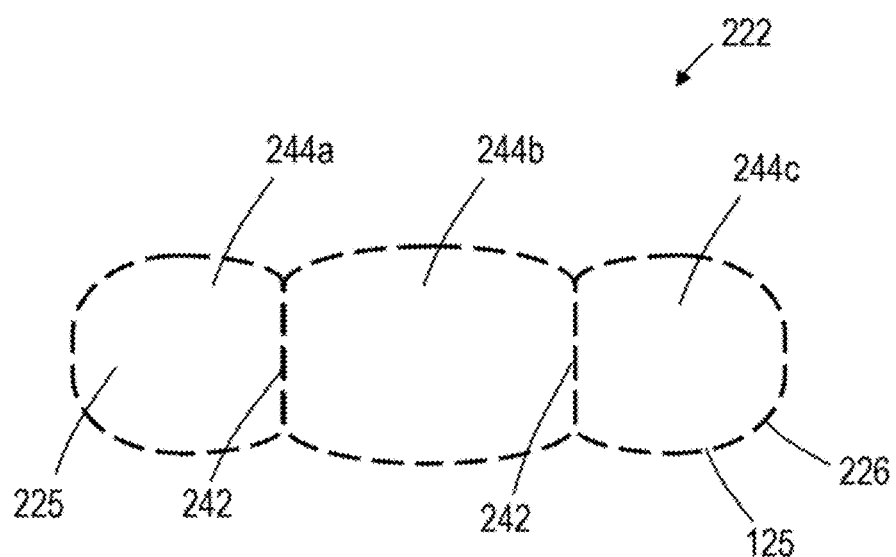
FIG. 12B is a sectional view of the expandable working end of FIG. 12A.

FIGS. 12A and 12B depict another system and working end 110 with an asymmetric shaped expandable structure 222 configured for deployment in a patient's uterus to apply energy for an endometrial ablation treatment. It can be seen that expandable structure 222 is shaped to occupy the cavity of a uterus and has a plurality of interior chamber portions 225 collectively in FIG. 12B separated by a vapor impermeable or permeable wall 242. The expandable structure 222 can have from 2 to 100 or more such chambers and is shown in FIGS. 12A and 12B with three chamber portions 244a, 244b, 244c. The balloon wall 226 has vapor outlets 125 as described previously, and further includes the recirculation channel 228 and pressure control system as described in the embodiment of FIG. 11. The expandable structure 222 of FIG. 12B is shown with a plurality of outlets 125 or porosities in the wall 226 of the balloon, and it should be appreciated that the outlets can vary in density and dimension to permit greater and lesser vapor propagation through selected regions of the wall. For example, greater vapor flows can be directed to thicker endometrial portions to increase the depth of ablation, and lesser vapor flows can be directed to thinner layers of the endometrium and toward the fallopian tubes.

Figure 12C:
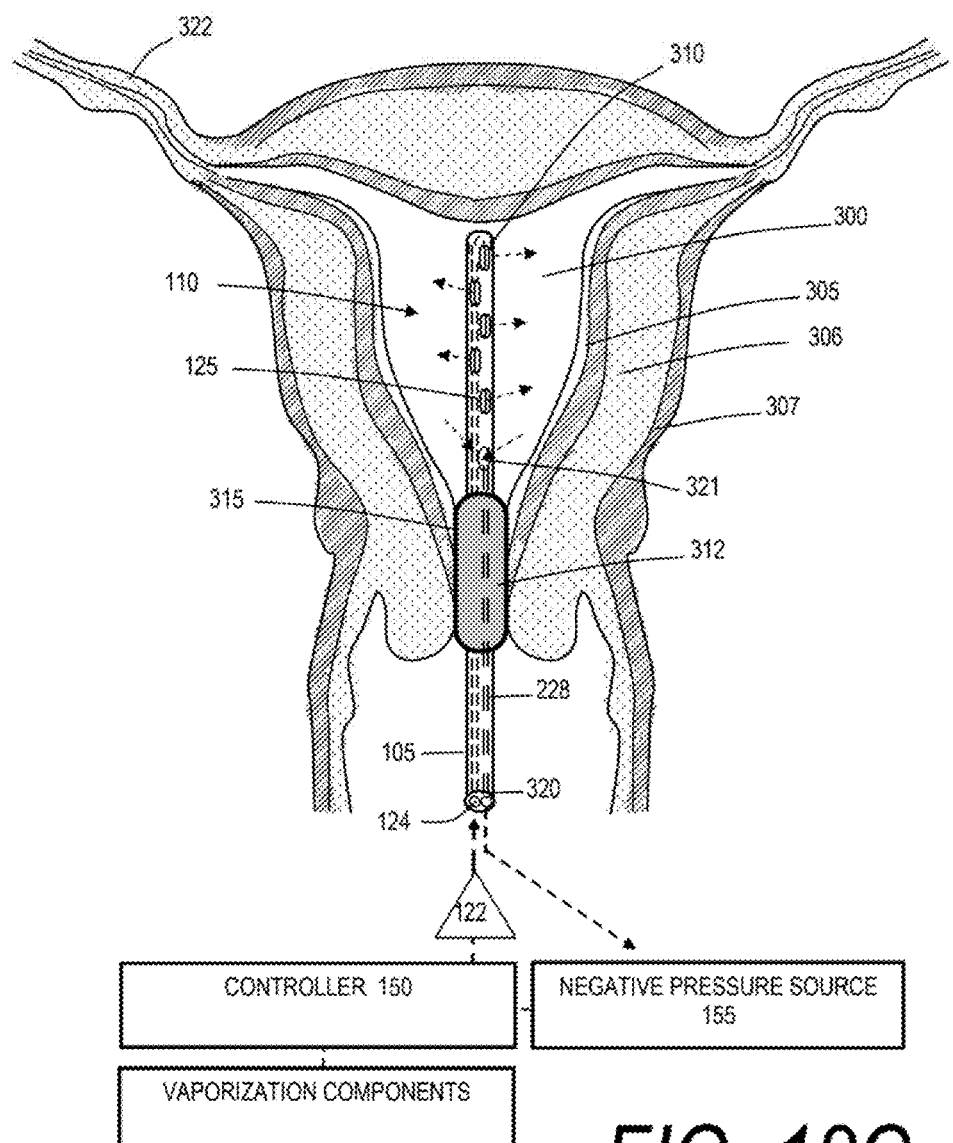
FIG. 12C is a view of another non-expandable working end in an endometrial ablation treatment method.

FIG. 12C illustrates another probe embodiment for applying energy to a body cavity and more particularly to a uterine cavity 300 for accomplishing an endometrial ablation treatment. This embodiment is similar to that of FIGS. 4A-4B wherein the working end 110 is a non-expandable tubular member. FIG. 12C illustrates the endometrium 305 that is targeted for ablation to treat menorrhagia. The endometrium 305 is the uterine lining that is inward of the myometrium 306 and perimetrium 307. The embodiment of FIG. 12C has working end 110 that has a soft or blunt distal tip 310 that is dimensioned for insertion through cervix 312. The working end 110 can range from about 2 mm to 8 mm in diameter, and can have a vapor delivery lumen 124 that is substantially small for vapor delivery to one or more outlets 125 with the outlets distal of expandable balloon 315. The extension member 105 includes with a substantial insulative layer 320 (further described below) that extends to the working end 110. In this embodiment, the extension member 105 and working end 110 can be fabricated of a polymer material such as PEEK, PTFE, Nylon or polypropylene and a plurality of outlets 125 for vapor ejection can be provided in selected radial directions over a selected length of the working end 110. In another embodiment, the working end 110 can have a single outlet 125. In one embodiment, the working, end 110 has an expansion member or balloon 315 positioned proximal to the vapor outlet(s) 125 to prevent proximal vapor flows retrograde from the uterine cavity and to protect the cervix 312 from high temperatures. The deployment of balloon 315 can further allow a selected pressure to be maintained in the cavity wherein another lumen 228 (aspiration lumen) with port 321 in the working end is coupled to negative pressure source 155 that includes a valve configured to control outflows from the uterine cavity with the valve operatively connected to controller 150. In another embodiment, the working end 110 can include any inflatable, actuatable or spring-like frame to distend the cavity in the uterus, as well as expandable balloons or similar structures (not shown) for preventing vapor flow into the fallopian tubes 322. As can be understood from FIG. 12C, the endometrial ablation system can have all of the features, sensors and subsystems described elsewhere herein in the various embodiments. In one method, the system and controller can utilize the controller 150 and valve connected to the aspiration lumen 228 in the probe valve to provide a pressure in the uterus during treatment ranging between 0.1 psi and 50 psi, between 0.2 psi and 10 psi, and between 0.5 psi and 5 psi. In the embodiment of FIG. 12C, the inflation lumen to expand the balloon 322 is not shown and can be manually operated or can be operatively coupled to controller 150. In another method, the system allows controlled distension of a body cavity with a gas or vapor media, such as a uterine cavity, in combination with the vapor media applying a selected amount of ablative energy uniformly about the surface of the distended body cavity.

Figure 12D:
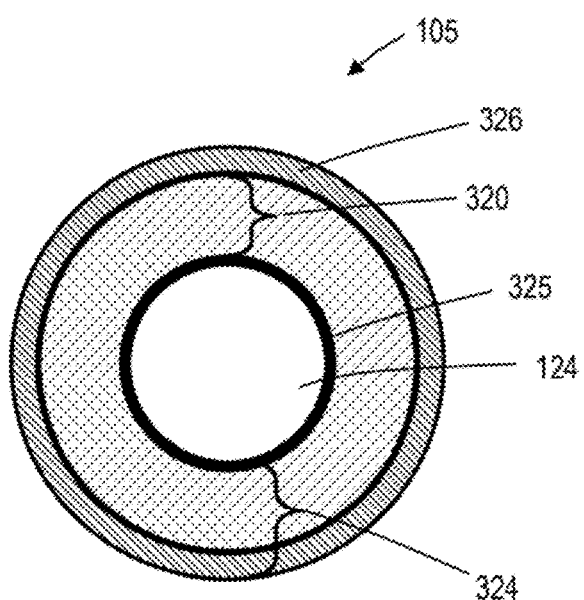
FIG. 12D is a view of a cross-section of an insulative wall portion of a vapor delivery probe.

In another aspect of the invention, a vapor delivery system as described above can have an extension member 105 (FIGS. 4A-12C) with an insulative wall, as depicted in the cross-sectional view of FIG. 12D. In FIG. 12D, it can be seen that at least one flow channel 124 is within an interior of the surrounding structure or wall 324 that includes a thermally insulative layer or region indicated at 320. In one embodiment, the extension member 105 has a thin inner layer 325 around the flow channel 124 which is of a biocompatible fluid impermeable material such as a polymer (Teflon®) or a metal such as a stainless steel. A flexible vapor delivery extension member can include an electroless plating over a polymer base to provide biocompatible inner layer 325. Outward from the inner layer 325 is the insulating region or layer 320 that can comprise air channels, voids with a partial vacuum, a region that carries an aerogel or aerogel particles optionally under a partial vacuum, a region that carries hollow glass or ceramic microspheres, or a region with a channel or multiple channels that provide for a flow of air or a liquid about the at least one flow channel 124. An extension member 105 that includes flow channels or recirculation channels can be coupled to any positive and negative pressure sources known in the art to cause a flow of air, cooling fluids, cryogenic fluids and the like through such channels. The exterior 326 of the wall 324 can be any suitable layer of a high temperature resistant polymer such as PEEK. Other materials used in an extension member can comprise formulations or blends of polymers that include, but are not limited to PTFE, polyethylene terephthalate (PET), or PEBAX. PTFE (polytetrafluoroethylene) is a fluoropolymer which has high thermal stability (up to 260° C.), is chemically inert, has a very low dielectric constant, a very low surface friction and is inherently flame retardant. A range of homo and co-fluoropolymers are commercialized under such names as Teflon®, Tefzel®, Neoflon®, Polyflon® and Hyflon®. In one embodiment, the insulative layer 320, or inner layer 325 and insulating layer 320 in combination, or the entire wall 324, can have a thermal conductivity of less than 0.05 W/mK, less than 0.01 W/mK or less than 0.005 W/mK. In another aspect of the invention, the wall is configured at least partially with materials interfacing the channel that have a heat capacity of less than 2000 J/kgK for reducing condensation in the flow channel upon the initiation of vapor flow therethrough.

Figure 13A:
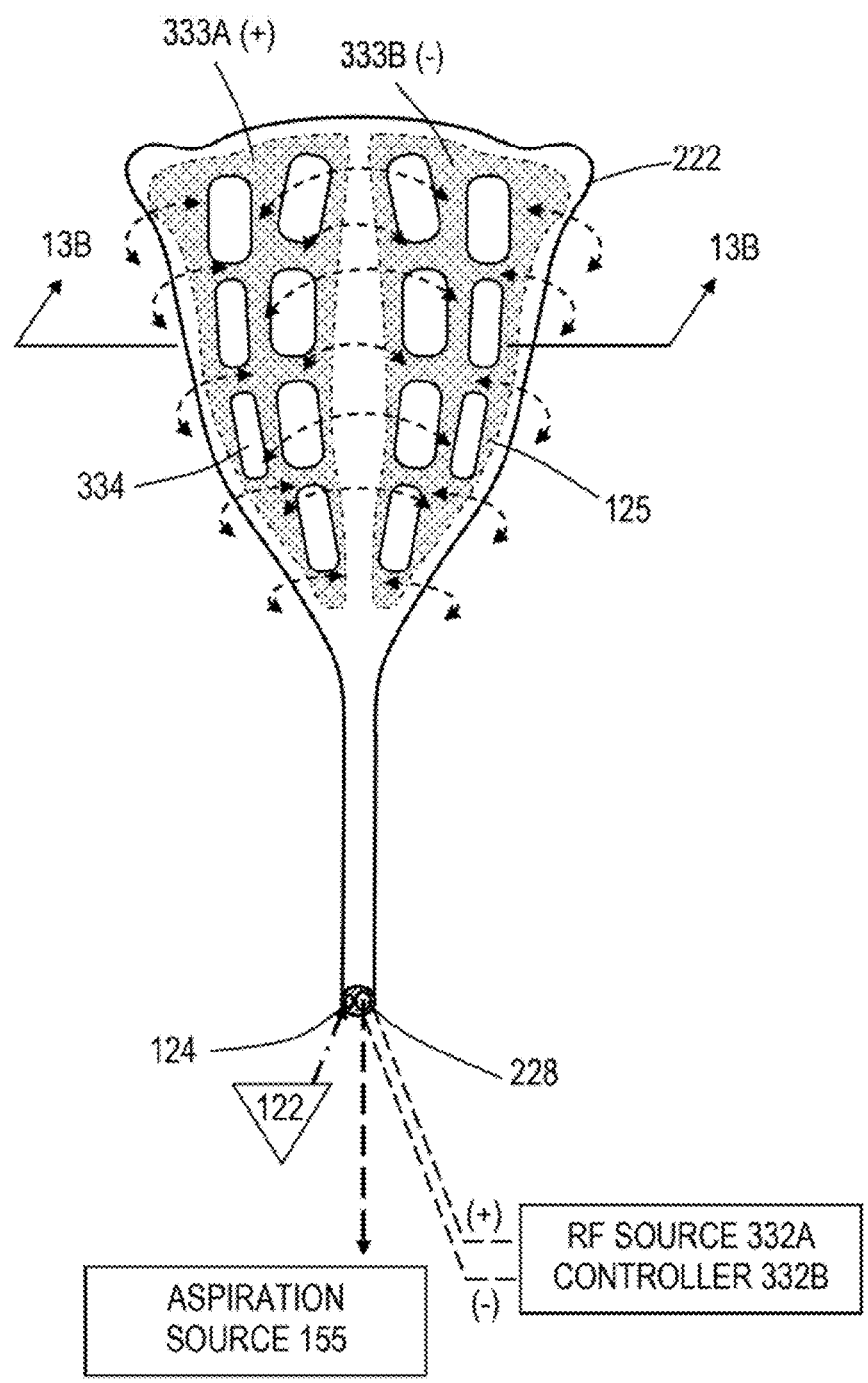
FIG. 13A is an illustration of another expandable working end with a surface electrode arrangement.
Figure 13B:
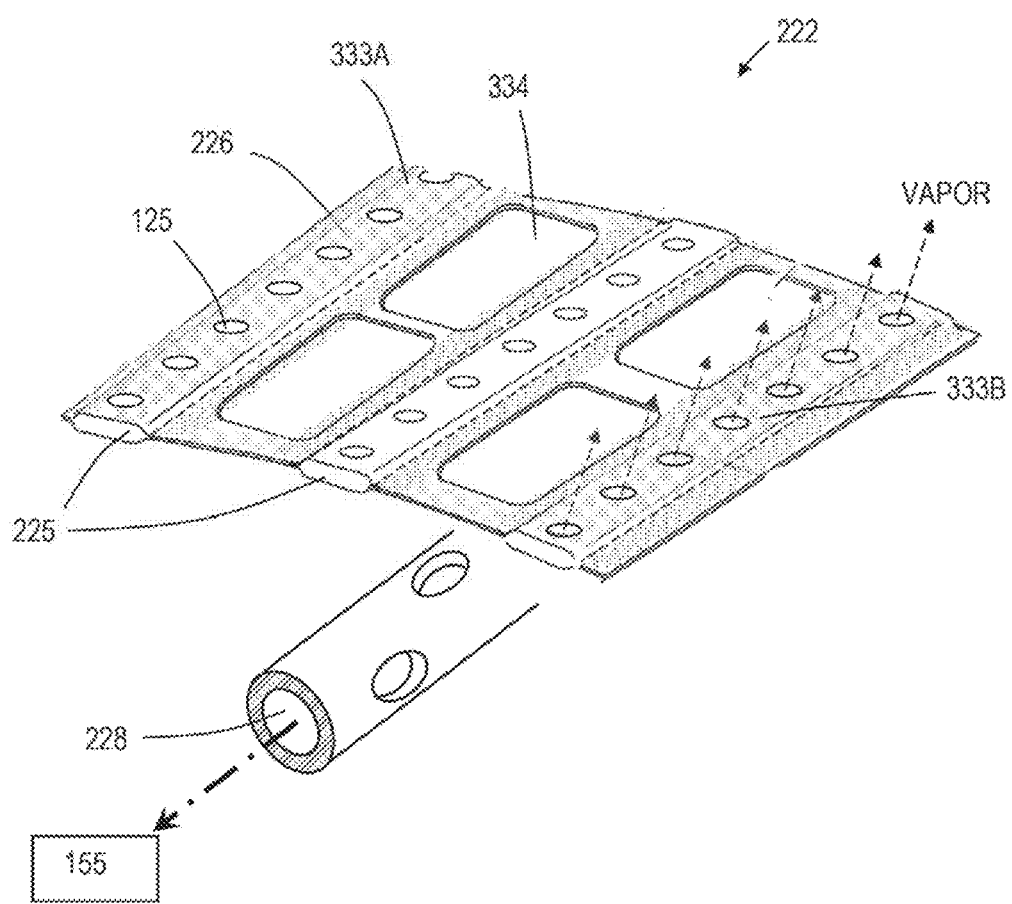
FIG. 13B is a sectional view of the expandable working end of FIG. 13A.

FIGS. 13A-13B illustrate another system with expandable working end similar to that of FIGS. 12A-12B with an additional energy delivery system carried by the expandable structure 222. As can be seen in FIG. 13A, the surface of expandable structure 222 carries at least one electrode arrangement operatively coupled to an electrical source such as an Rf source 332A and Rf controller 332B. The energy delivery system can comprise a surface electrode on the expandable structure 222 that cooperates with a ground pad, or as shown in the FIG. 13A, the system can carry spaces apart bi-polar electrodes that can comprise conductive coatings on a non-complaint balloon. In one embodiment of FIG. 13A, opposing polarity (+) and (−) electrodes 333A and 333B are shown and are adapted to apply energy to tissue as well as vapor 122 that exits the outlets 125. The current flows between the electrodes 333A and 333B are indicated by dashed lines in FIG. 13A, with such electrodes spaced apart is four quadrants around the structure. It should be appreciated that such spaced apart bi-polar electrode pairs can number from 2 to 100 or more about the surface of the structure. In one embodiment, hypertonic saline is vaporized to provide the flow of vapor 122 and saline droplets which will enhance Rf energy delivery to the tissue. FIG. 13B shows a cross section of a portion of wall 226 of the expandable structure of FIG. 13A wherein the interior chambers 225 (collectively) are channels in a thin film structure wall with outlets indicated at 125. In one embodiment, as in FIGS. 13A and 13B, the larger openings 334 permit vapor in the cavity extracted by a central aspiration or recirculation channel 228 at the interior of the structure similar to that of FIG. 11. The illustration of FIG. 13B does not show the interior constraining elements 242 as in FIG. 12B, but it should be understood that any number of such elements are possible to provide an asymmetric-shaped structure when pressurized.

In a method of use in treating the interior of an organ, with reference to FIGS. 12A, 12B and 12C, one method includes introducing the working end of an elongated probe introduction into a uterine cavity, providing a flow of a vapor media derived from water or saline from at least one outlet 125 in the working end 110 wherein the flow media applies a selected level of thermal energy to ablate at least portions of the endometrium. As described above, the ablation method is accomplished by allowing the vapor to collapse or condense to thereby release the heat of vaporization to uniformly ablate surface layers of the endometrium. Stated another way, the method includes converting the flow media from a first phase to a second phase thereby controllably applying thermal energy to the endometrium. One method includes introducing the flow media at a flow rate of ranging from 0.001 to 20 ml/min, 0.010 to 10 ml/min, 0.050 to 5 ml/min. One method includes introducing the flow media at an inflow pressure ranging from 0.5 to 1000 psi, 5 to 500 psi, and 25 to 200 psi. One method further includes applying the selected level of thermal energy over an interval ranging from 0.1 to 600 seconds; 0.5 to 300 seconds, and 1 to 180 seconds. Another method as described above includes providing a flow of a second media for combining with the vapor 122 to alter the average mass temperature of the combined vapor and second media.

In another aspect of the method of treating a uterus or the interior of another hollow organ, with reference to FIG. 12C, the system can be used to control the pressure within the uterus or other organ with controller 150 as described above. In one method, the controller 150 can control pressure in the cavity by modulating the inflow pressure of the flow media 122. In a related method, the controller 150 can control pressure by providing an outflow passageway in the probe for reducing pressure in the cavity. In an endometrial ablation procedure, the method includes providing a pressure in the uterus ranging between 0.1 psi and 6 psi, between 0.2 psi and 4 psi, and between 0.5 psi and 2 psi. This method includes controlling pressure in the uterus to distend the uterus during treatment. These methods also can be used when distending the uterus with an expandable working end.

Recirculation Channel, Flow Control, Insulative Subsystems

Figure 14A:
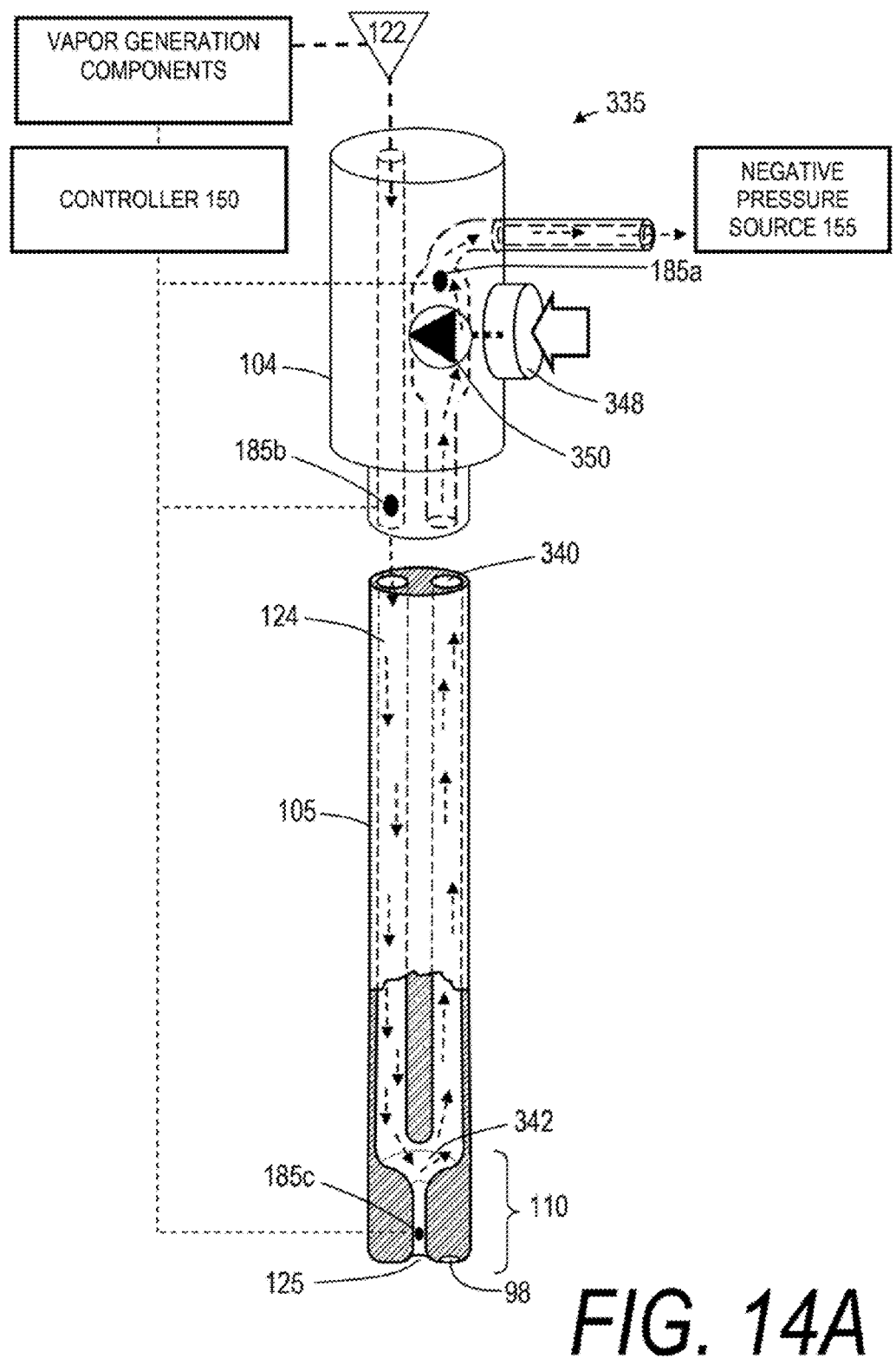
FIG. 14A is an illustration of a working end with a recirculation channel and valve for controlling vapor flows from the working end.
Figure 14B:
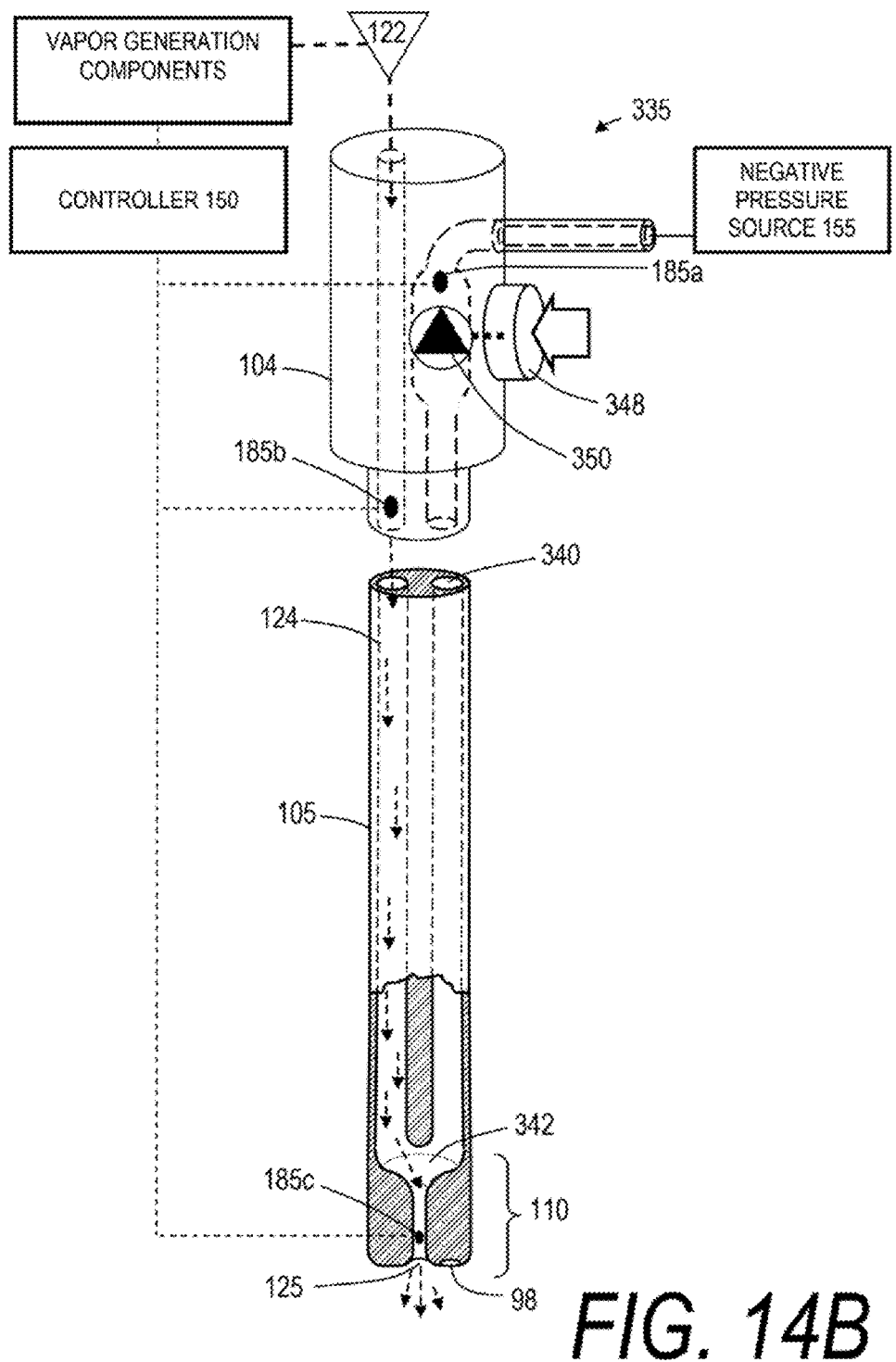
FIG. 14B is another view of the working end of FIG. 14A with the recirculation channel and valve in a different configuration.

FIGS. 14A and 14B depict another vapor deliver probe 335 with extension member 105 that can include the sensor subsystems as in the probe of FIG. 7 and additionally is configured with a second or recirculating flow channel 340 in the probe and extension member 105 that extends back to vent recirculation flows and optionally communicates with a negative pressure source 155 as depicted in FIG. 2. In one embodiment, the second channel or recirculating channel 340 is configured for controlling vapor flows to the outlet 125, which for example can be a single outlet or a plurality of outlets as in any embodiment described previously. In FIG. 14A, it can be seen that vapor media 122 generated by vapor generating components as described above and controller 150 to provide a pressurized vapor flow that flows distally through channel 124 and then reverses direction to flow in the proximally direction within channel region 342 that transitions into the second or recirculating channel 340. It can be understood that vapor media flows will continue in path of channel 124 and recirculation channel 340 so long as flow resistance is less through this pathway than through the small cross-section vapor outlet 125. In this aspect of the invention, the collective cross-section of the outlet(s) 125 is substantially less than the cross-section of the recirculating channel 340, for example, less than 20% of the recirculating channel 340, less than 10% of the recirculating channel 340, or less than 5% of the recirculating channel 340. The system includes means for closing the recirculating channel 340 to thus force vapor media 122 through the at least one outlet 125 to provides a "passive valve" at the outlet 125 and a method of instantly turning on a vapor flow from outlet 125 when operating a vapor generator in a continuous mode. In FIGS. 14A and 14B, it can be seen that a manual switch 348 in the handle portion 104 can operate valve 350 to block the recirculating channel 340 thus providing the passive valve that comprises the reduced cross-section outlet 125 at the working end. This form of passive valve is very useful in small diameter elongated extension members 105 such as an elongate flexible catheter. The switch can be in a proximal handle end 102 of the probe or optionally in a negative pressure source 155 coupled to recirculating channel 340 and can be operated by controller 150. In FIG. 14A, it can be understood that negative pressure source 155 can be operated to assist in exhausting vapor media from the recirculating channel 340 to enhance the recirculating flows. While the embodiment of FIGS. 14A-14B illustrates parallel channels 124 and 340, the channels can be varied, for example being concentric as described further below, or varied in cross section and/or length. The embodiment of FIGS. 14A-14B depict a blunt-tip working end 110 that can be used when injecting vapor into a lumen or body cavity such as a patient's respiratory tract, blood vessel, uterus, gastrointestinal tract and the like. It can be understood that a sharp-tip needle can be coupled to the distal end of the extension member 105 of FIGS. 14A-14B so that the passive valve is close to a needle that is configured to penetrate tissue for interstitial vapor delivery.

The embodiment of FIGS. 14A and 14B further illustrates a sensor system with temperature sensors 185a-185c as described above in the embodiment of FIG. 7. In addition, FIGS. 14A and 14B illustrate a visualization element 98 placed within a probe 335. In this variation the visualization element 98 is located in a working end 110 of the probe 335. However, the visualization element 98 can be located in any region of the device either by being placed within the device or otherwise attached to the device. Any number of visualization element 98 can be incorporated with the methods and devices described herein. For example, a visualization element 98 can include an optic fiber advanced within or adjacent to the device, a CCD camera affixed to the device or other visualization means as commonly used in remote visualization applications. The visualization element 98 can provide imaging before, during, and/or after the controlled flow egresses from the device. In addition, the visualization element can include thermal imaging capabilities to monitor the vapor flow from the device or the treatment effect in tissue.

Figure 15A:
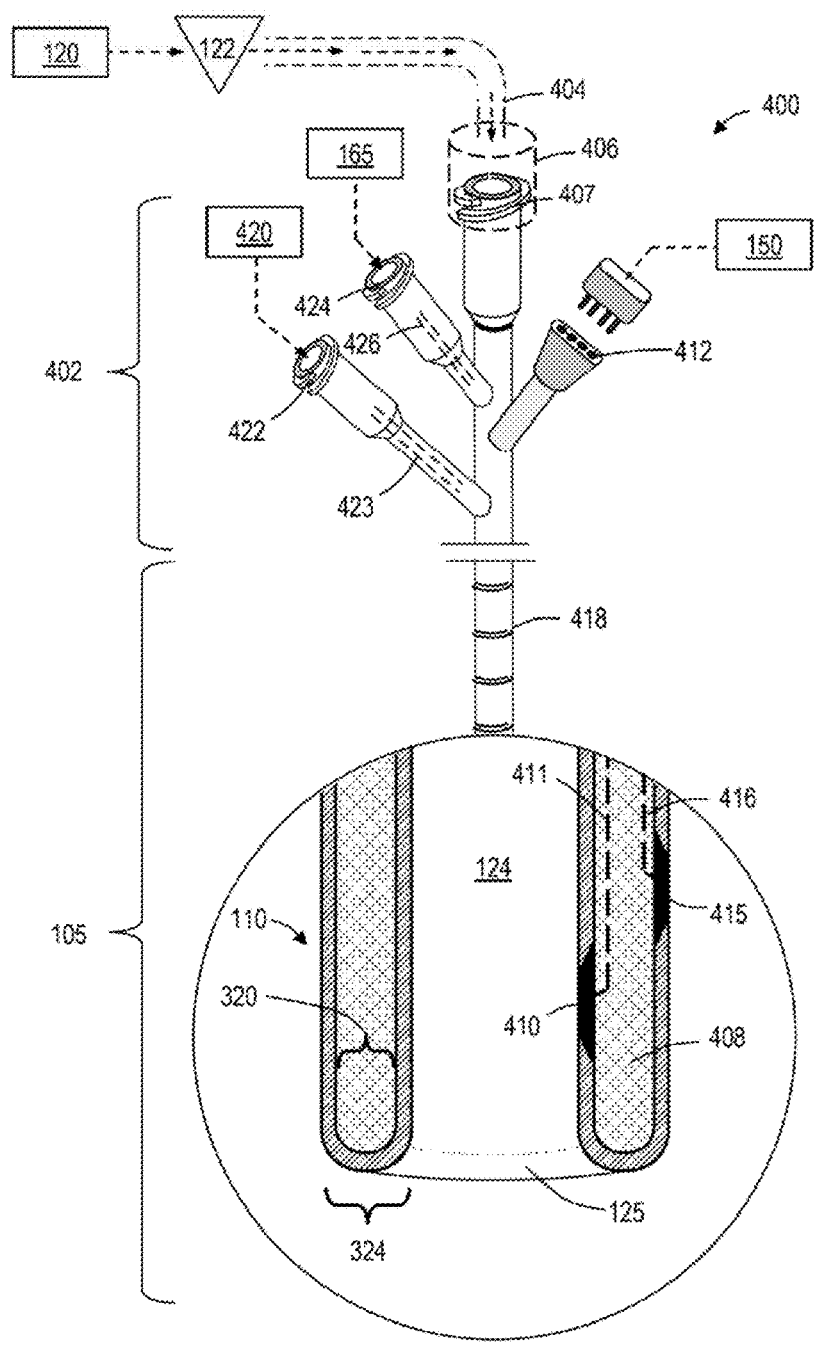
FIG. 15A is a view of a vapor delivery probe including a cross-sectional view of an insulative wall about a vapor delivery channel.

FIG. 15A illustrates a vapor delivery tool or probe 400 that has a hub or handle portion 402 with extension portion 105 and working end 110 that is configured with an insulated wall 324 about flow channel 124 as in the embodiment depicted in FIG. 12D. As can be understood from FIG. 15A, a liquid media source 120 and vapor generator provides vapor 122 and can be coupled to a flexible vapor delivery conduit 404 with a connector 406 that is coupled to Luer-type fitting 407 of the handle portion 402 of the probe. In one embodiment, the insulative region 320 of the wall comprises an aerogel 408 or an aerogel in a sealed insulative region 320 that is under a partial vacuum. Silica aerogels are a common form of aerogel having a very low thermal conductivity ranging from 0.03 W/m·K to 0.004 W/m·K. Other forms of aerogels may be used such as a carbon aerogel, or a combination silica and carbon aerogel.

As can be seen in FIG. 15A, the probe 400 includes a temperature sensor 410 in the end of flow channel 124 that corresponds to a part of a sensor system coupled through electrical lead 410 and connector 412 to controller 150 as described in the text accompanying FIGS. 7-8. Further, one embodiment carries another sensor or thermocouple indicated at 415 proximate an exterior surface of the extension member 105 coupled by lead 416 to the controller. The additional thermocouple 415, or a plurality of such thermocouples, can be used to measure surface temperature of an extension member in the interior of a patient's body, for example an elongate flexible catheter in a body lumen, to insure that a surface temperatures is not elevated above a point that causes an unwanted effect in tissue. The thermocouple 415 is coupled to controller 150 to provide feedback signals to thus allow modulation of a duty cycle or other operating parameter of vapor delivery.

In one aspect of the invention, a method of practicing a thermotherapy procedure includes positioning an insulative extension portion of a probe 400 in a patient's body to provide an access to a targeted site, and delivering a high temperature condensable vapor through a flow channel 124 in the probe 400 to provide an intended effect wherein a probe wall is configured with an insulative portion having a thermal conductivity of less than 0.05 W/mK, less than 0.01 W/mK or less than 0.005 W/mK to limit thermal transfer from a probe to tissue. In one embodiment, the probe 400 has a flow channel 124 with at region around the flow channel that is fabricated of a material having a heat capacity of less than 3000 J/kgK leas than 2500 J/kgK, of less than 2000 J/kgK, which can prevent condensation and thus improve vapor quality. In one embodiment, a system with a flow channel 124 between the vapor source 120 and the outlet 125 having the materials with flow channel walls including the low heat capacity material can provide a water vapor quality at the outlet 125 of at least 70% vapor, at least 80% vapor and least 90% vapor. Further, the method includes providing such vapor over a duty cycle ranging from 5 seconds to 5 minutes with less than 10% variation in said vapor quality. The quality of vapor is directly correlated to the amount of energy applied to tissue, so that it is critical to know the quality—and hence stored energy—in the vapor media. In other embodiments, the extension member 105 can be rigid, flexible, deflectable, malleable or curved. It can be understood that an elongate flexible catheter can be used in a treatment of varicose veins or other endovascular treatments. The extension member 105 can have a length of at least 10 mm, 25 mm, 50 mm and 100 mm. As can be seen in FIG. 15A, the extension member 105 can have markings indicated at 418 for monitoring depth in skin, and the markings also can be radiopaque markings.

A probe 400 as in FIG. 15A can be positioned within a body orifice or within any body passageway, opening, cavity, lumen, vessel, sinus or a body wall, membrane or surface layer of a body structure, such as skin. The method can comprise using the insulative extension member 105 of FIG. 15A in any wall, or surface layer of a body structure including an eye, a brain, a sinus, a nasal passageway, an oral cavity, a blood vessel, an arteriovascular malformation, a heart, an airway, a lung, a bronchus, a bronchiole, a larynx, a trachea, a Eustachian tube, a uterus, a vaginal canal, an esophagus, a stomach, a duodenum, an ileum, a colon, a rectum, a bladder, a urethra, a ureter, a vas deferens, a kidney, a gall bladder, a pancreas, a bone, a joint capsule, a tumor, a fibroid, a benign tissue mass, a vascularized tissue mass, hemorrhoid, a tissue mass including a plexus of dilated veins, a neoplastic mass and a cyst. The method can also include positioning or translating the extension member 105 for vapor delivery within a body passageway, body opening, cavity, lumen, vessel or sinus that can comprise an airway, an ear canal, a Eustachian tube, a cervical canal, a vaginal canal, a nasal sinus, an esophagus, a stomach, a duodenum, an ileum, a colon, a rectum, a bladder, a urethra, a ureter, a vas deferens, a fallopian tube, a blood vessel, a milk duct and a lymph vessel.

The probe 400 of FIG. 15A further includes an handle portion 402 configured with on or more other lumens that connect to flow channel 124 or one or more channels in the wall of the extension member 105. For example, fluid source 420 can be coupled to connector 422 and lumen 423 to deliver inflation pressure to a balloon 325 as depicted in FIG. 12C. Still referring to FIG. 15A, another connector 424 and lumen 426 is coupled, for example to a secondary vapor source 160 as described in the text accompanying FIG. 2. It should be appreciated that the hub or handle portion 402 can be configured with from 1 to 10 or more such connections to provide various functions.

The probe 400 of FIG. 15A is configured to have vapor source 120 directly coupled to fitting 407 to provide a flow of vapor 122 through the flow channel 124. It should be appreciated that the probe or assembly 400 of FIG. 15A can be used as an insulative sheath, and an elongated flexible or rigid vapor delivery tool can be introduced through the flow channel to deliver vapor to a targeted tissue. For example, the probe or assembly 400 could be used as a sheath to extend through skin and the wall of a blood vessel, and a vapor delivery catheter can be introduced through the channel 124 for delivery of vapor from a working end of a catheter (not shown).

Figure 15B:
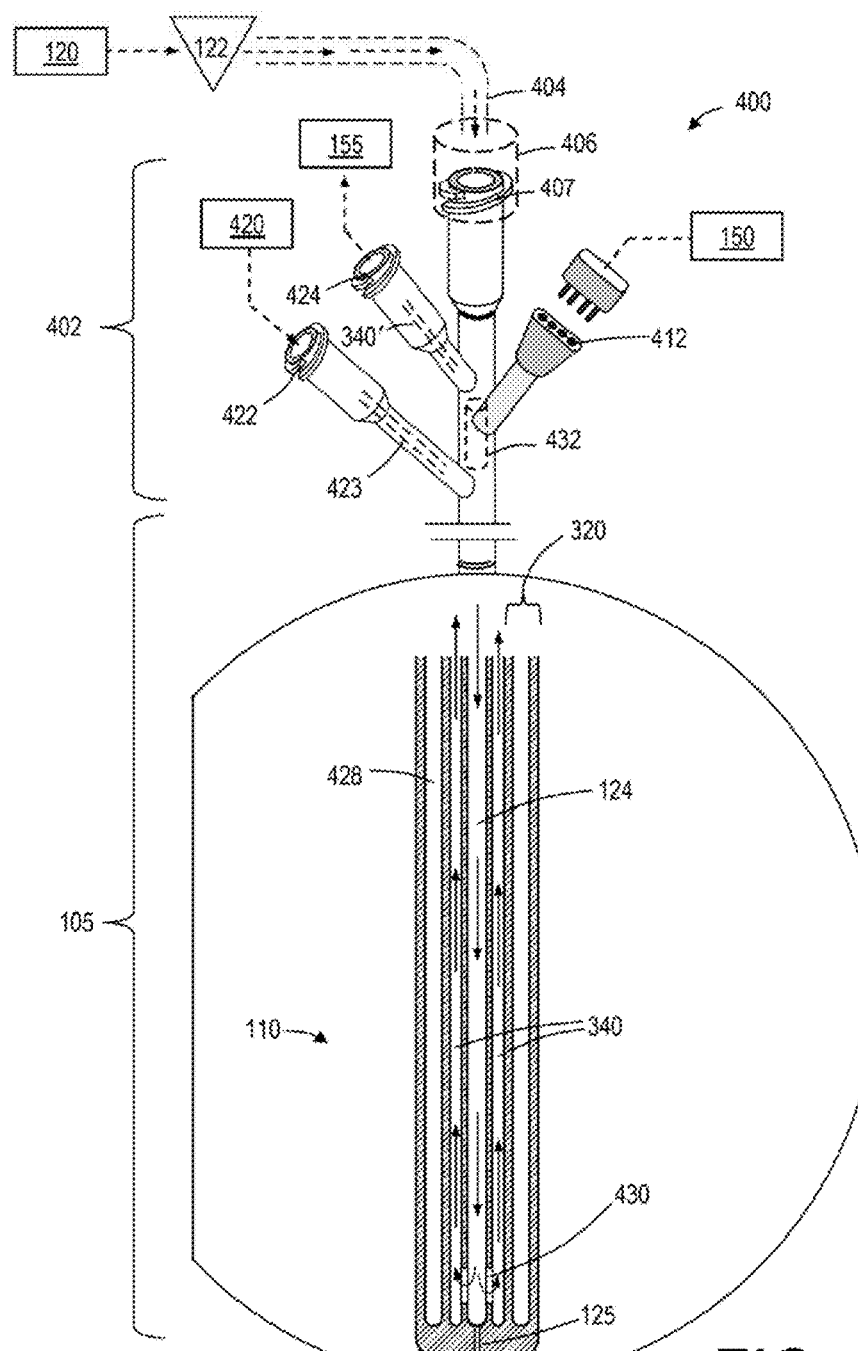
FIG. 15B is a view of another vapor delivery probe similar to FIG. 15A with a cross-sectional view of a different type of insulative wall about a vapor deliver channel.

FIG. 15B illustrates another embodiment of probe 400 with an elongated extension member 105 for vapor delivery that includes an insulative region 320 similar to FIGS. 12D and 15A, which can comprise an concentric air space 428 with an optional aerogel, or a system of recirculation channels. The embodiment of FIG. 15B further includes the recirculation flow channel system and passive valve of FIGS. 14A-14B. In the embodiment of FIG. 15B, the flow channel 124 carries the distal vapor flow toward outlet 125 and the second return channel 340 (cf. FIGS. 14A-14B) is concentric about channel 124. It can be seen in FIG. 15B that one or more openings 430 allow for vapor flow transition and reverse in direction from flow channel 124 to return channel 340. In this embodiment, a solenoid valve 432 in the handle portion 402 is configured to close the return channel 430 to thus cause a distal flow of vapor through the outlet 125 as described in the text accompanying FIGS. 14A-14B. The solenoid 422 is operatively connected to controller 150 by electrical connector 412. In the embodiment of FIG. 15B, a fluid source 420 again is coupled to connector 422 and lumen 423 to deliver inflation pressure to a balloon 325 (not shown) but which is depicted in the embodiment of FIG. 12C. In FIG. 15B, the connector 424 and lumen 340' is coupled to a negative pressure source 155 which is in turn in communication with return channel 340 to provide the passive valve functionality at the working end to cause vapor flow through the outlet 125.

Figure 15C:
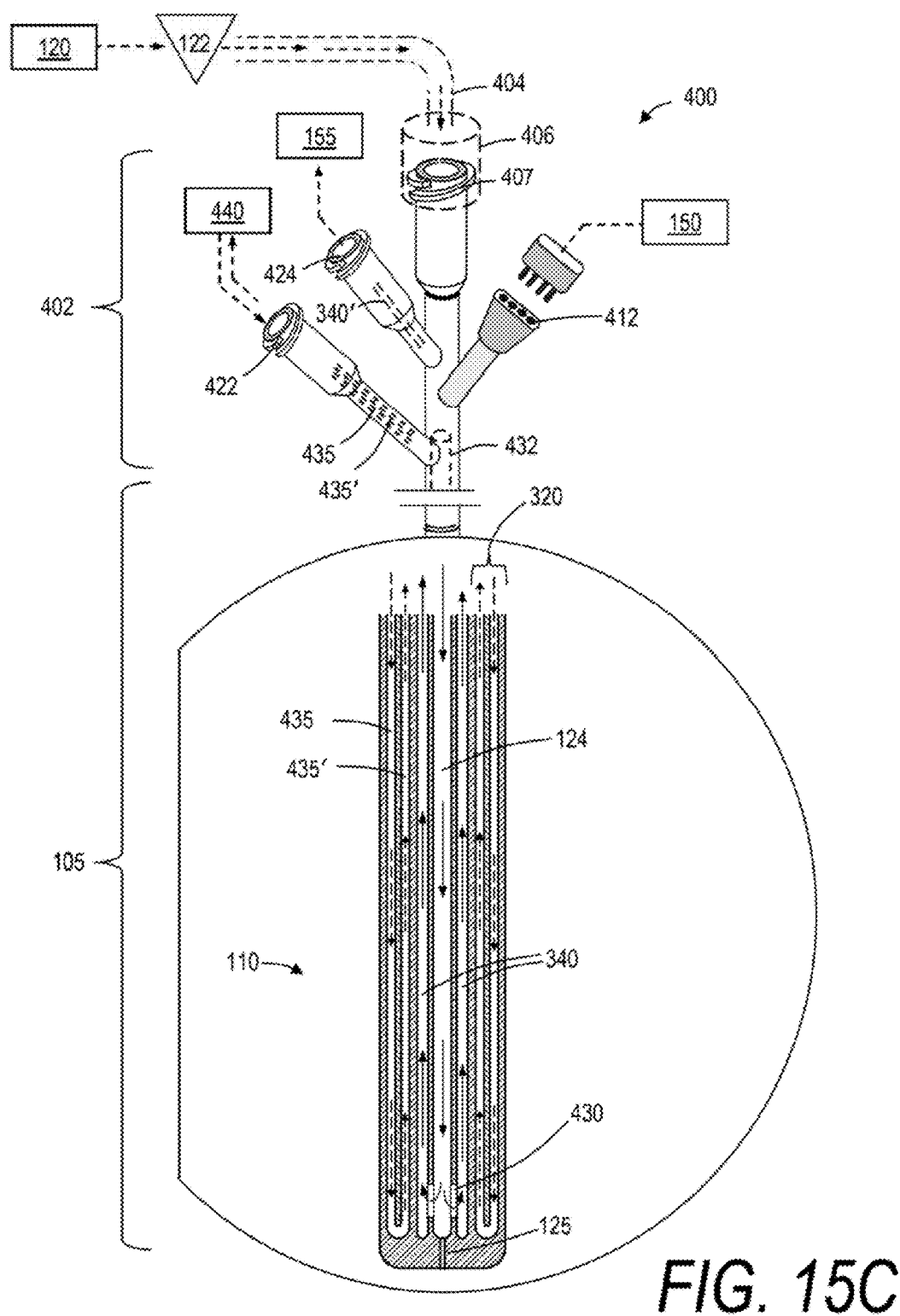
FIG. 15C is a view of another vapor delivery probe similar to FIGS. 15A-15B with a cross-sectional view of a different type of insulative wall.

FIG. 15C illustrates an embodiment of probe 400 that has the same features as the embodiment of FIG. 15B except that the extension member 105 of FIG. 15C includes an insulative region 320 that comprises a concentric system of recirculation inflow and outflow channel portions, 435 and 435' respectively, that are coupled through connector 422 to an inflow/outflow source 440 for providing the fluid flows for cooling the extension member wall. The fluid flows provided by the source 440 can be any gas, liquid, cryofluid or the like, and outflow source of system can further be configured to apply a partial vacuum while at the same time as flowing a gas through the channel portions 435 and 435'. While the inflow and outflow channel portions 435 and 435' are shown as concentric, such lumens can be axial or helical and extend about the vapor flow channel 124.

Figure 15D:
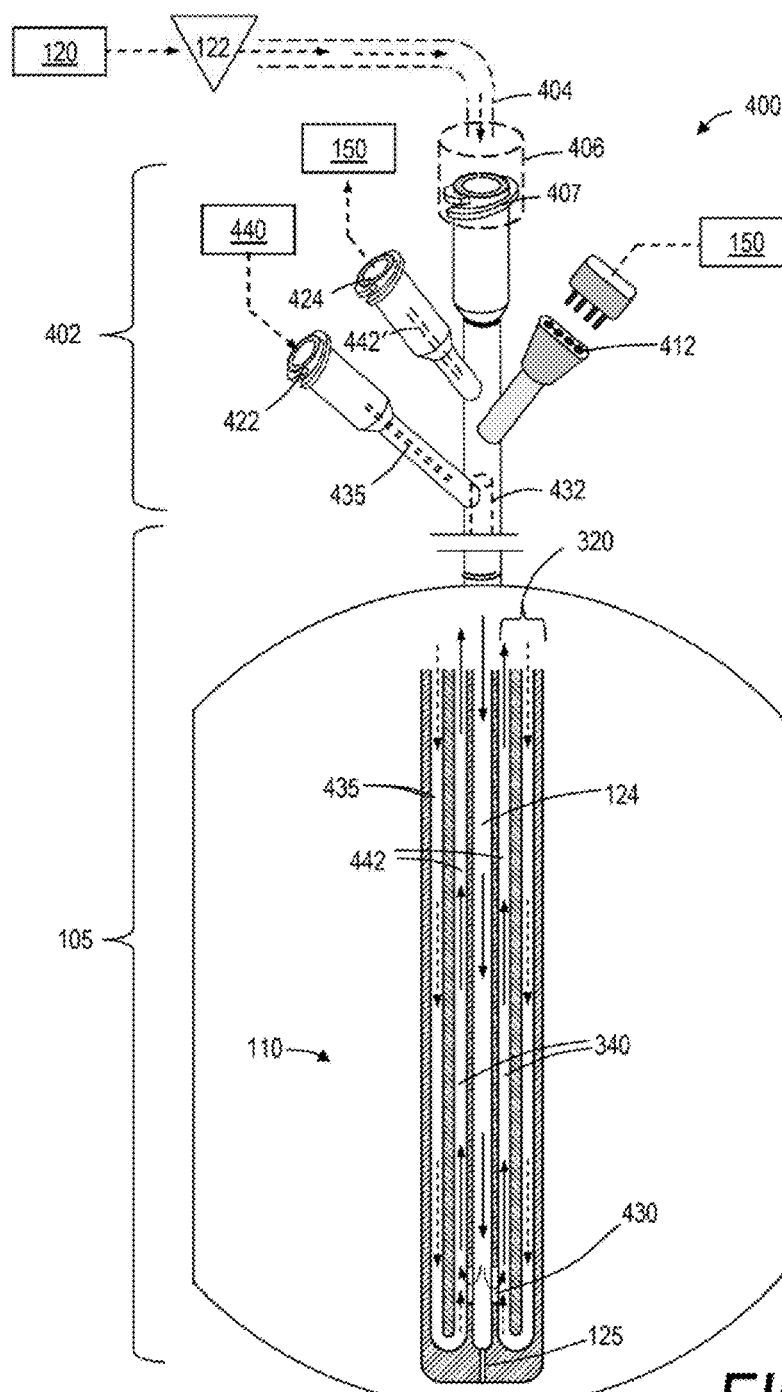
FIG. 15D is a view of another vapor delivery probe similar to FIGS. 15B-15C with a cross-sectional view of a different type of insulative wall.

FIG. 15D illustrates another embodiment of probe 400 that is similar to the embodiment of FIG. 15C except that the extension member 105 of FIG. 15D is configured with a single concentric flow channel 442 for recirculation flows that takes the place of two lumens 340 and 435' in FIG. 15C. It can be seen that flows of vapor 122 will travel distally in flow channel 124 and then through opening 430 to thereafter flow proximally through channel 442 and 442' in the connector to the atmosphere or negative pressure source 155. In this embodiment, the source of cooling fluid indicated at 440 provides a flow of air or other gas that flows distally through connector 422 and channel 435 to the working end 110 and then the cooling gas reverses direction to flow proximally in channel 442 which combines with proximal vapor flows as described above in this paragraph. In this embodiment, the solenoid 432 is configured to channel 442 to cause vapor flows to be forced through outlet 125 which also thus will interrupt cooling gas flows through channel 435. Thus, this system is best suited for treatment methods that require pulsed vapor flows or intermittent vapor flows into a targeted tissue, so that when vapor flows are not directed though outlet 125, the cooling gas will cool the exterior of the extension member 105.

FIGS. 15E-15F illustrate a working end 110 of another embodiment of probe 400 similar to that of FIG. 15D except that a slidable sleeve member 450 is utilized, as a valve to direct flows distally through the outlet 125. As can be seen in FIG. 15E, the sleeve 450 is in a proximal position so that a flow of vapor 122 in channel 124 transitions through openings 430 to thereafter flow proximally through channel 442 as described previously. In this embodiment, the reduced cross-section outlet comprises a microporous material indicated at 455 that permits vapor flow therethrough but prevents flow of water droplets to thereby maintain high vapor quality. The microporous material can be a sintered metal filter with pore sizes ranging from about 10 microns to 200 microns. Further, in one embodiment illustrated in FIG. 15E, the microporous material 455 is a resistively heatable material such as nichrome that is coupled to electrical source 460 and controller 150 by opposing polarity electrical leads 462 and 464 to heat the material. The controller 150 can be configured to heat the microporous material 455 when the slidable sleeve member 450 is advanced as shown in FIG. 15F. In FIG. 15F, it can be seen that advancing the sleeve member 450 distally functions as a valve to close the openings 430 thus forcing the vapor into and through the microporous material 455. At the same time, the microporous material 455 is heated to a temperature capable of vaporizing any micro-droplets of water in contact with the microporous material 455 and outlets 125 therein to enhance vapor quality.

As can be understood, an aspect of the invention is to provide first energy source and heat emitter for converting a liquid media such as water or saline into a vapor media, for example in a handle 102 of the system 100 as shown schematically in FIG. 2. The system can provide a second energy source and emitter such as microporous material 455 in a working end of a vapor-carrying tool or extension member to vaporize any water droplets in a vapor media to thereby provide a high quality vapor with controlled high energy content, such as a vapor that is at least 70%, 80%, or 90% pure water vapor.

One method of the invention for performing a thermotherapy procedure comprises causing a flow of a gas or liquid within a vapor delivery member (e.g., extension member 105 of FIGS. 15A-15F) positioned in a body structure, wherein the vapor delivery member is configured to reduce thermal transfer from a high temperature vapor flow to the body structure. In one embodiment, the vapor delivery member reduces such thermal transfer by providing a flow of a gas or liquid in the vapor delivery member to extract heat or evacuating a gas from a channel of the member to create or enhance a partial vacuum of the channel. Another method of the invention comprises causing a flow of a gas or liquid within a vapor delivery member wherein the flow is provided at a selected pressure provided by a controller 150, and/or wherein the controller is responsive to sensing data from a temperature sensor in the member. The method includes using a thermotherapy probe to provide a flow of vapor through an interior channel of the probe to apply energy to the targeted tissue site. The sleeves can be configured with interior channel portions that are axial, co-axial, concentric and/or helical. The interior channel or chamber can form a closed loop or can have at least one outlet in a surface of the sleeve, for example, to allow leakage of a cooling fluid into an interface with body structure.

Figure 16:
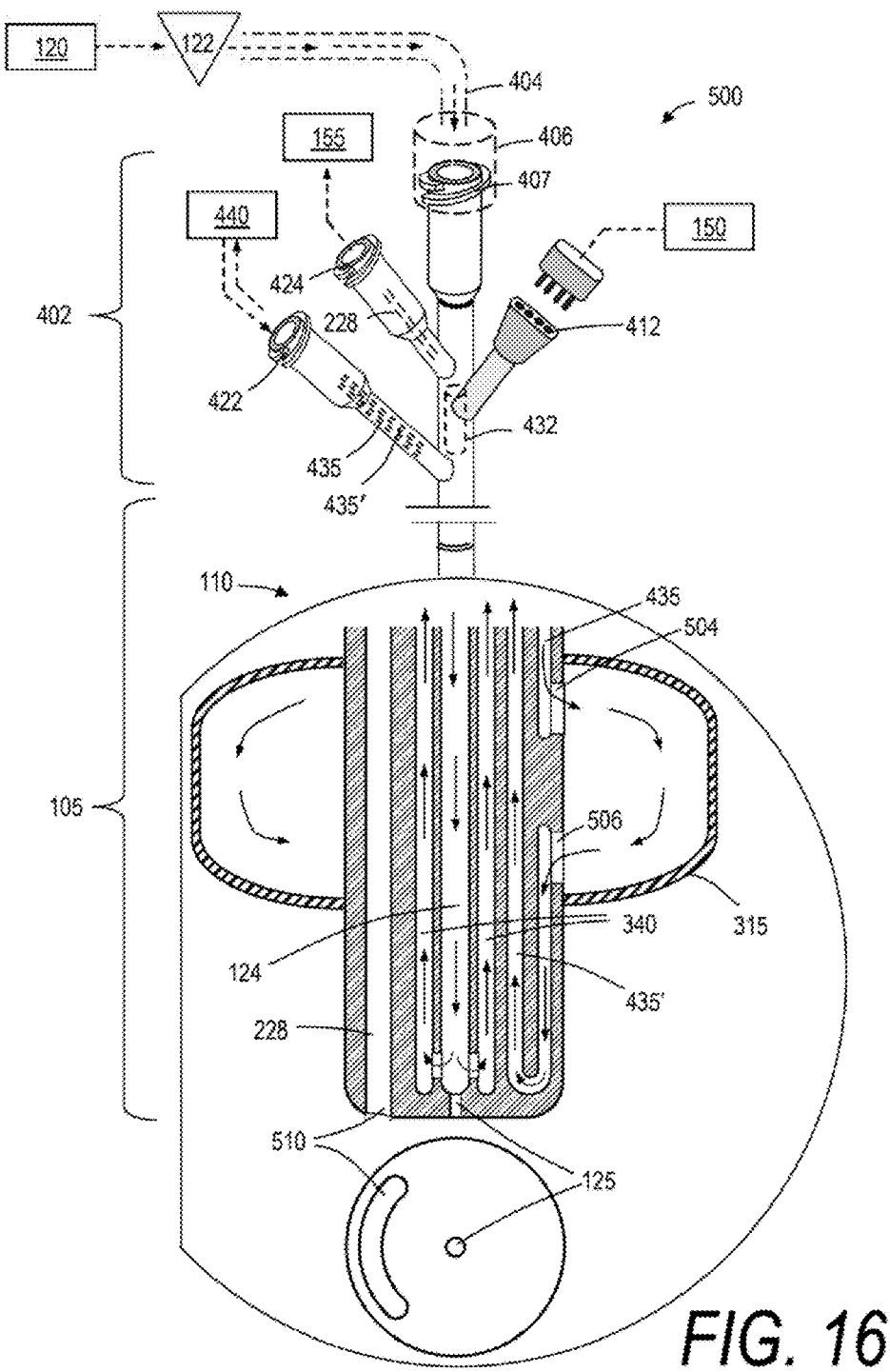
FIG. 16 is another working end similar to that of FIG. 15C including an expansion member.

FIG. 16 illustrates another embodiment of probe 500 that combines features of the embodiments of FIGS. 12C and 15C with vapor flow channel 124 and recirculation channel 340 to provide a passive valve at the outlet 125. The embodiment further includes a source of cooling fluid indicated at 440 that provides a flow of liquid or gas that flows distally through connector 422 and channel 435 to the working end 110 and inflates the balloon 315 and then reverses direction to flow proximally in channel 435' to exit the probe. FIG. 16 illustrates a flow of a fluid into the balloon through port 504 and exiting the balloon through port 506 that communicates with outflow channel 435'. Thus, this embodiment provides a cooling flow through the balloon member 315. In the embodiment of FIG. 16, a negative pressure source 155 as in FIG. 12C is coupled to connector 424 and channel 228 that terminates in at least one open port 510 in the working end. Thus, the controller 150 can modulate pressure with a body cavity by controllably extracting media from the cavity such as a uterine cavity (see FIG. 12C).

Remote Vapor Generation Unit and Control Systems

Now turning to FIGS. 17A-18B, several views of a vapor generation system or source 700 of the invention are shown, which comprises a unit 702 that can be connected with a flexible vapor delivery conduit 705 that extends to a vapor delivery tool or probe (710 or 710') each having a working end (715 or 715'). An exemplary instrument or 710 or 710' can be configured for intraluminal or interstitial energy application as described in previous embodiments. For purposes of clarity, interstitial tissue means the tissue that is adjacent to the interspaces of adjoining tissue while intraluminal tissue is tissue that is adjacent to or surrounding any lumen. The probe 710 has a working end 715 similar to FIG. 12C with a balloon member 325. The probe 710' has a working end 715' similar to FIG. 4A but with multiple extendable vapor delivery needles 717. The vapor delivery flex-sleeve or conduit 705 can be disposable or re-useable. The unit 702 includes a canister or generator 716 with an interior chamber 718 which has a heat source that applies energy to liquid media in the interior chamber to produce a vapor media. Of particular interest, the system 700 is configured to provide a high quality vapor media with precise parameters in terms of vapor quality, exit vapor pressure from the working end 715, exit vapor temperature, and maintenance of the parameters within a tight range over a treatment interval. All these parameters must be controlled with a high level of precision to achieve controlled dosimetry, no matter whether the particular treatment calls for very low pressures (e.g., 1-5 psi) over a treatment interval or very high pressures (200 psi or greater) and no matter whether the treatment interval is in the 1-10 second range or 2 to 5 minute range.

In operation, the system 700 relies on developing a selected pressure in the interior chamber 718 of canister 716 and maintaining the selected pressure which then can drive the vapor through the working end 715 of any type of vapor delivery tool or probe and into an interface with tissue without the need for any vapor pumping mechanism. In one embodiment shown in FIGS. 18A-19, the heat source can comprise first and second resistive heating band elements 720a and 720b about the exterior of a stainless steel canister 716 capable of withstanding high internal pressures. An exterior insulator layer about the exterior of canister 716 is not shown in FIGS. 18A-18B. The unit 702 includes a number of features that allow for production of high quality vapor over an extended period of time at the generator outlet 722 (FIG. 17A), the conduit outlet 724 (FIG. 20) or at least one outlet 125 in the instrument working end 715. In one embodiment, the unit can provide vapor media at a selected pressure between 1 psi and 300 psi over any treatment interval from 1 second to 10 minutes with a variation in pressure of less than 0.1 psi. Stated another way, the system can provide vapor with less that 10% variability, less than 5% variability and less that 2% variability over a treatment interval. By the term high quality vapor, it is meant that the vapor media that is substantially a water vapor that upon a phase change releases at least 300 cal/gm, 350 cal/gm, 400 cal/gm, 450 cal/gm or 500 cal/gm. Stated another way, the term high quality vapor means that a vapor source produces a vapor media that is at least 60% pure vapor, at least 70% pure vapor, at least 80% pure vapor, or at least 90% pure vapor on the based or weight or mass. In one embodiment, the system is adapted for providing a therapeutic effect in a subject and includes an instrument having a working end 715 configured for positioning in a subject, a flow channel 802 (FIG. 21) extending through the instrument to at least one outlet in the working end 715, and a controller 730 and control algorithms operatively coupled to the unit 702 for controlling operational parameters.

Still referring to FIGS. 17A-19, an overview of a method of operating the unit 702 is described next, which includes a number of features and aspects of the system that allow the system to provide precise dosimetry. The unit 702 includes a touch screen or panel 732 and power switch 734. When the switch 734 is in the ON position, power is applied from electrical source 735 (FIG. 17B) to the controller printed circuit board (PCB) indicated at 736, the heating circuitry to energize the heater band elements 720a and 720b, the pump 740 and other components (see FIGS. 18A-19). In one embodiment, the canister also carries an immersion heater (not visible in FIG. 18A) in the interior chamber 718 for allowing raid start allowing up heating of the system. When switch 734 it is in the OFF position, all the power to the unit is turned off. The panel includes an emergency push button switch 741 that when pressed inward, power for the heating system is turned off. When the switch 741 is pulled outward and the emergency reset switch 742 on the touch screen is actuated, power is delivered to relays 744 and the power for the heating system will be applied if the water level in interior chamber 718 has a sufficient water level. If not, the heating circuitry will not be activated until a water level sensor system 750 determines that a sufficient water level has been attained in chamber 718 which then closes the circuit.

Figure 18A:
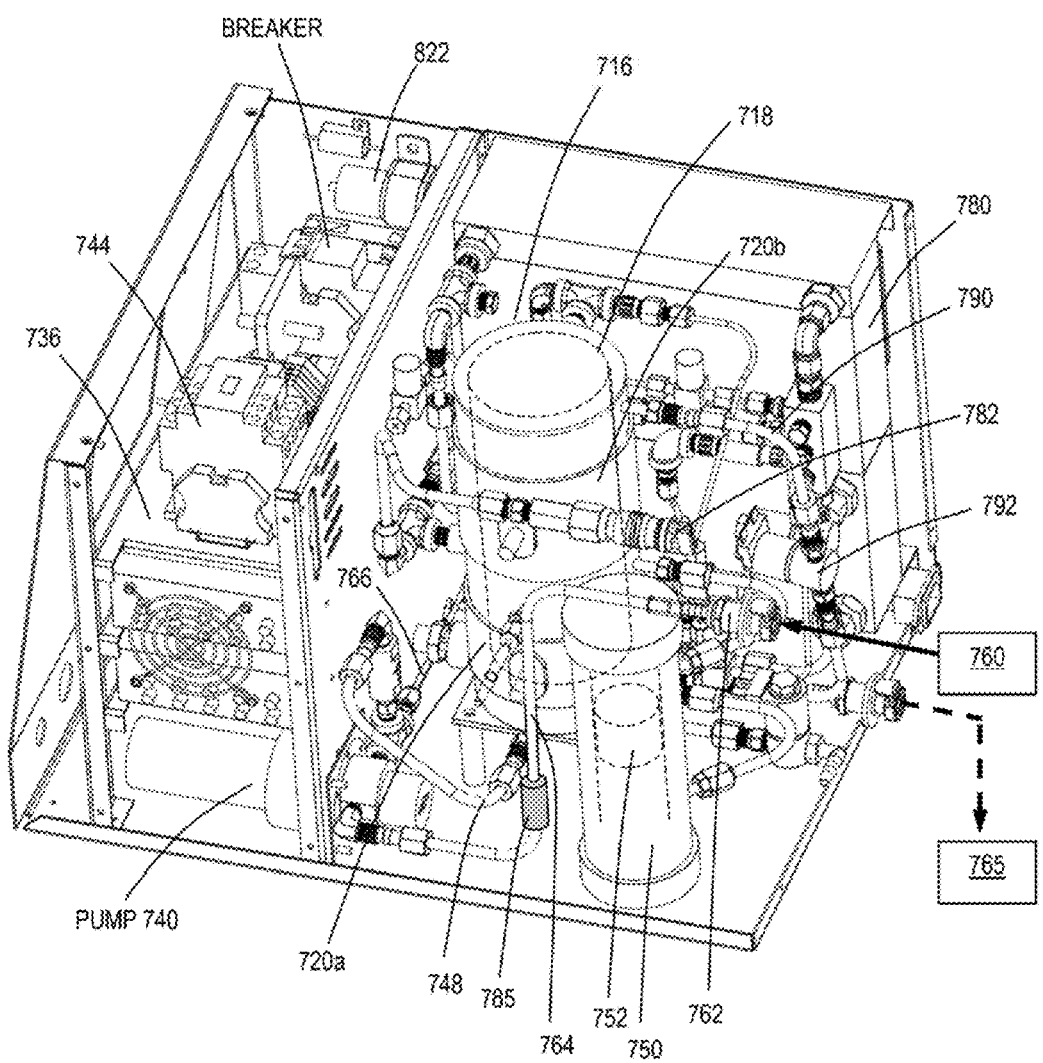
FIG. 18A is perspective view of components of the vapor generator system of FIGS. 17A-17B.
Figure 18B:
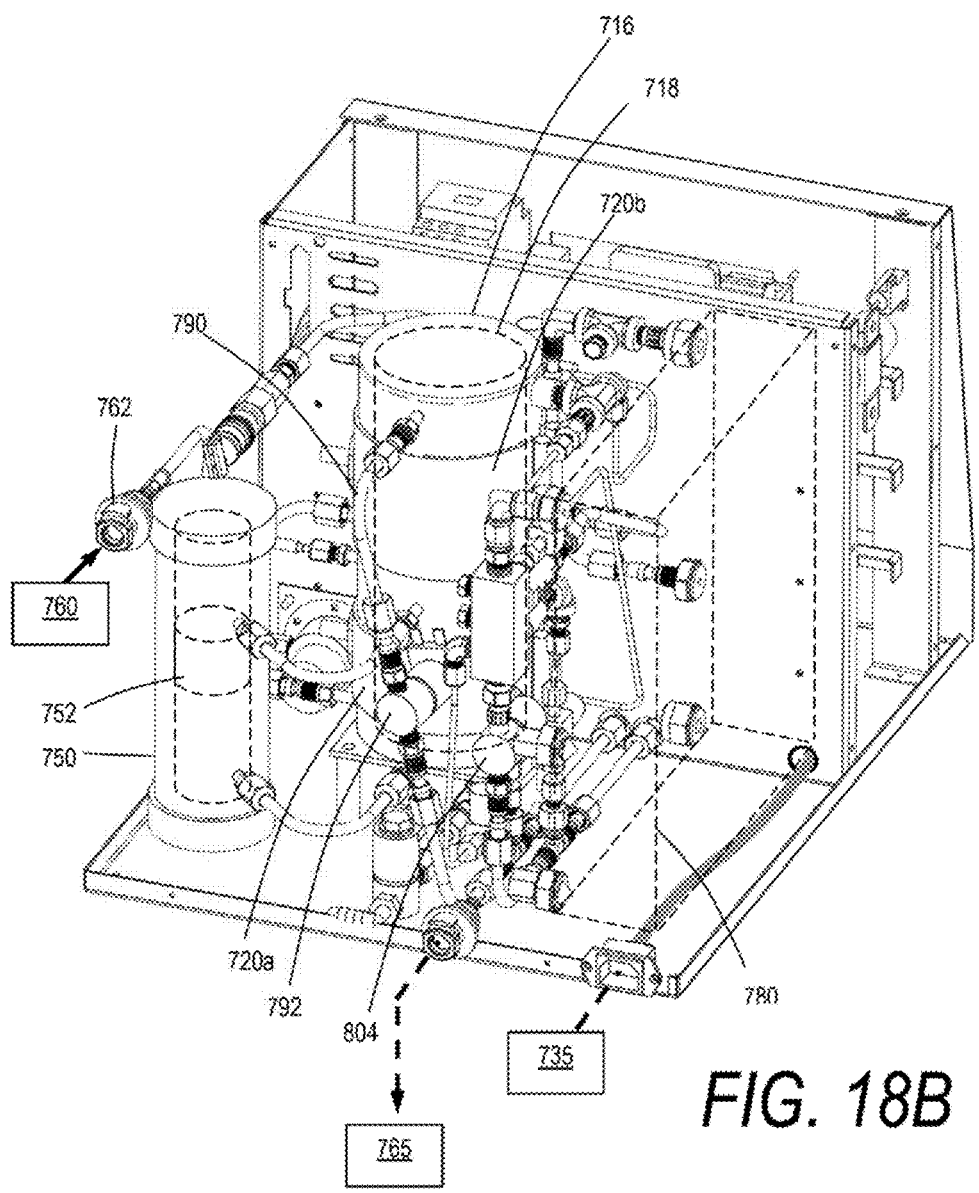
FIG. 18B is another perspective view of components of the vapor generator system of FIG. 17A-17B.
Figure 19:
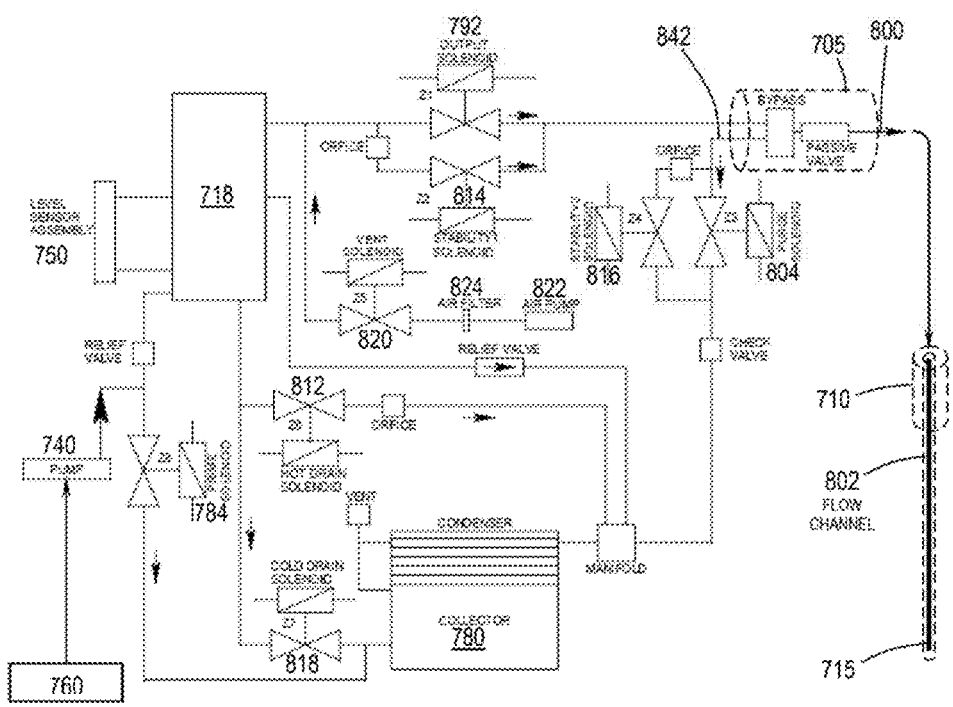
FIG. 19 is a block diagram of components of the vapor generator system of FIGS. 17A-18B.

Referring to FIGS. 18A-19, the water level sensor system 750 can have one or more set points, and in one embodiment is configured with three water level set points wherein the sensor system includes a float 752 or optical level sensors in a chamber in fluid communication with the interior chamber 718 of canister 716. In one embodiment, if the water level is at a first OFF set point, the controller 730 removes power from, or does not permit power application to, the heater band elements 720a and 720b and the immersion heater. When the water level is at a second minimum set point, the pump 740 runs until the water level reaches the third normal set point at which time the pump stops pumping. The heating system can be configured to operate continuously when the water level is between minimum and the normal set points, subject to other functional algorithms described below. In another embodiment, the level sensor system can comprise at least one of a float sensor, an optical sensor, an electrical sensor and a thermal sensor. Multiple systems can be provided for redundancy and safety purposes.

Figure 17A:
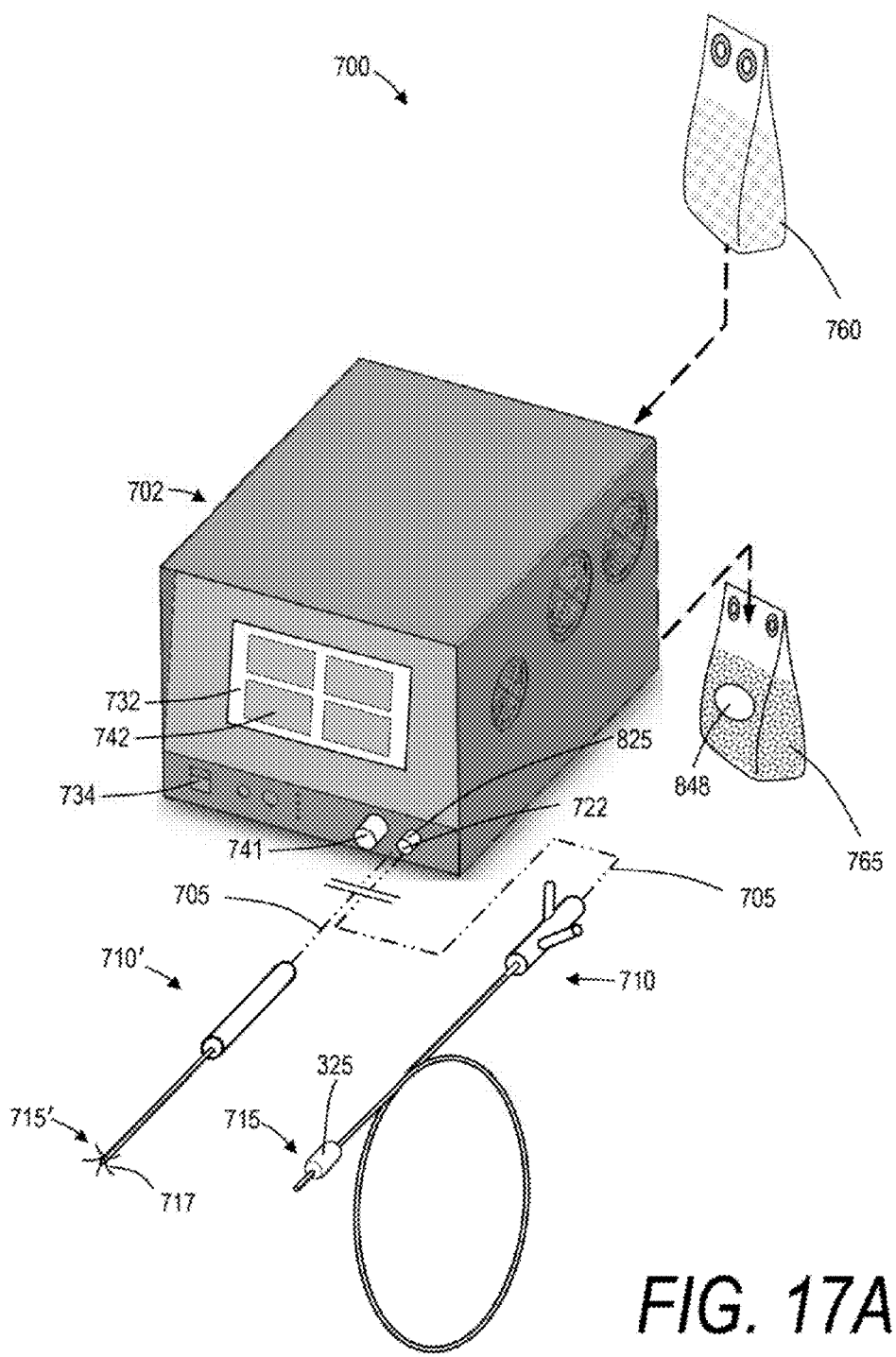
FIG. 17A is another perspective view of the vapor generator system of FIG. 15.
Figure 17B:
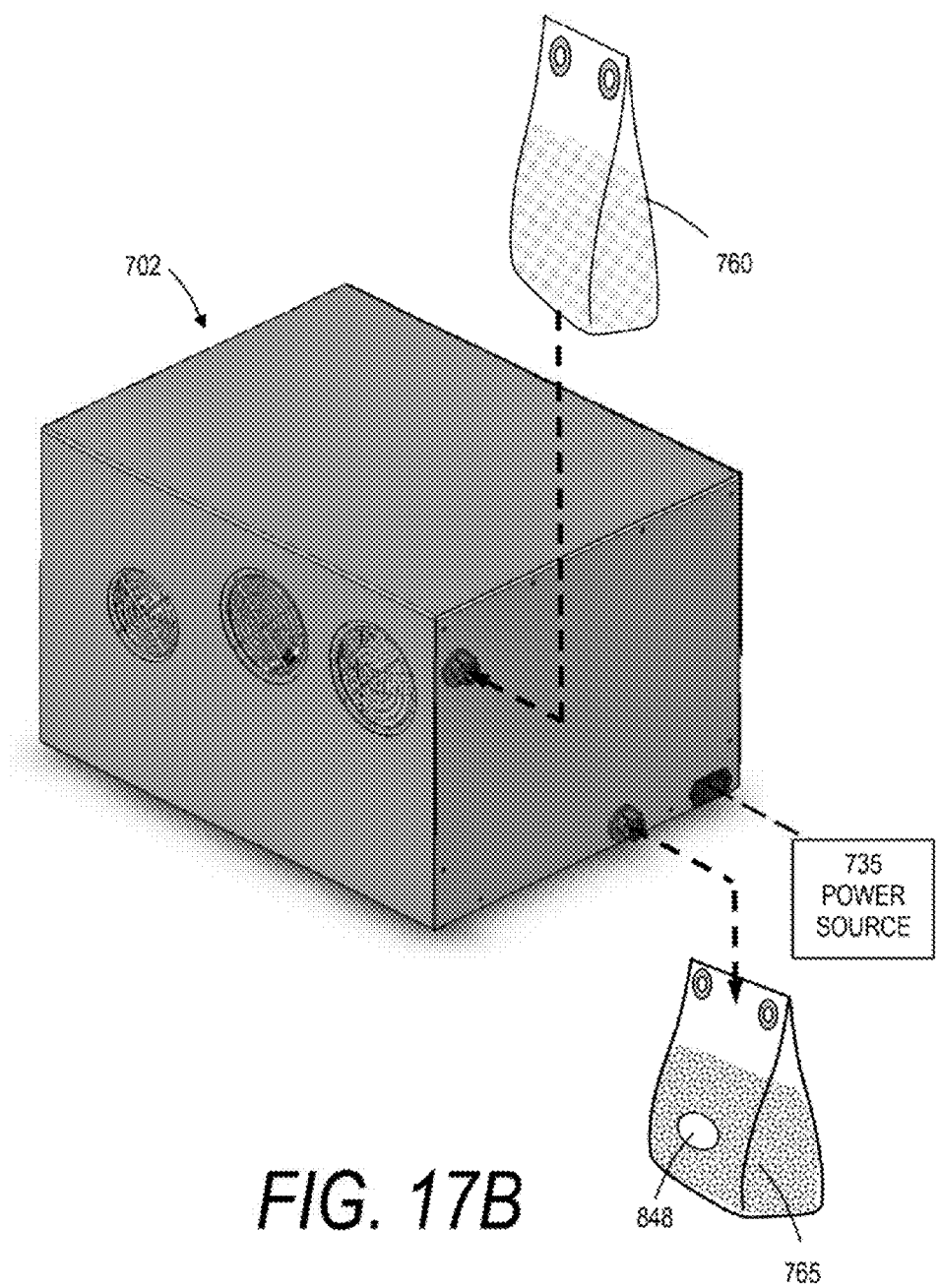
FIG. 17B is another perspective view of the vapor generator system of FIG. 15.

In another aspect of the invention, the unit 702 includes a disposable source of a liquid such as sterile water indicated at 760 in FIGS. 17A-17B. The liquid source 760 can be a commercially available flex-wall sac of sterile water, such as a 500 ml, 1000 ml or 2000 ml bag. The bag can be suspended from any stand or rack to allow a gravity flow of the liquid through connector 762 and inflow channel 764 toward the pump 740. In another embodiment, the liquid container can comprise a plastic sac or bottle particularly adapted for single patient use wherein the container can be disposed of following a single procedure. The system is configured with a connector 762 known in the art that allows change out of the liquid source 760 without interruption of use of the system, or alternatively, the purge system (described below) can be actuated upon changing the liquid source 760. As will be described further below, the system also has a disposable liquid collection sac indicated at 765.

In one embodiment, when the unit 702 is first turned on, the controller 730 activates a priming subsystem which includes a priming outflow channel indicated at 766 that flows to collection and cooling reservoir indicated at 780 in FIGS. 18A-19. In operation, the prime solenoid 784 (FIG. 19) is activated for a short period of time during initial activation of pump 740, for example for 1 to 60 seconds. This priming step provides that air in the outflow from pump 740 is directed through the prime outflow channel 766 in order to prime and relieve the pump, which thus reduces the possibility of unwanted air entering the interior vaporization chamber 718 of canister 716. This priming circuit can be activated when the touch screen button for "prime" is pressed or when an ion sensor 785 described below detects a liquid media having unacceptable quality. In the case of the unacceptable liquid quality, the controller re-directs the liquid into and through the priming outflow channel 766 of the priming subsystem.

In another aspect of operation, the unit 702 has an output circuit with output flow channel 790 which includes an output or delivery solenoid 792 which can be actuated by either a switch on the touch screen, or an instrument actuation switch such as a handswitch or footswitch. In order to actuate the output solenoid 792, the controller 730 includes an algorithm that requires that chamber 718 of vapor canister 716 reach an operating pressure set point and also can require that a flow channel 800 in the conduit 705 (FIG. 19) or a flow channel 802 in instrument 710 reach an operating temperature set point. The operating pressure set point can be any pressure between 1 psi and 500 psi, and in various procedures, optimal pressure or driving pressure has been found to be as low at 5 psi and as high as 250 psi. In one embodiment, a purge subsystem and controller algorithm is provided wherein the purge solenoid 804 is activated when treatment has been initiated, and the output solenoid 792 has also been activated. This can be a very short period of time for the valve to be open, for example from 0.1 second to 5 seconds, resulting in a high velocity purge to remove any residue condensate in the flow channel 800 of the conduit 705 or flow channel 802 of the instrument. The purge subsystem can be activated by the switch on the touch screen 732.

As described above, the unit 702 has a collection and cooling reservoir 780 that is configured to receive remainder liquid media from system operation, which can include liquid from the prime system, from the purge system, from a conduit sterilization system, from the bypass system, and from extracted liquid from the working end 715 of an instrument. The cooling, system includes a heat exchanger and fans as is known in the art to cool the liquid and upon sensing a cooled temperature with a temperature sensor. The controller 730 is configured to open a discharge or drain solenoid 812 to discharge the remainder liquid into the collection sac 765 (see FIGS. 17A-19).

In one embodiment, the unit 702 includes a liquid quality detection means for detecting water quality from source 760 which can be an ion sensor indicated at 785 in FIG. 18A. The ion sensor comprises spaced apart electrodes that sense a parameter of the liquid inflow such as impedance and/or capacitance which is determinative of sterile water. If the sensor detects impure water, the controller 730 can further include an algorithm to run a prime cycle when a new liquid source 760 is connected to the unit 702 to purge any impure water from the system through the priming outflow channel 766. As described above, this remainder liquid is then directed to the collection and cooling reservoir 780. A method of the invention utilizes the sensor system to provide a read-out of an ion level in the liquid media, and can include an algorithm that disables the system with a system lock-out that requires a new liquid source to be connected to the system to overcome the lock-out.

In another embodiment, the system includes a stability subsystem and circuit, wherein stability solenoids 814 and 816 can be used to actuate a heating system in flow channel 800 in the conduit 705 and optionally the flow channel 802 in instrument 710 (FIG. 19). This system and method reduces condensation in the output channels 790 to ensure more accurate and consistent treatment dosimetry, particularly at lower treatment durations. This system also helps maintain sterilization of the delivery tube during the idle phases of the system. The solenoids 814 and 816 also can be energized by a switch on the touch screen 732 and can be controlled to the temperature set point which is programmed into the controller 730. In one embodiment, the stability subsystem includes multiple temperature sensors, both at an interior of the flow channel 800 and at an outer layer of the structure surrounding the flow channel (see FIG. 20) to thereby determine the heat capacity of the structure and losses that may occur in the flow channel 800.

In another aspect of the invention, the unit 702 provides for a hot drain subsystem (FIG. 19). The drain or discharge solenoid 812 is activated by switch on the touch screen 732 at the temperature set point and the pressure set point. This subsystem can use the vapor pressure stored in the tank to drive remainder liquid out the lower portion chamber 718 of canister 716. In operation, the hot drain subsystem is used to remove liquid from the unit after use when the system is to be shut down for any period of time. In use, the hot drain subsystem causes the liquid to flow to the cooling reservoir 780 for cooling as described previously.

In another embodiment, the system provides a cold drain subsystem (FIG. 19). In this embodiment, the cold drain solenoid 818 is activated by a switch on the touch screen 732 which is enabled when pressure in the canister is low, for example between 0 and 1 psi. In a cold shut-down, solenoid 820 and an associated air pump 822 is configured to provide about 1 psi air through a 0.2 micron air filter 824 to the interior chamber 718 of the canister wherein the sterile air pushes out liquid to the collection reservoir and cooling system 780. A cold shut-down can be required for example when there is a power outage. In one embodiment, the air pump system 722 includes a battery back-up.

In general, one embodiment of the invention comprises a medical system for providing a therapeutic effect in a subject that includes an instrument having a working end configured for positioning in a subject, and a flow channel extending through the instrument to an outlet in the working end, a vapor source capable of providing a vapor flow at the outlet, and a controller operatively coupled to the vapor source for controlling operational parameters wherein the vapor source is capable of providing at least 60% water vapor, at least 70% water vapor, at least 80% water vapor or at least 90% water vapor.

As described above, in one embodiment, the system 700 is configured with a number of subsystems that allow for the production of high quality vapor. Thus, the controller 730 includes algorithms for controlling the system's operations, which include: (i) algorithms that control a treatment cycle for delivering vapor media to the instrument and tissue; (ii) algorithms that which control a modulation cycle for modulating vapor media parameters in response to feedback signals of pressure, temperature, and/or vapor flow rates; (iii) algorithms that which control a pump cycle for pumping a liquid media into the vapor source; (iv) algorithms that which control a sensing, cycle for determining sterility of liquid media prior to introduction; (v) algorithms that control a rejection cycle for rejecting liquid media prior to introduction to the vapor source; (vi) that control a priming cycle for priming the pump to prevent air flow to the vapor source; (vii) algorithms that control a purge cycle for eliminating condensation in system channel portions and for maintaining system readiness between multiple uses; (viii) algorithms that control a liquid level control cycle for maintaining a liquid volume in the vaporization source; (ix) algorithms that control a cooling cycle for cooling remainder liquid media; (x) algorithms that control a collecting cycle for collecting remainder liquid media; (xi) algorithms that control a check cycle for checking the system for leakage; (xii) algorithms that control a stabilization cycle for evaluating stability of the vapor quality; (xiii) algorithms that control a sterilization cycle for sterilizing a conduit for coupling the vapor source to an instrument; (xiv) algorithms that control a shut-down cycle for hot shut-down of the vapor source; (xv) algorithms that control a cold shut-down of the vapor source; (xvi) algorithms that control an emergency shut down cycle; (xvii) algorithms that control a sterilization cycle for sterilizing the interior chambers and channels of the system; and (xviii) algorithms that control a drying cycle for drying the vapor source with sterile air.

Other system embodiments include controller algorithm adapted for other system functionality that may not be directly related to vapor quality but nevertheless are directly related to dosimety and treatment intervals, such as: (i) algorithms that control an imaging cycle for actuating an imaging, system; (ii) algorithms that control a modulation cycle for modulating vapor media parameters in response to imaging; (iii) algorithms that control an injection cycle for injecting a pharmacological agent through the instrument; (iv) algorithms that control an injection cycle for injecting gas to alter mass average vapor temperature; (v) algorithms that control an aspiration cycle for aspirating media through the instrument, (vi) algorithms that control an actuation cycle for actuating a working end component; (vii) algorithms that control an actuation cycle for actuating at least one heating system in a flow channel in a working end, and (viii) algorithms that control vapor media flow between multiple working end components for controlling the geometry of treated tissue.

Figure 20:
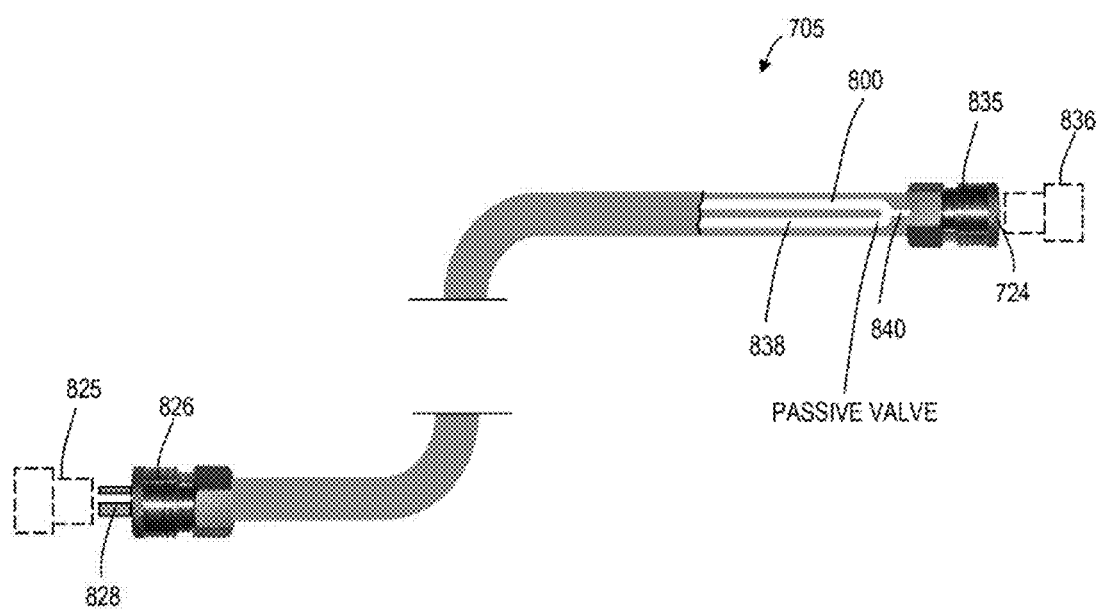
FIG. 20 is a schematic view of a flexible vapor conduit of the vapor generator system of FIG. 17A.

In one embodiment referring to FIG. 20, a medical system as described above includes a sterilizable vapor delivery flex-tube or conduit 705 with an interior conduit flow channel 800 configured to receive the vapor media from a vapor source and transport the vapor media to instrument 710 with working end 715 configured for positioning at a targeted site in a subject. The vapor source unit 702 includes connector 825 (FIG. 17A) that is configured for detachable connection to proximal quick-lock connector 826 on conduit 705 which in one embodiment is keyed with elements 828 to connect at least first and second flow channels (not shown) in unit 702 to a cooperating vapor flow channel 800 in the conduit 705 and at least one other flow channel. The distal end of the conduit 830 has a distal quick-lock detachable connector 835 that is configured for connection to cooperating connector 836 on an instrument or probe 710 (FIG. 17A) having a vapor flow channel 802 therein. In one embodiment, the conduit flow channel 800 is configured for a looped flow from flow channel 800 to return channel 838, which is similar to the system of FIGS. 14A-14B to provide a sterilization circuit. In operation, this looped flow functions as a passive valve as indicated in FIGS. 19-20. The conduit 705 includes a distal outlet flow channel 840 which delivers vapor to the vapor channel 802 in instrument 710. The looped flow can be accomplished with either concentric or laterally spaced apart channels. As can be seen in FIGS. 19-20, the return flow channel 838 of the conduit couples with a return channel 842 (FIG. 19) in the unit 702 that leads to the cooling and remainder liquid collection reservoir 780. In another embodiment, the looped flow portion can be detachable (not shown) from the conduit 705 and can be disposable, wherein the conduit could then be sterilizable by vapor flow though the inflow and outflow channels for a requisite time. Similarly, the looped flow portion or a similar detachable member can be fitted to outlet fitting 825 on unit 702 to allow sterilization of the flow channels in the interior of the unit 702.

In one aspect of operation relating to the cooling and collection reservoir 780, a method for providing a therapeutic effect comprises positioning a working end of an instrument at a targeted site in a subject, actuating a vapor generator to convert a flow of liquid media into a flow of vapor media, introducing the flow of vapor media through a flow channel in the instrument to an outlet in the working end thereby applying energy to the targeted site, and collecting remainder liquid media in a disposable container in fluid communication with the vapor generator and/or the instrument. The can include cooling the remainder liquid media prior to the collecting step. The method includes utilizing a controller 730 and control algorithm for controllably cooling the remainder liquid media and opening a valve to allow collection of the remainder liquid. The method includes cooling the remainder liquid media to less than 80° C., 70° C., 60° C. or 50° C. Further, the method can include condensing remainder vapor media into liquid media prior to the collecting step, collecting excess liquid media from the vapor generator, collecting liquid media following a sterilization cycle, collecting liquid media following a vapor generator shut-down. Further, the method can provide first and second control algorithms for controllably collecting cooled remainder liquid or heated remainder liquid, respectively.

In one embodiment, the medical system provides cooling and collection subsystem that includes a disposable container 765 in communication the vapor generator and/or instrument for receiving remainder liquid media, wherein the container has a wall that is transparent or translucent and is capable of withstanding liquid media temperatures of 70° C., 80° C., 90° C. or 100° C. The disposable container 765 can have a capacity of at least 250 ml, 500 ml or 1000 ml. In one embodiment, the disposable container 765 has wall or wall portion including a thermochromic material 848 for indicating a temperature of the contents (FIG. 17A).

Figure 21:
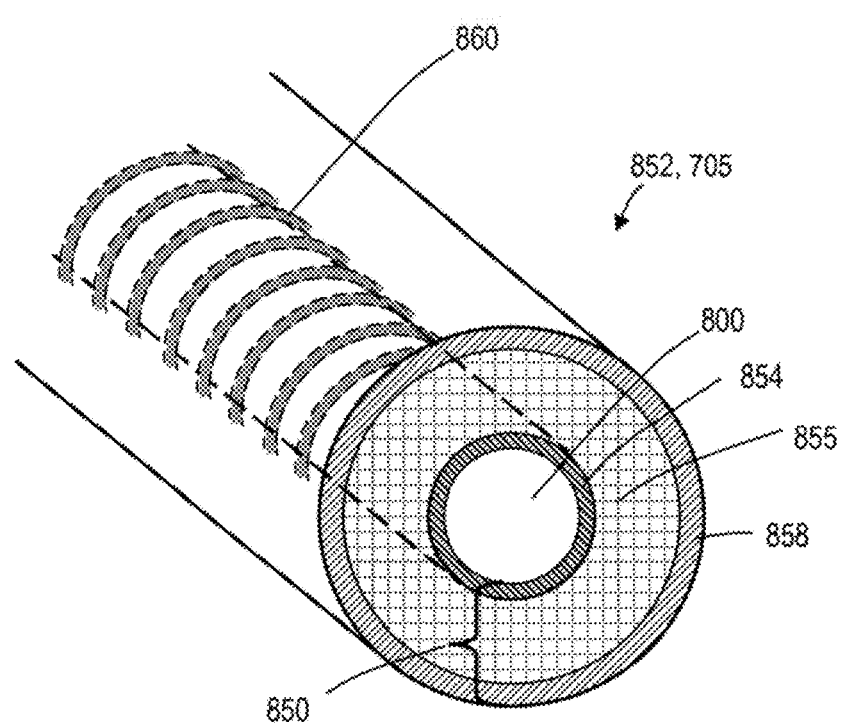
FIG. 21 is a sectional view of a vapor flow channel and surrounding structure used with the vapor generator system of FIGS. 17A-18B

In another aspect of the invention, the medical system as described above provides a vapor media outflow channel 790 from the chamber 718 wherein the channel can have a portions of the flow channel in the unit 702, the conduit 705 and the instrument 710. Referring to FIG. 21, a cross section of a flow channel 800 and surrounding structure or wall 850 is shown in a component indicated at 852 which may be conduit 705 or any other part of the system. In one embodiment, the structure includes a thin inner layer 854 around the flow channel which is of a biocompatible fluid impermeable material such as a polymer (Teflon®) or a metal such as stainless steel. Flexible sleeves can include an electroless plating over a polymer base to provide layer 854. Outward from the inner layer 854 is an insulating layer 855 that can comprise a silica aerogel, hollow glass microspheres, air channels or voids having a partial vacuum, or any other insulation materials known in the art. The exterior 858 of the wall 850 can be any suitable layer, and can include a Nomex material. In one embodiment, the insulative layer 855, or the inner layer 854 and insulting layer 855, or the entire wall 850, as described above, can have a thermal conductivity of less than 0.05 W/mK, less than 0.01 W/mK or less than 0.005 W/mK, in another aspect of the invention, the wall is configured with a material around the channel having a heat capacity of less than 2000 J/kgK. In one embodiment, there are no fittings, surfaces or materials interfacing the flow channel 800 that have a substantial heat capacity, thus preventing condensation. Alternatively, fittings and surfaces can be fitted with a heating element.

In another aspect of the invention, the medical system has a probe and/or conduit having a flow channel 800 extending therethrough from a first end to an open second open, wherein a wall of the flow channel is configured to limit energy losses in a water vapor flow between the first end and the second end to less than 500 cal/gm. In another embodiment, the wall is configured to limit, the energy losses to less than 250 cal/gm, less than 200 cal/gm, less than 150 cal/gm, less than 100 cal/gm or less than 50 cal/gm.

In another aspect of the invention, the medical system includes a probe and/or conduit having a flow channel extending therethrough from a first end to an open second open, wherein the wall of the flow channel configured with at least one heating element 860 (FIG. 21) to limit energy losses in a vapor flow between the first end and the second end. In one embodiment, the wall is configured with at least one resistive coil heater, an inductive coil for heating a wall layer such as an magnetic-responsive electroless plating, a conductive and resistive polymer coupled to an electrical source, or a polymer having a positive temperature coefficient of resistance coupled to an electrical source. The probe member can be rigid or flexible.

In another aspect of the invention, the medical system provides a vapor source, a flow channel having a first end in communication with the vapor source and a second open end in an instrument working end, and structure surrounding at least an intermediate portion of the flow channel between the first end and the second end that is configured to limit energy losses in a vapor flow to less than 50%, 40%, 30%, 20% or 10%. The length of the flow channel can greater than 50 mm, 100 mm, 200 mm or 500 mm. In another aspect, the structure surrounding at least an intermediate portion of the flow channel between the first end and the second end comprises a first surface layer and a second subsurface layer having a substantially low heat capacity. For example, the heat capacity is less than 2000 J/kgK. In one embodiment, an interior layer of the wall comprises an aerogel.

In a method of use, the system can be used to treat a targeted sites that is interstitial, topical or within at least one of a body space, passageway, lumen, cavity, duct, vessel or potential space. A method of the invention for to treating a targeted sites that can be interstitial, intraluminal or topical includes providing a vapor source consisting, of a pump configured for providing a flow of liquid media from a liquid media source into a vaporization chamber having a heating, mechanism, actuating the pump to direct a liquid media flow through an inflow channel between the liquid source and the pump, and applying energy from the heating mechanism to convert a substantially water liquid media into vapor media and controllably introducing said vapor into an interface with tissue to cause the intended effect, wherein the vapor media is at least 60% water vapor, at least 70% water vapor, 80% water vapor or at least 90% water vapor. The method includes applying energy with media in which the percentage of water vapor varies of less than 10% over 5 minutes, 10 minutes, 30 minutes, 60 minutes and 120 minutes. The ability of the system to produce vapor without variation is critical for a controlled dosimetry, which is needed for both interstitial treatments, and treatments of a body lumen, cavity, passageway, vessel, conduit, space or potential space. In another method, the system can be used to treat bone, for example to ablate tumors in a bone, to ablate bone marrow, or to cause surface coagulation and sealing of a bone.

Figure 22:
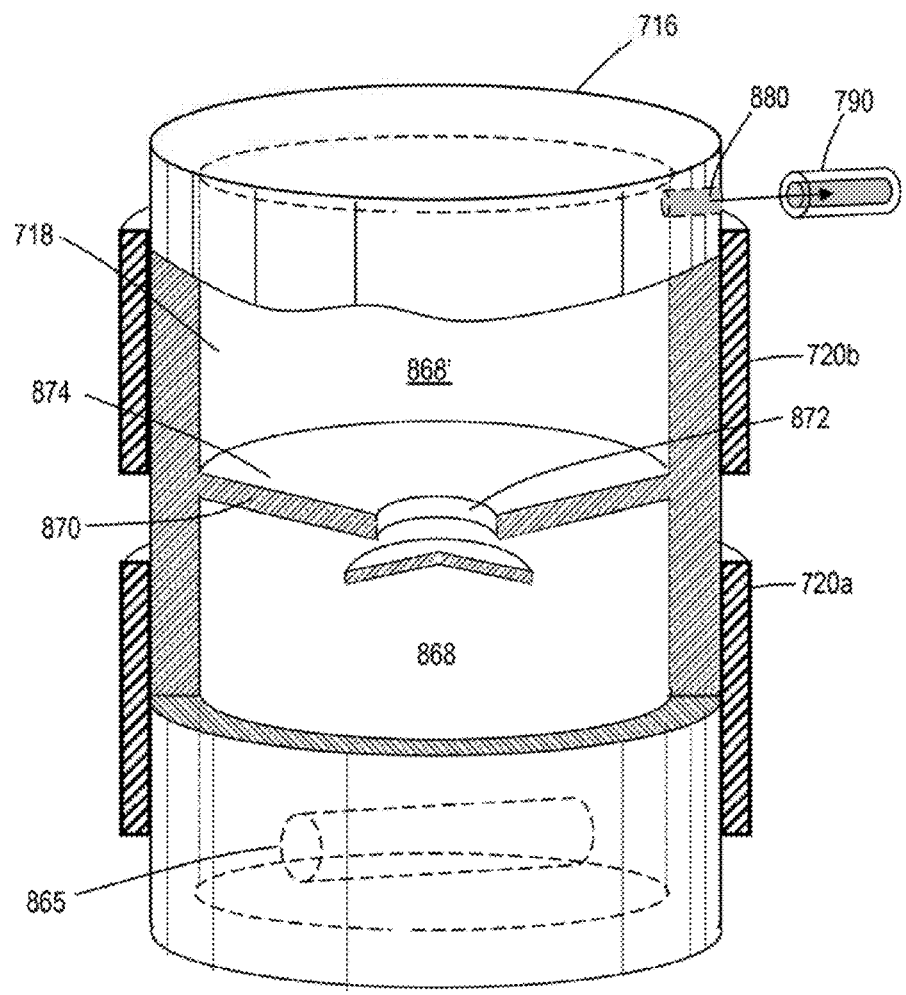
FIG. 22 is a cut-away view of a vapor canister and multiple heating systems of the vapor generator system of FIGS. 17A-18B.

In another method of the invention, a pharmacological agent can be introduced into a targeted site prior to the controlled introduction said vapor to the site. In one example, an anti-inflammatory agent can be introduced through the vapor probe prior to vapor delivery, such as in a lung or airway treatment, a prostate treatment, a uterine treatment, a fibroid treatment, an endovascular treatment or in any tumor ablation. The method also can introduce the pharmacological agent into a targeted site mixed with vapor media. The pharmacological agent can be an anti-inflammatory agent, an antibiotic or an anesthetic agent.

In another method of the invention, the medical system includes a controller configured to control an operational parameter, which can include liquid media flow rate into the interior chamber 718 for conversion to vapor, the liquid media pressure, the liquid media temperature, the vapor media flow rate which is created by the vaporization parameters, the vapor quality as described above, the vapor pressure in the working end and the vapor temperature at the working end. In one embodiment, the system can have multiple heating systems, for example in FIGS. 18A, 18B, 19 and 22, the interior chamber 718 can be configured with a first immersion heating system 865 and a second heating system comprising lower band heating element 720a which allow for rapid start-up of the system to operational parameters, for example in less than 5 minutes, less than 4 minutes, less than 3 minutes or less than 2 minutes. As can be seen in FIG. 22, the interior chamber 718 of canister 716 has a first lower chamber portion 868 and second upper chamber portion 868' which are separated by any suitable configuration of member or baffle 870 with an open region between the lower and upper chamber portions to allow upward vapor flow and downward condensation flow, and can be at least one central opening indicated at 872. In one embodiment, the upper chamber portion 868' is configured with a third heating system or band heater 720b to maintain vapor in the upper chamber as the vapor exits through outlet 880 into delivery tube 790. In operation, the baffle 870 functions as a splash guard to prevent boiling liquid from splashing into the upper chamber while the at least one opening 872 cooperates with a sloped surface 874 of the baffle to allow any condensation to drip back into the lower chamber 868. As can be seen in the schematic drawing of FIG. 22 and FIG. 21, the conduit 705 can be configured with a fourth heating system 860, and the flow channel in an instrument 710 can be configured with a similar or fifth heating system (see FIG. 21), all functioning in accordance with controller 730 to maintain or enhance vapor quality as the vapor flows from the chamber 718 to an outlet 725 in working end 715. In one embodiment, the interior chamber 718 includes a piezoelectric pressure sensor (not shown) coupled to the controller 730.

In another method of the invention, the system operator uses an imaging system to acquire images or other data concerning a site targeted for energy delivery to thereby derive at least one selected site treatment parameter, and from this data determines energy dosimetry. Following this determination, the vapor media is introduced into the site wherein the vapor media is configured to undergo a phase change to thereby apply a predetermined energy dose to the site to provide an intended effect. The derived site parameter can be volume of tissue of the targeted site, for example in a prostate treatment. Alternatively, the derived site parameter can be surface area or cavity volume of the targeted site, for example in a global endometrial ablation treatment. The derived site parameter can be volume or weight of tissue of the targeted site, for example in a prostate treatment, lung treatment, or tumor treatment. In other related methods, the site parameter can be at least one of the heat capacity of tissue of the targeted site, the thermal diffusion characteristics of tissue of the targeted site, the heat sink characteristics of tissue of the targeted site, the fluid content or mobility within a targeted body structure, the volume of any cavity of any targeted organ, the cross section of a lumen of a vessel, the hydration of tissue of the targeted site, the geometry of the targeted site, or the blood flow within the targeted site. The targeted site that can be images can be any of the following: a sinus, a nasal passageway, an oral cavity, a blood vessel, an arteriovascular malformation, a bean, an airway, a lung, a bronchus, a bronchiole, a collateral ventilation pathway in a lung, a larynx, a trachea, a Eustachian tube, a uterus, a vaginal canal, a cervical canal, a fallopian tube, an esophagus, a stomach, a duodenum, an ileum, a colon, a rectum, a bladder, a urethra, a ureter, a vas deferens, a kidney, a gall bladder, a pancreas, a bone, a joint capsule, a tumor, a fibroid, a neoplastic mass, brain tissue, skin, adipose tissue, an ovary, a cyst, a retina, a potential space between body structures and a lower vapor-permeable region adjacent a higher vapor-permeable region.

In the method described above, the imaging step can be accomplished by at least one of ultrasound, x-ray, MRI, PET and CAT scan, or thermal imaging system. The resulting dose can be applied over an interval of at least 0.1 second, 1 second, 5 seconds, 10 seconds, 30 seconds, 60 seconds, 120 seconds and 240 seconds. The method and dose can apply energy in the range of from 0.1 Watt to 1000 Watts. The method of determining dosimetry can be performed independent of the applying energy step. In another method, the determining dosimetry step can be performed contemporaneous with the applying energy step. Also, the method can include contemporaneous determination of dosimetry with the imaging step which provides feedback to adjust dosimetry. In one method, vapor is introduced into a targeted site in the subject wherein the vapor media is configured to undergo a phase change thereby applying energy to provide an intended effect, the targeted site is imaged contemporaneous with applying energy, and the dose of applied energy is modulated in response to data obtained from the imaging step. The modulating step can include controlling the interval of applying energy, controlling the temperature of the vapor media, controlling the pressure of the vapor media and controlling the quality of the vapor media.

In one method, the a heat applicator is introduced into a targeted site in the subject, and the targeted site is imaged with a microbolometer carried at a working end of the heat applicator at least one of prior to, contemporaneous with, or after applying energy and optionally modulating the dose of applied energy in response to data obtained from the microbolometer imaging step. The modulating step can be based on a controller and algorithm, or based on an operator's visual assessment. The modulating step can be configured to apply energy to maintain an average temperature, or to not exceed a peak temperature, can compare pre-treatment temperature to intraoperative temperature. The method can utilize the microbolometer to produce an intraoperative thermogram still image or video images of a body structure to thereafter link to the controller for modulating energy application. Thus, a device of the invention comprises an instrument having a working end with a heat applicator and a microbolometer chip carried by the working end. Further, the working end is configured for positioning in a subject, and has a flow channel extending through the instrument to an outlet in the working end, and the heating mechanism is capable of converting a liquid media into a vapor media in an interior chamber of the system for introduction into the flow channel.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A medical system for delivering high temperature condensable vapor to tissue, comprising:

an elongated probe with an axis having an interior flow channel extending to at least one outlet in a probe working end;

a source of vapor media configured to provide a vapor flow through at least a portion of the interior flow channel located within the elongate probe, wherein the vapor has a minimum temperature; and a plurality of sensors in the interior flow channel for providing a signal of (i) flow rate of the vapor media in the interior flow channel, (ii) pressure of the vapor media in the interior flow channel, (iii) temperature of the vapor media in the interior flow channel, and (iv) vapor quality of the vapor media in the interior flow channel.

2. The medical system of claim 1, where the minimum temperature is selected from a group consisting of at least 80° C., 100° C., 120° C., 140° C. and 160° C.

3. The medical system of claim 1, wherein the sensor is selected from the group consisting of a temperature sensor, an impedance sensor, a pressure sensor and an optical sensor.

4. The medical system of claim 1, wherein a sensor is disposed in the working end.

5. The medical system of claim 1, wherein a sensor is disposed proximate to the at least one outlet.

6. The medical system of claim 1, wherein the plurality of sensors comprises a first and a second sensor, where the first and second sensors are axially spaced apart in the probe.

7. The medical system of claim 6, wherein a minimum spacing between the first and second sensors is selected from a group consisting of: 0.1 mm, 0.5 mm, 1 mm, 5 mm, 10 mm and 50 mm.

8. The medical system of claim 6, wherein first and second sensors are radially spaced apart in the probe.

9. The medical system of claim 1, wherein the source of vapor media includes a pressurized source of a liquid media and an energy source for phase conversion of the liquid media to a vapor media.

10. The medical system of claim 9, further comprising a controller capable of modulating a vapor parameter in response to a signal from at least one sensor of the plurality of sensors; the vapor parameter selected from the group of (i) flow rate of pressurized source of liquid media, (ii) inflow pressure of the pressurized source of liquid media, (iii) temperature of the liquid media, (iv) energy applied from the energy source to the liquid media, (v) flow rate of vapor media in the interior flow channel, (vi) pressure of the vapor media in the interior flow channel, (vi) temperature of the vapor media, and (vii) quality of vapor media.

11. The medical system of claim 9, wherein the energy source comprises at least one of a resistive heat source, an Rf energy source, a light energy source, a microwave energy source, an ultrasound source and an inductive heat source.

12. The medical system of claim 9, wherein the liquid source and controller are capable of providing a flow rate of the liquid media ranging from 0.001 ml/min to 20 ml/min, 0.010 ml/min to 10 ml/min, and 0.050 ml/min to 5 ml/min.

13. The medical system of claim 9, wherein the liquid source and controller are capable of providing an inflow pressure of the liquid media ranging from 1 psi to 1000 psi, 10 psi to 500 psi, and 50 psi to 200 psi.

14. The medical system of claim 1, wherein at least a portion of one or more of the plurality of sensors is embedded in at least a portion of a wall of the interior flow channel.

15. The medical system of claim 14, wherein at least a portion of one or more of the plurality of sensors is adjacent an insulative material.

16. A medical system for delivering high temperature condensable vapor to tissue, comprising:

an elongated probe with an axis having an interior flow channel extending within the elongated probe to at least one outlet in a probe working end, wherein a wall forming a perimeter of the interior flow channel includes an insulative portion having a thermal conductivity to limit thermal transfer away from the interior flow channel and limits thermal transfer between the wall and tissue;

a source of vapor media configured to provide a vapor flow through at least a portion of the interior flow channel, wherein the vapor has a minimum temperature;

a sensor configured to provide a signal indicative of a vapor quality in the interior flow channel; and a controller configured to modulate the vapor quality in the interior flow channel based at least partly on the signal provided by the sensor.

17. The medical system of claim 16, where the thermal conductivity is selected from a group consisting of 0.05 W/mK, 0.01 W/mK and 0.005 W/mK.

18. The medical system of claim 16, where the minimum temperature is selected from a group consisting of at least 80° C., 100° C., 120° C., 140° C. and 160° C.

19. The medical system of claim 16, where the elongated probe includes an extension member, where the interior flow channel comprises a first interior flow channel located within the extension member and extending to at least one outlet in a distal working end, and wherein the extension member includes an insulative portion to limit thermal transfer from the probe to tissue.

20. The medical system of claim 19, further comprising a second flow channel in the probe and extension member wherein a distal portion of the first and second flow channels are in fluid communication.

21. The medical system of claim 20, wherein the cross-section of a flow pathway of the at least one outlet is less than 20% of the second channel.

22. The medical system of claim 20, wherein a proximal end of the second channel is coupled to a negative pressure source.

23. The medical system of claim 19, wherein the at least one outlet includes at least one of a reduced cross-section region, a porous structure, a microchannel structure and a diffuser structure.

24. The medical system of claim 19, wherein the at least one flow outlet is proximate the working end of a needle, a catheter, a rigid probe or a clamp structure.

25. The medical system of claim 16, wherein the controller is further configured to modulate a pressure of the vapor flow in the interior flow channel and a temperature of the vapor flow in the interior flow channel.

26. The medical system of claim 25, further comprising at least one sensor in the interior flow channel.

27. The medical system of claim 26, wherein the controller is configured to receive a signal from the at least one sensor to modulate the quality of the vapor flow, the pressure of the vapor flow, or the temperature of the vapor flow.

28. The medical system of claim 16, wherein at least a portion of the sensor is embedded into at least a portion of the wall.

29. The medical system of claim 16, wherein at least a portion of the sensor is adjacent the insulative portion of the wall.

30. The medical system of claim 16, wherein the insulative portion has one or more openings to allow the vapor to flow through.

31. The medical system of claim 16, wherein one or more of the at least one outlet extends through at the insulative portion.

32. The medical system of claim 16, further comprising a retractable sheath, wherein the retractable sheath is moveable relative to the probe working end.

33. A medical system for delivering high temperature condensable vapor to tissue, comprising:
- an elongated probe with an axis having an interior flow channel extending to at least one outlet in a probe working end;
- a source of vapor media configured to provide a vapor flow through at least a portion of the interior flow channel located within the elongate probe, wherein the vapor has a minimum temperature; and
- a plurality of sensors in the interior flow channel for providing a signal of (i) existence of a flow of the vapor media, (ii) quantification of a flow rate of the vapor media, and (iii) quality of the flow of the vapor media.

34. A medical system for delivering high temperature condensable vapor to tissue, comprising:
- an elongated probe with an axis having an interior flow channel extending to at least one outlet in a probe working end;
- a source of vapor media configured to provide a vapor flow through at least a portion of the interior flow channel located within the elongate probe, wherein the vapor has a minimum temperature;
- at least one sensor in the interior flow channel for providing a signal of vapor quality of the vapor media in the interior flow channel; and
- a controller configured to modulate the vapor quality in the interior flow channel based at least partly on the signal provided by the sensor.

35. A medical system for delivering high temperature condensable vapor to tissue, comprising:
- an elongated probe with an axis having an interior flow channel extending within the elongated probe to at least one outlet in a probe working end, wherein a wall forming a perimeter of the interior flow channel includes an insulative portion having a thermal conductivity to limit thermal transfer away from the interior flow channel and limits thermal transfer between the wall and tissue;
- a source of vapor media configured to provide a vapor flow through at least a portion of the interior flow channel, wherein the vapor has a minimum temperature; and
- a controller configured to modulate vapor quality in the interior flow channel at least partly in response to a signal from one or more sensors configured to measure vapor quality in the interior flow channel.

36. A medical system for delivering high temperature condensable vapor to tissue, comprising:
- an elongated probe with an axis having an interior flow channel extending to at least one outlet in a probe working end;
- a source of vapor media configured to provide a vapor flow through at least a portion of the interior flow channel located within the elongate probe, wherein the vapor has a minimum temperature; and
- a controller configured to modulate vapor quality in the interior flow channel at least partly in response to a signal provided by one or more sensors configured to measure vapor quality in the interior flow channel.

* * * * *